(12) United States Patent
Kreke et al.

(10) Patent No.: US 10,369,173 B2
(45) Date of Patent: *Aug. 6, 2019

(54) OPTIMIZED METHODS FOR GENERATION OF CARDIAC STEM CELLS FROM CARDIAC TISSUE AND THEIR USE IN CARDIAC THERAPY

(71) Applicant: Capricor, Inc., Beverly Hills, CA (US)

(72) Inventors: Michelle Kreke, Marina del Rey, CA (US); Rachel Smith, Cary, NC (US)

(73) Assignee: Capricor, Inc., Beverly Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/837,549

(22) Filed: Dec. 11, 2017

(65) Prior Publication Data
US 2018/0169150 A1   Jun. 21, 2018

Related U.S. Application Data

(63) Continuation of application No. 14/403,078, filed as application No. PCT/US2013/043772 on May 31, 2013, now Pat. No. 9,884,076.

(60) Provisional application No. 61/655,928, filed on Jun. 5, 2012.

(51) Int. Cl.
*A61K 35/34* (2015.01)
*C12N 5/00* (2006.01)
*C12N 5/077* (2010.01)
*A61K 35/00* (2006.01)

(52) U.S. Cl.
CPC ............ *A61K 35/34* (2013.01); *C12N 5/0657* (2013.01); *A61K 35/00* (2013.01); *C12N 2500/32* (2013.01); *C12N 2501/91* (2013.01); *C12N 2509/00* (2013.01); *C12N 2523/00* (2013.01)

(58) Field of Classification Search
CPC ....... A61K 35/34; A61K 35/00; C12N 5/0657
See application file for complete search history.

(56) References Cited

U.S. PATENT DOCUMENTS 9,884,076 B2 *   2/2018   Kreke ................. C12N 5/0657

\* cited by examiner

*Primary Examiner* — Ruth A Davis
(74) *Attorney, Agent, or Firm* — Tony Uhm; Capricor, Inc.

(57) ABSTRACT

The present disclosure relates generally to methods for the increased processing of tissue for the generation of cardiac stem cells, wherein the stem cells are suitable for use in cardiac stem cell therapy. In particular, several embodiments relate to the processing of allogeneic donor cardiac tissue for the generation of multiple patient doses of cardiac stem cells.

20 Claims, 68 Drawing Sheets

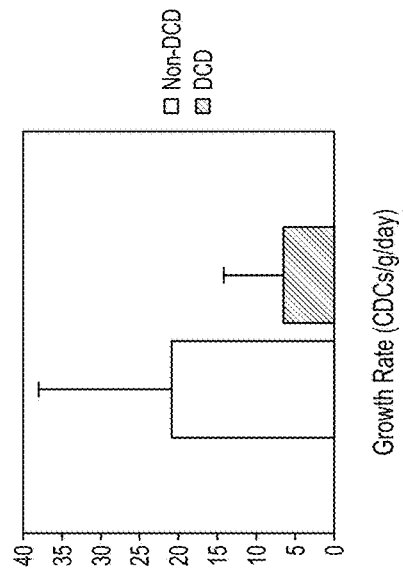
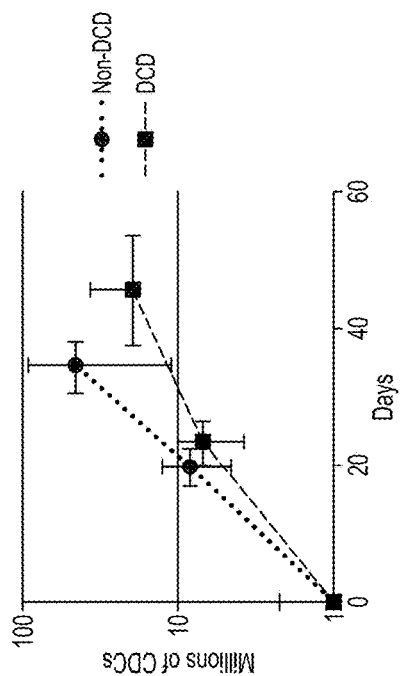
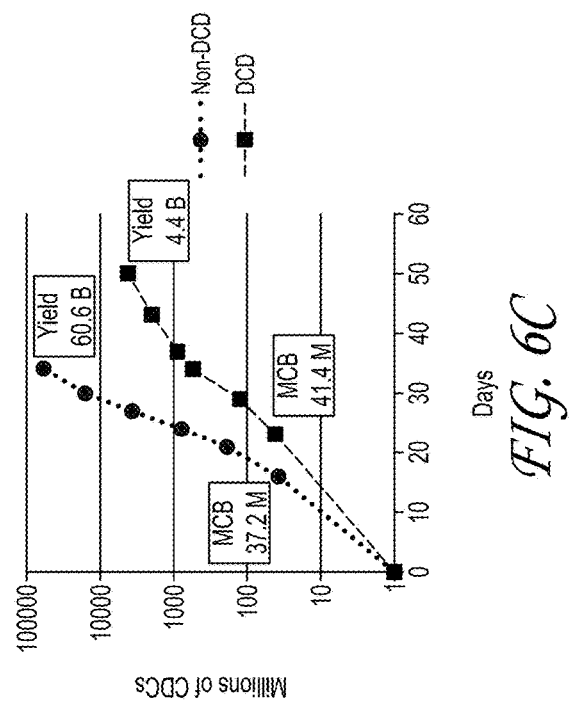
FIG. 6A
FIG. 6B
FIG. 6C

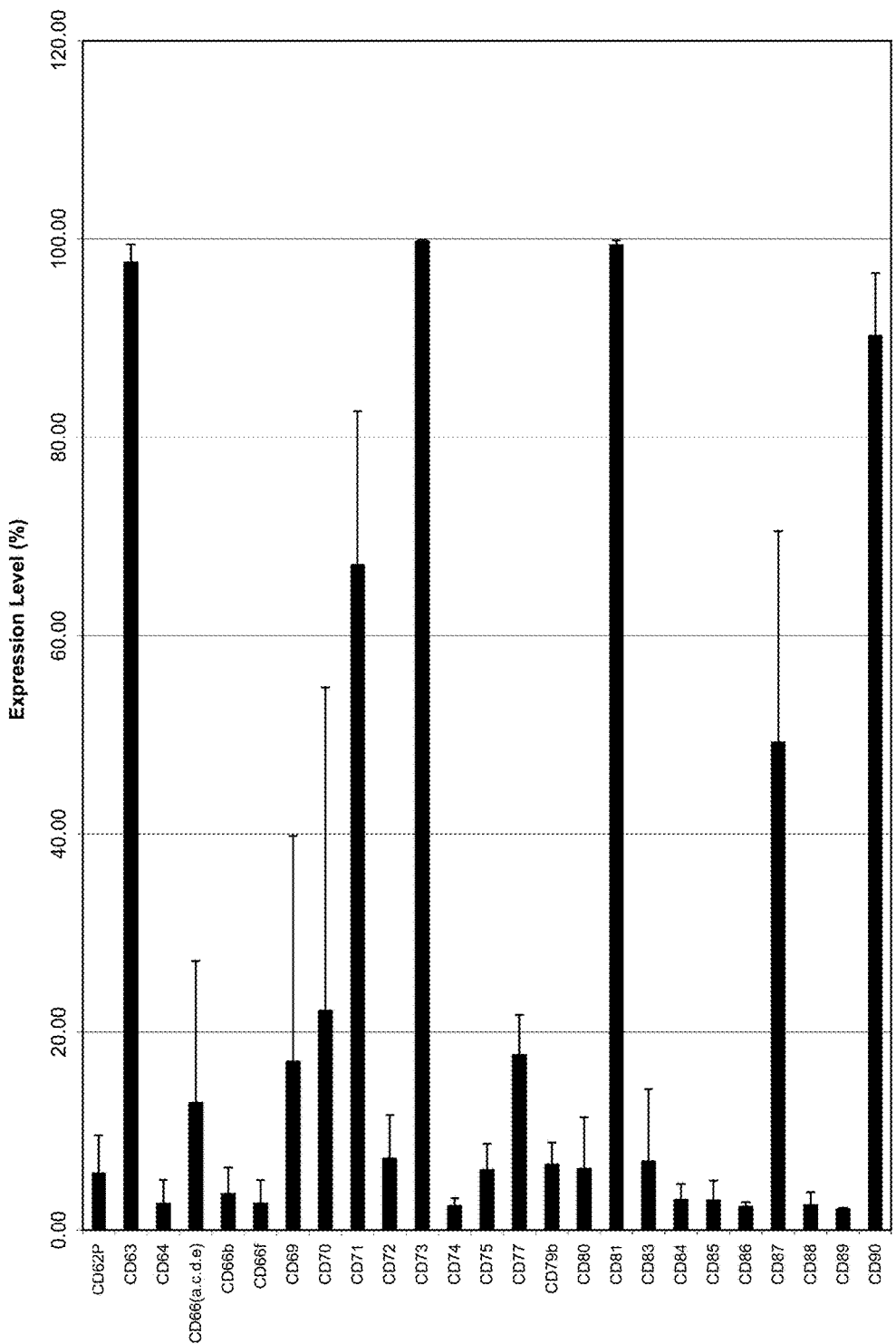

Table 10 - EDC Cell Surface Marker Expression by EDC Line and Average

| Marker | EDC Line #1 | EDC Line #2 | EDC Line #5 | EDC Line #6 | Average | Std. Dev |
|---|---|---|---|---|---|---|
| CD1a | 2.56 | 1.07 | 0.39 | 1.50 | 1.38 | 0.91 |
| CD1b | 2.83 | 1.97 | 0.45 | 3.12 | 2.09 | 1.20 |
| CD1d | 7.56 | 0.90 | 0.31 | 1.41 | 2.54 | 3.37 |
| CD2 | 1.56 | 1.58 | 0.48 | 1.23 | 1.21 | 0.51 |
| CD3 | 5.58 | 1.23 | 0.45 | 1.37 | 2.16 | 2.32 |
| CD4 | 3.25 | 1.45 | 0.38 | 1.28 | 1.59 | 1.20 |
| CD4v4 | 4.26 | 2.61 | 0.98 | 2.62 | 2.62 | 1.34 |
| CD5 | 11.10 | 1.30 | 0.31 | 1.77 | 3.62 | 5.02 |
| CD6 | 2.42 | 1.11 | 0.47 | 1.21 | 1.30 | 0.81 |
| CD7 | 2.53 | 0.94 | 0.30 | 1.32 | 1.27 | 0.94 |
| CD8a | 1.85 | 0.76 | 0.36 | 1.02 | 1.00 | 0.63 |
| CD8b | 1.87 | 1.12 | 0.48 | 1.61 | 1.27 | 0.61 |
| CD9 | 99.80 | 99.80 | 99.50 | 99.60 | 99.68 | 0.15 |
| CD10 | 80.70 | 47.60 | 29.30 | 63.90 | 55.38 | 22.02 |
| CD11a | 4.01 | 1.00 | 0.55 | 1.54 | 1.78 | 1.54 |
| CD11b | 1.34 | 1.46 | 0.50 | 1.25 | 1.14 | 0.43 |
| CD11c | 1.52 | 0.98 | 0.25 | 1.15 | 0.97 | 0.54 |
| CD13 | 98.90 | 96.60 | 98.80 | 99.30 | 98.40 | 1.22 |
| CD14 | 5.52 | 1.63 | 1.34 | 2.20 | 2.67 | 1.93 |
| CD15 | 3.03 | 3.67 | 2.78 | 2.20 | 2.92 | 0.61 |
| CD15s | 1.62 | 0.68 | 0.29 | 1.28 | 0.97 | 0.60 |
| CD16 | 2.06 | 0.99 | 0.25 | 1.50 | 1.20 | 0.77 |
| CD18 | 2.00 | 0.94 | 0.50 | 1.47 | 1.23 | 0.65 |
| CD19 | 1.63 | 1.06 | 0.30 | 1.49 | 1.12 | 0.60 |
| CD20 | 2.71 | 1.82 | 0.29 | 1.70 | 1.63 | 1.00 |
| CD21 | 1.88 | 1.25 | 0.33 | 1.59 | 1.26 | 0.67 |
| CD22 | 3.58 | 1.18 | 0.47 | 1.57 | 1.70 | 1.34 |
| CD23 | 1.71 | 1.36 | 0.49 | 1.39 | 1.24 | 0.52 |
| CD24 | 13.70 | 5.74 | 4.21 | 10.50 | 8.54 | 4.36 |
| CD25 | 1.81 | 1.28 | 0.56 | 1.73 | 1.34 | 0.57 |
| CD26 | 99.60 | 99.30 | 99.70 | 99.90 | 99.63 | 0.25 |
| CD27 | 2.62 | 1.54 |  | 3.30 | 2.49 | 0.89 |
| CD28 | 2.47 | 1.21 |  | 1.74 | 1.81 | 0.63 |
| CD29 | 99.60 | 95.80 |  | 98.10 | 97.83 | 1.91 |

*FIG. 18A*

Table 10 (continued).

| Marker | EDC Line #1 | EDC Line #2 | EDC Line #5 | EDC Line #6 | Average | Std. Dev |
|---|---|---|---|---|---|---|
| CD30 | 17.20 | 4.78 | | 4.90 | 8.96 | 7.14 |
| CD31 | 25.60 | 23.90 | | 19.90 | 23.13 | 2.93 |
| CD32 | 2.64 | 1.54 | | 1.34 | 1.84 | 0.70 |
| CD33 | 2.00 | 1.44 | | 1.51 | 1.65 | 0.31 |
| CD34 | 28.60 | 27.50 | | 25.40 | 27.17 | 1.63 |
| CD35 | 1.79 | 1.27 | | 1.65 | 1.57 | 0.27 |
| CD36 | 3.76 | 2.02 | | 2.88 | 2.89 | 0.87 |
| CD37 | 2.10 | 1.11 | | 2.02 | 1.74 | 0.55 |
| CD38 | 4.78 | 1.57 | | 5.29 | 3.88 | 2.02 |
| CD39 | 3.30 | 1.50 | | 4.89 | 3.23 | 1.70 |
| CD40 | 23.60 | 10.60 | | 16.00 | 16.73 | 6.53 |
| CD41a | 2.29 | 1.09 | | 6.71 | 3.36 | 2.96 |
| CD41b | 1.70 | 1.05 | | 3.35 | 2.03 | 1.19 |
| CD42a | 5.53 | 4.60 | 1.40 | 6.10 | 4.41 | 2.10 |
| CD42b | 4.34 | 2.56 | 0.12 | 3.00 | 2.50 | 1.76 |
| CD43 | 2.06 | 1.72 | 0.38 | 1.90 | 1.52 | 0.77 |
| CD44 | 99.70 | 98.80 | 99.90 | 99.90 | 99.58 | 0.53 |
| CD45 | 2.45 | 1.19 | 0.73 | 2.13 | 1.63 | 0.80 |
| CD45RA | 3.65 | 2.74 | 1.14 | 2.69 | 2.56 | 1.04 |
| CD45RB | 5.00 | 1.36 | 6.37 | 1.78 | 3.63 | 2.45 |
| CD45RO | 2.89 | 2.04 | 1.40 | 6.05 | 3.10 | 2.06 |
| CD46 | 99.80 | 99.10 | 99.80 | 99.80 | 99.63 | 0.35 |
| CD47 | 99.80 | 99.80 | 99.80 | 99.60 | 99.75 | 0.10 |
| CD48 | 2.86 | 1.57 | | 11.90 | 5.44 | 5.63 |
| CD49a | 71.90 | 15.10 | | 83.70 | 56.90 | 36.68 |
| CD49b | 99.80 | 99.50 | | 99.70 | 99.67 | 0.15 |
| CD49c | 99.80 | 99.90 | | 99.90 | 99.87 | 0.06 |
| CD49d | 86.10 | 70.80 | | 73.50 | 76.80 | 8.17 |
| CD49e | 99.90 | 98.40 | | 99.90 | 99.40 | 0.87 |
| CD50 | 5.78 | 2.46 | | 3.09 | 3.78 | 1.76 |
| CD51/61 | 99.90 | 99.10 | | 99.30 | 99.43 | 0.42 |
| CD53 | 2.74 | 2.05 | | 6.16 | 3.65 | 2.20 |
| CD54 | 99.00 | 93.20 | | 98.90 | 97.03 | 3.32 |
| CD55 | 99.50 | 98.70 | | 99.10 | 99.10 | 0.40 |
| CD56 | 44.40 | 16.40 | | 21.30 | 27.37 | 14.95 |

*FIG. 18B*

Table 10 (continued).

| Marker | EDC Line #1 | EDC Line #2 | EDC Line #5 | EDC Line #6 | Average | Std. Dev |
|---|---|---|---|---|---|---|
| *CD57* | 2.49 | 1.39 | | 27.00 | 10.29 | 14.48 |
| CD58 | 99.50 | 99.60 | | 99.90 | 99.67 | 0.21 |
| CD59 | 99.70 | 99.40 | | 99.70 | 99.60 | 0.17 |
| CD61 | 99.80 | 99.90 | | 99.90 | 99.87 | 0.06 |
| CD62E | 6.29 | 4.99 | | 3.38 | 4.89 | 1.46 |
| CD62L | 3.27 | 1.98 | | 4.50 | 3.25 | 1.26 |
| CD62P | 10.20 | 3.51 | | 3.57 | 5.76 | 3.85 |
| CD63 | 99.50 | 95.90 | | 97.50 | 97.63 | 1.80 |
| CD64 | 0.67 | 2.09 | | 5.37 | 2.71 | 2.41 |
| *CD66(a.c.d.e)* | 4.73 | 4.48 | | 29.40 | 12.87 | 14.32 |
| CD66b | 2.54 | 1.85 | | 6.73 | 3.71 | 2.64 |
| CD66f | 1.71 | 1.06 | | 5.43 | 2.73 | 2.36 |
| *CD69* | 4.82 | 2.97 | | 43.30 | 17.03 | 22.77 |
| *CD70* | 5.07 | 1.59 | | 59.80 | 22.15 | 32.65 |
| *CD71* | 84.40 | 54.40 | | 62.60 | 67.13 | 15.51 |
| CD72 | 5.70 | 3.90 | | 12.20 | 7.27 | 4.37 |
| CD73 | 99.80 | 99.90 | | 99.60 | 99.77 | 0.15 |
| CD74 | 3.19 | 2.63 | | 1.65 | 2.49 | 0.78 |
| CD75 | 4.49 | 4.71 | | 9.15 | 6.12 | 2.63 |
| CD77 | 20.60 | 13.10 | | 19.40 | 17.70 | 4.03 |
| CD79b | 7.36 | 4.23 | | 8.44 | 6.68 | 2.19 |
| CD80 | 12.20 | 2.88 | | 3.59 | 6.22 | 5.19 |
| CD81 | 98.90 | 99.30 | | 99.90 | 99.37 | 0.50 |
| CD83 | 3.88 | 1.74 | | 15.30 | 6.97 | 7.29 |
| CD84 | 3.91 | 1.27 | | 4.13 | 3.10 | 1.59 |
| CD85 | 5.03 | 1.02 | | 3.08 | 3.04 | 2.01 |
| CD86 | 2.92 | 2.14 | | 2.12 | 2.39 | 0.46 |
| *CD87* | 42.40 | 73.10 | | 32.10 | 49.20 | 21.33 |
| CD88 | 4.06 | 2.07 | | 1.55 | 2.56 | 1.32 |
| CD89 | 2.29 | 2.00 | | 2.16 | 2.15 | 0.15 |
| CD90 | 94.20 | 93.60 | | 83.00 | 90.27 | 6.30 |
| *CD91* | 70.70 | 77.70 | | 79.00 | 75.80 | 4.46 |
| *CDw93* | 2.82 | 9.62 | | 14.00 | 8.81 | 5.63 |
| CD94 | 2.09 | 2.36 | | 1.40 | 1.95 | 0.50 |
| CD95 | 99.80 | 99.90 | | 98.90 | 99.53 | 0.55 |

*FIG. 18C*

Table 10 (continued).

| Marker | EDC Line #1 | EDC Line #2 | EDC Line #5 | EDC Line #6 | Average | Std. Dev |
|---|---|---|---|---|---|---|
| CD97 | 61.00 | 58.70 | | 66.70 | 62.13 | 4.12 |
| CD98 | 99.80 | 99.60 | | 99.90 | 99.77 | 0.15 |
| CD99 | 99.30 | 99.60 | | 99.80 | 99.57 | 0.25 |
| CD99R | 53.90 | 64.40 | | 60.30 | 59.53 | 5.29 |
| CD100 | 2.33 | 2.18 | | 1.49 | 2.00 | 0.45 |
| *CD102* | 19.10 | 39.90 | | 13.80 | 24.27 | 13.80 |
| CD103 | 1.37 | 1.84 | | 1.30 | 1.50 | 0.29 |
| CD105 | 99.50 | 99.80 | | 99.50 | 99.60 | 0.17 |
| CD106 | 12.70 | 11.70 | | 13.80 | 12.73 | 1.05 |
| *CD107a* | 75.40 | 65.10 | | 25.50 | 55.33 | 26.34 |
| CD107b | 21.70 | 15.00 | | 13.70 | 16.80 | 4.29 |
| CD108 | 83.10 | 97.40 | | 92.80 | 91.10 | 7.30 |
| *CD109* | 28.50 | 73.20 | | 44.00 | 48.57 | 22.70 |
| *CD112* | 15.70 | 33.00 | | 12.60 | 20.43 | 10.99 |
| CD114 | 2.70 | 1.77 | | 1.76 | 2.08 | 0.54 |
| CD116 | 2.87 | 2.93 | | 3.05 | 2.95 | 0.09 |
| CD117 | 2.65 | 2.89 | | 1.87 | 2.47 | 0.53 |
| CD118 (LIF rcptr) | 8.84 | 3.72 | | 3.02 | 5.19 | 3.18 |
| *CD119* | 57.80 | 80.00 | | 56.50 | 64.77 | 13.21 |
| CD120a | 27.00 | 39.40 | | 23.10 | 29.83 | 8.51 |
| CD121a | 12.70 | 0.00 | | 16.60 | 9.77 | 8.68 |
| CD121b | 3.21 | 4.55 | | 2.21 | 3.32 | 1.17 |
| CD122 | 3.06 | 3.71 | | 3.39 | 3.39 | 0.33 |
| CD123 | 2.07 | 4.27 | | 1.32 | 2.55 | 1.53 |
| CD124 | 9.18 | 8.13 | | 6.25 | 7.85 | 1.48 |
| CD126 | 2.23 | 2.16 | | 0.75 | 1.71 | 0.84 |
| CD127 | 2.11 | 1.90 | | 1.80 | 1.94 | 0.16 |
| CD128b | 2.42 | 2.44 | | 1.64 | 2.17 | 0.46 |
| CD130 | 83.20 | 93.90 | | 78.10 | 85.07 | 8.06 |
| CD134 | 13.40 | 3.70 | | 2.45 | 6.52 | 5.99 |
| CD135 | 1.54 | 2.41 | | 1.57 | 1.84 | 0.49 |
| CD137 | 6.72 | 11.30 | | 9.47 | 9.16 | 2.31 |
| CD137L | 3.75 | 4.68 | | 4.63 | 4.35 | 0.52 |
| CD138 | 2.89 | 7.26 | | 2.48 | 4.21 | 2.65 |
| *CD140a* | 48.80 | 83.10 | | 74.20 | 68.70 | 17.80 |

*FIG. 18D*

Table 10 (continued).

| Marker | EDC Line #1 | EDC Line #2 | EDC Line #5 | EDC Line #6 | Average | Std. Dev |
|---|---|---|---|---|---|---|
| CD140b | 2.38 | 8.63 | | 15.60 | 8.87 | 6.61 |
| CD141 | 77.50 | 85.70 | | 71.50 | 78.23 | 7.13 |
| CD142 | 89.60 | 91.20 | | 91.90 | 90.90 | 1.18 |
| CD144 | 10.30 | 19.20 | | 5.46 | 11.65 | 6.97 |
| *CD146* | 64.50 | 90.20 | | 68.00 | 74.23 | 13.94 |
| CD147 | 99.60 | 99.50 | | 99.70 | 99.60 | 0.10 |
| *CD150* | 22.00 | 5.06 | | 2.26 | 9.77 | 10.68 |
| CD151 | 99.60 | 99.30 | | 99.70 | 99.53 | 0.21 |
| *CD152* | 30.10 | 32.40 | | 8.36 | 23.62 | 13.27 |
| CD153 | 4.15 | 5.56 | | 9.79 | 6.50 | 2.94 |
| CD154 | 2.14 | 7.28 | | 2.91 | 4.11 | 2.77 |
| CD158a | 1.22 | 2.15 | | 1.61 | 1.66 | 0.47 |
| *CD158b* | 2.53 | 26.60 | | 2.17 | 10.43 | 14.00 |
| CD161 | 1.90 | 2.39 | | 1.25 | 1.85 | 0.57 |
| CD162 | 2.99 | 4.74 | | 1.45 | 3.06 | 1.65 |
| CD163 | 1.50 | 2.21 | | 1.89 | 1.87 | 0.36 |
| *CD164* | 81.00 | 81.10 | | 53.50 | 71.87 | 15.91 |
| CD165 | 95.40 | 99.40 | | 98.70 | 97.83 | 2.14 |
| CD166 | 99.70 | 99.80 | | 99.70 | 99.73 | 0.06 |
| *CD171* | 5.07 | 24.40 | | 2.89 | 10.79 | 11.84 |
| CD172b | 6.89 | 20.10 | | 3.27 | 10.09 | 8.86 |
| CD177 | 2.02 | 7.76 | | 1.26 | 3.68 | 3.55 |
| CD178 | 1.75 | 11.10 | | 2.43 | 5.09 | 5.21 |
| CD180 | 3.08 | 4.04 | | 3.31 | 3.48 | 0.50 |
| CD181 | 3.41 | 9.49 | | 4.09 | 5.66 | 3.33 |
| CD183 | 5.26 | 6.64 | | 4.48 | 5.46 | 1.09 |
| CD184 | 4.02 | 6.24 | | 2.32 | 4.19 | 1.97 |
| CD193 | 2.06 | 2.49 | | 2.72 | 2.42 | 0.34 |
| CD195 | 3.20 | 3.62 | | 1.76 | 2.86 | 0.98 |
| CD196 | 3.32 | 2.54 | | 3.83 | 3.23 | 0.65 |
| CD197 | 3.07 | 2.15 | | 3.45 | 2.89 | 0.67 |
| CD200 | 98.70 | 92.20 | | 95.70 | 95.53 | 3.25 |
| CD205 | 4.66 | 4.54 | | 4.64 | 4.61 | 0.06 |
| CD206 | 1.67 | 6.46 | | 1.16 | 3.10 | 2.92 |
| CD209 | 5.21 | 14.30 | | 14.40 | 11.30 | 5.28 |

*FIG. 18E*

Table 10 (continued).

| Marker | EDC Line #1 | EDC Line #2 | EDC Line #5 | EDC Line #6 | Average | Std. Dev |
|---|---|---|---|---|---|---|
| *CD220* | 53.30 | 47.00 | | 67.80 | 56.03 | 10.67 |
| *CD221* | 87.60 | 61.60 | | 67.40 | 72.20 | 13.65 |
| CD226 | 3.54 | 7.80 | | 4.43 | 5.26 | 2.25 |
| CD227 | 71.50 | 80.90 | | 80.60 | 77.67 | 5.34 |
| CD229 | 1.55 | 1.91 | | 1.63 | 1.70 | 0.19 |
| CD231 | 12.00 | 2.89 | | 1.75 | 5.55 | 5.62 |
| CD235a | 5.03 | 3.18 | | 2.87 | 3.69 | 1.17 |
| CD243 (p-glycoProtein) | 2.71 | 3.27 | | 5.98 | 3.99 | 1.75 |
| CD244 | 1.31 | 3.79 | | 2.09 | 2.40 | 1.27 |
| CD255 (Tweak) | 1.86 | 8.41 | | 4.78 | 5.02 | 3.28 |
| *CD268* | 2.41 | 29.60 | | 1.11 | 11.04 | 16.09 |
| *CD271* | 13.00 | 36.70 | | 5.64 | 18.45 | 16.23 |
| *CD273* | 89.10 | 30.40 | | 89.30 | 69.60 | 33.95 |
| CD274 | 97.40 | 95.90 | | 92.40 | 95.23 | 2.57 |
| CD275 (B7-H2) | 5.70 | 5.14 | | 7.07 | 5.97 | 0.99 |
| CD278 | 3.19 | 2.38 | | 0.66 | 2.08 | 1.29 |
| CD279 | 4.67 | 1.45 | | 1.45 | 2.52 | 1.86 |
| CD282 | 3.23 | 1.02 | | 1.06 | 1.77 | 1.26 |
| CD305(LAIR-1) | 3.72 | 1.25 | | 1.26 | 2.08 | 1.42 |
| CD309 | 15.20 | 4.75 | | 1.59 | 7.18 | 7.12 |
| CD314(NKG2D) | 3.69 | 1.60 | | 1.40 | 2.23 | 1.27 |
| *CD321(F11 Rcptr)* | 91.60 | 59.20 | | 54.70 | 68.50 | 20.13 |
| CDw327 | 4.28 | 1.43 | | 1.25 | 2.32 | 1.70 |
| CDw328 | 4.17 | 2.32 | | 1.83 | 2.77 | 1.23 |
| CDw329 | 3.80 | 1.97 | | 2.39 | 2.72 | 0.96 |
| CD335(NKP46) | 3.62 | 1.45 | | 2.12 | 2.40 | 1.11 |
| CD336 | 3.63 | 1.28 | | 1.39 | 2.10 | 1.33 |
| CD337 | 4.32 | 2.36 | | 4.35 | 3.68 | 1.14 |
| CD338(ABCG2) | 15.70 | 2.88 | | 2.91 | 7.16 | 7.39 |
| CD340(Her2) | 98.80 | 98.60 | | 95.10 | 97.50 | 2.08 |
| abTCR | 4.19 | 2.69 | | 3.37 | 3.42 | 0.75 |
| B2-uGlob | 99.30 | 99.10 | | 99.40 | 99.27 | 0.15 |
| BLTR-1 | 5.03 | 2.28 | | 2.71 | 3.34 | 1.48 |
| CLIP | 5.31 | 2.09 | | 2.06 | 3.15 | 1.87 |

*FIG. 18F*

Table 10 (continued).

| Marker | EDC Line #1 | EDC Line #2 | EDC Line #5 | EDC Line #6 | Average | Std. Dev |
|---|---|---|---|---|---|---|
| CMRF-44 | 9.66 | 4.75 | | 2.85 | 5.75 | 3.51 |
| CMRF-56 | 5.03 | 2.77 | | 2.26 | 3.35 | 1.47 |
| EGF-r | 98.80 | 99.20 | | 99.60 | 99.20 | 0.40 |
| Fmlp-r | 4.77 | 1.81 | | 2.47 | 3.02 | 1.55 |
| gd TCR | 4.61 | 1.90 | | 2.41 | 2.97 | 1.44 |
| Hem. Prog. Cell | 44.10 | 15.30 | | 38.50 | 32.63 | 15.27 |
| HLA-A,B,C | 99.60 | 99.30 | | 99.80 | 99.57 | 0.25 |
| HLA-A2 | 99.40 | 99.40 | | 1.61 | 66.80 | 56.46 |
| HLA-DQ | 54.60 | 30.30 | | 24.80 | 36.57 | 15.86 |
| HLA-DR | 4.52 | 1.65 | | 1.80 | 2.66 | 1.62 |
| HLA-DR,DP,DQ | 5.53 | 2.51 | | 2.78 | 3.61 | 1.67 |
| Invariant NKT | 4.42 | 1.47 | | 1.63 | 2.51 | 1.66 |
| Disialoganglioside GD2 | 10.50 | 2.28 | | 2.18 | 4.99 | 4.77 |
| MIC A/B | 73.00 | 95.10 | | 18.40 | 62.17 | 39.48 |
| NKB1 | 3.74 | 1.85 | | 1.88 | 2.49 | 1.08 |
| SSEA-1 | 22.70 | 19.60 | | 6.59 | 16.30 | 8.55 |
| SSEA-4 | 52.40 | 32.10 | | 30.10 | 38.20 | 12.34 |
| TRA-1-60 | 2.76 | 1.09 | | 1.24 | 1.70 | 0.92 |
| TRA-1-81 | 2.60 | 1.29 | 0.26 | 1.28 | 1.36 | 0.96 |
| Vb 23 | 4.04 | 2.60 | 0.84 | 2.54 | 2.51 | 1.31 |
| Vb 8 | 4.26 | 2.19 | 0.79 | 2.10 | 2.33 | 1.44 |
| CD49f | 69.40 | 53.80 | 0.00 | 43.70 | 41.73 | 29.76 |
| CD104 | 2.56 | 1.52 | 0.55 | 1.21 | 1.46 | 0.84 |
| CD120b | 3.57 | 1.78 | 0.58 | 1.16 | 1.77 | 1.29 |
| CD132 | 3.49 | 1.77 | 0.80 | 1.06 | 1.78 | 1.21 |
| CD201 | 58.90 | 65.90 | 55.40 | 70.50 | 62.68 | 6.80 |
| CD210 | 4.36 | 1.62 | 0.57 | 1.80 | 2.09 | 1.61 |
| CD212 | 3.62 | 1.29 | 0.61 | 1.16 | 1.67 | 1.33 |
| CD267 | 4.10 | 1.29 | 0.57 | 1.11 | 1.77 | 1.58 |
| CD294 | 4.37 | 1.34 | 1.03 | 1.04 | 1.95 | 1.62 |
| CD326 | 44.60 | 16.70 | 23.20 | 10.40 | 23.73 | 14.87 |
| Cutaneous Lymph. Antigen | 68.40 | 25.80 | 21.00 | 23.60 | 34.70 | 22.55 |

*FIG. 18G*

Table 10 (continued).

| Marker | EDC Line #1 | EDC Line #2 | EDC Line #5 | EDC Line #6 | Average | Std. Dev |
|---|---|---|---|---|---|---|
| INT B7 | 3.73 | 1.37 | 0.45 | 1.14 | 1.67 | 1.43 |
| SSEA-3 | 15.50 | 24.30 | 27.50 | 16.80 | 21.03 | 5.80 |

*FIG. 18H*

Table 11 - CDC Cell Surface Marker Expression by CDC Line and Average

| Marker | CDC Line #1 | CDC Line #2 | CDC Line #3 | CDC Line #4 | CDC Line #5 | CDC Line #6 | Average | Std. Dev. |
|---|---|---|---|---|---|---|---|---|
| *CD1a* | 2.07 | 39.60 | 1.15 | | 1.27 | 22.10 | 13.24 | 17.23 |
| CD1b | 3.26 | 4.27 | | 0.71 | 2.86 | 2.72 | 2.76 | 1.30 |
| *CD1d* | 16.30 | 2.52 | 0.47 | 0.53 | 1.13 | 55.30 | 12.71 | 21.74 |
| *CD2* | 10.90 | 3.31 | 1.13 | | 1.93 | 35.30 | 10.51 | 14.39 |
| CD3 | 3.15 | 12.00 | 1.91 | | 1.78 | 3.87 | 4.54 | 4.26 |
| CD4 | 2.32 | 3.45 | 1.75 | 0.90 | 0.83 | 1.67 | 1.82 | 0.98 |
| CD4v4 | 6.38 | 8.56 | 2.18 | | 4.66 | 4.26 | 5.21 | 2.40 |
| CD5 | 2.34 | 2.72 | 1.25 | | 1.48 | 1.83 | 1.92 | 0.61 |
| CD6 | 20.50 | 3.91 | 0.66 | | 1.22 | 2.13 | 5.68 | 8.37 |
| CD7 | 2.69 | 4.81 | | | 1.75 | 2.09 | 2.84 | 1.37 |
| CD8a | 3.43 | 3.17 | 1.21 | 0.75 | 1.41 | 2.80 | 2.13 | 1.14 |
| CD8b | 1.87 | 2.14 | | | 2.20 | 1.86 | 2.02 | 0.18 |
| CD9 | 99.80 | 99.80 | 97.70 | 96.60 | 99.80 | 99.90 | 98.93 | 1.43 |
| *CD10* | 98.00 | 68.60 | 27.90 | 21.50 | 52.90 | 83.20 | 58.68 | 30.36 |
| *CD11a* | 4.89 | 1.77 | 2.00 | | 1.38 | 55.70 | 13.15 | 23.83 |
| CD11b | 4.57 | 2.47 | 2.61 | | 1.14 | 1.67 | 2.49 | 1.31 |
| CD11c | 2.16 | 11.40 | 1.39 | | 1.04 | 3.21 | 3.84 | 4.31 |
| CD13 | 99.80 | 99.60 | 89.40 | | 99.60 | 99.30 | 97.54 | 4.55 |
| CD14 | 5.46 | 10.40 | | | 2.50 | 6.69 | 6.26 | 3.27 |
| *CD15* | 30.60 | 56.60 | | | 62.90 | 7.97 | 39.52 | 25.25 |
| CD15s | 1.85 | 3.27 | 1.97 | | 1.21 | 2.12 | 2.08 | 0.75 |
| CD16 | 3.56 | 3.53 | | 0.56 | 1.11 | 1.91 | 2.13 | 1.37 |
| CD18 | 4.23 | 7.17 | 1.67 | | 1.36 | 1.96 | 3.28 | 2.45 |
| CD19 | 1.69 | 2.19 | 0.99 | | 1.99 | 1.75 | 1.72 | 0.46 |
| *CD20* | 2.23 | 3.42 | 2.49 | | 2.33 | 27.70 | 7.63 | 11.23 |
| CD21 | 4.49 | 3.72 | 1.05 | | 3.39 | 2.74 | 3.08 | 1.30 |
| *CD22* | 5.00 | 1.90 | 1.56 | | 1.32 | 71.90 | 16.34 | 31.10 |
| CD23 | 4.92 | 11.10 | 2.17 | | 1.30 | 1.58 | 4.21 | 4.11 |
| *CD24* | 8.11 | 21.80 | | | 6.98 | 37.60 | 18.62 | 14.33 |
| CD25 | 2.90 | 3.38 | 1.87 | | 2.30 | 2.12 | 2.51 | 0.62 |
| CD26 | 99.90 | 99.80 | 98.40 | | 99.40 | 99.80 | 99.46 | 0.62 |
| CD27 | 3.38 | 10.40 | 1.91 | 1.30 | 2.18 | 2.54 | 3.62 | 3.39 |
| CD28 | 3.13 | 5.27 | 1.69 | | 2.05 | 2.45 | 2.92 | 1.42 |
| CD29 | 97.80 | 85.10 | 84.10 | | 88.40 | 99.70 | 91.02 | 7.26 |

*FIG. 19A*

Table 11 (continued).

| Marker | CDC Line #1 | CDC Line #2 | CDC Line #3 | CDC Line #4 | CDC Line #5 | CDC Line #6 | Average | Std. Dev. |
|---|---|---|---|---|---|---|---|---|
| CD30 | 18.00 | 6.51 | 1.06 | | 2.63 | 5.88 | 6.82 | 6.65 |
| *CD31* | 67.40 | 50.30 | 12.70 | | 59.70 | 49.40 | 47.90 | 21.02 |
| CD32 | 2.51 | 2.98 | 1.35 | 0.86 | 1.49 | 9.44 | 3.11 | 3.20 |
| CD33 | 2.97 | 2.34 | | | 0.96 | 2.58 | 2.21 | 0.88 |
| *CD34* | 11.10 | 38.00 | | | 15.50 | 77.10 | 35.43 | 30.18 |
| CD35 | 5.13 | 3.65 | 1.68 | | 2.34 | 1.92 | 2.94 | 1.44 |
| CD36 | 3.50 | 7.18 | | 2.03 | 2.91 | 5.15 | 4.15 | 2.04 |
| CD37 | 2.58 | 2.75 | 1.68 | | 1.09 | 2.26 | 2.07 | 0.68 |
| CD38 | 9.08 | 16.00 | | | 1.99 | 6.31 | 8.35 | 5.88 |
| *CD39* | 6.55 | 5.16 | 1.51 | | 1.87 | 48.80 | 12.78 | 20.25 |
| CD40 | 17.10 | 8.29 | | 1.21 | 4.78 | 17.40 | 9.76 | 7.29 |
| CD41a | 20.80 | 9.50 | 1.85 | | 1.28 | 1.97 | 7.08 | 8.38 |
| CD41b | 3.95 | 9.10 | 1.21 | 0.80 | 1.23 | 2.24 | 3.09 | 3.16 |
| CD42a | 6.25 | 15.20 | | 3.54 | 4.41 | 2.61 | 6.40 | 5.10 |
| CD42b | 3.81 | 4.53 | 1.39 | 1.07 | 2.09 | 8.38 | 3.55 | 2.73 |
| CD43 | 3.51 | 3.88 | 3.00 | | 2.18 | 3.36 | 3.19 | 0.64 |
| CD44 | 99.50 | 99.70 | 95.50 | 90.30 | 99.70 | 99.40 | 97.35 | 3.82 |
| CD45 | | 5.58 | 1.88 | | 2.13 | 2.44 | 3.01 | 1.73 |
| CD45RA | 5.72 | 7.79 | 1.53 | | 2.14 | 3.96 | 4.23 | 2.58 |
| CD45RB | 3.08 | 5.08 | 1.24 | | 1.66 | 2.00 | 2.61 | 1.54 |
| CD45RO | 4.60 | 6.01 | 1.92 | | 2.60 | 3.08 | 3.64 | 1.65 |
| CD46 | 99.50 | 99.80 | 96.50 | | 99.40 | 99.70 | 98.98 | 1.40 |
| CD47 | 99.60 | 99.30 | 91.80 | 98.80 | 99.80 | 99.90 | 98.20 | 3.16 |
| *CD48* | 67.70 | 3.84 | 2.94 | 6.31 | 2.93 | 1.99 | 14.29 | 26.21 |
| *CD49a* | 64.20 | 61.30 | 32.50 | | 32.50 | 91.80 | 56.46 | 24.90 |
| CD49b | 99.70 | 99.80 | 99.50 | 98.00 | 99.80 | 99.60 | 99.40 | 0.70 |
| CD49c | 99.90 | 99.90 | 98.70 | | 99.80 | 99.90 | 99.64 | 0.53 |
| *CD49d* | 97.00 | 78.40 | | 80.60 | 71.00 | 96.00 | 84.60 | 11.44 |
| CD49e | 99.80 | 99.80 | 97.40 | | 99.80 | 99.70 | 99.30 | 1.06 |
| CD50 | 15.70 | 11.40 | 5.70 | | 14.20 | 3.95 | 10.19 | 5.17 |
| CD51/61 | 99.90 | 99.80 | 92.80 | | 99.80 | 99.70 | 98.40 | 3.13 |
| CD53 | 5.38 | 5.63 | | | 2.51 | 1.99 | 3.88 | 1.89 |
| CD54 | 96.30 | 95.60 | | 95.80 | 96.20 | 98.70 | 96.52 | 1.25 |
| CD55 | 99.70 | 99.70 | 93.80 | 92.70 | 99.80 | 99.50 | 97.53 | 3.34 |
| *CD56* | 71.80 | 12.80 | | 1.26 | 6.51 | 20.00 | 22.47 | 28.45 |

*FIG. 19B*

Table 11 (continued).

| Marker | CDC Line #1 | CDC Line #2 | CDC Line #3 | CDC Line #4 | CDC Line #5 | CDC Line #6 | Average | Std. Dev. |
|---|---|---|---|---|---|---|---|---|
| *CD57* | 29.50 | 3.57 | | | 1.35 | 1.66 | 9.02 | 13.69 |
| CD58 | 99.90 | 99.80 | 91.00 | 97.10 | 99.90 | 99.70 | 97.90 | 3.55 |
| CD59 | 99.80 | 99.90 | 98.50 | 99.30 | 99.80 | 99.50 | 99.47 | 0.52 |
| CD61 | 99.80 | 99.80 | 95.00 | 98.70 | 99.90 | 99.70 | 98.82 | 1.92 |
| CD62E | 17.10 | 3.89 | 1.39 | | 1.79 | 9.05 | 6.64 | 6.59 |
| CD62L | 5.78 | 4.06 | | | 2.48 | 2.57 | 3.72 | 1.55 |
| CD62P | 18.60 | 13.90 | 1.98 | | 4.33 | 6.48 | 9.06 | 6.96 |
| CD63 | 98.70 | 94.60 | | | 99.10 | 99.50 | 97.98 | 2.27 |
| CD64 | 3.30 | 4.22 | 2.29 | | 15.70 | 1.57 | 5.42 | 5.84 |
| CD66(a.c.d.e) | 9.44 | 29.00 | | | 6.69 | 13.70 | 14.71 | 9.96 |
| *CD66b* | 55.60 | 7.36 | | | 2.96 | 2.61 | 17.13 | 25.74 |
| CD66f | 2.71 | 3.52 | | | 1.32 | 1.89 | 2.36 | 0.96 |
| CD69 | 3.37 | 5.12 | 1.25 | | 2.79 | 4.65 | 3.44 | 1.54 |
| CD70 | 8.11 | 12.60 | 0.88 | | 1.77 | 3.89 | 5.45 | 4.88 |
| *CD71* | 86.80 | 57.70 | 51.70 | | 52.40 | 98.60 | 69.44 | 21.76 |
| *CD72* | 5.51 | 2.34 | | 95.00 | 8.38 | 9.42 | 24.13 | 39.71 |
| CD73 | 99.90 | 99.80 | | | 99.60 | 99.90 | 99.80 | 0.14 |
| CD74 | 15.40 | 2.30 | 1.67 | | 1.24 | 1.79 | 4.48 | 6.12 |
| CD75 | 8.11 | 6.78 | 7.23 | | 2.17 | 4.09 | 5.68 | 2.47 |
| CD77 | 20.00 | 18.20 | | | 17.80 | 6.55 | 15.64 | 6.13 |
| CD79b | 10.20 | 11.20 | | | 2.77 | 2.58 | 6.69 | 4.65 |
| *CD80* | 23.50 | 38.00 | 1.41 | | 10.60 | 13.80 | 17.46 | 13.93 |
| CD81 | 93.50 | 99.80 | 98.70 | | 99.70 | 99.40 | 98.22 | 2.67 |
| CD83 | 3.93 | 7.05 | 2.06 | | 1.24 | 2.75 | 3.41 | 2.26 |
| CD84 | 9.71 | 24.60 | 1.62 | | 1.97 | 2.19 | 8.02 | 9.87 |
| *CD85* | 29.30 | 12.20 | | 0.39 | 1.19 | 48.30 | 18.28 | 20.44 |
| CD86 | 3.07 | 0.54 | 1.48 | 1.09 | 3.79 | 7.42 | 2.90 | 2.53 |
| *CD87* | 52.00 | 2.96 | 0.97 | | 58.90 | 40.20 | 31.01 | 27.35 |
| CD88 | 3.08 | 0.54 | 0.61 | 0.98 | 2.54 | 1.32 | 1.51 | 1.06 |
| CD89 | 2.62 | 0.61 | | 1.60 | 2.79 | 2.08 | 1.94 | 0.88 |
| *CD90* | 86.70 | 83.40 | | 58.50 | 30.70 | 97.70 | 71.40 | 26.89 |
| CD91 | 53.80 | 49.40 | 49.60 | | 47.40 | 70.00 | 54.04 | 9.22 |
| CDw93 | 4.83 | 4.71 | 1.20 | 0.72 | 15.50 | 3.42 | 5.06 | 5.40 |
| CD94 | 2.02 | 0.69 | 0.69 | 0.85 | 3.71 | 1.65 | 1.60 | 1.17 |

*FIG. 19C*

Table 11 (continued).

| Marker | CDC Line #1 | CDC Line #2 | CDC Line #3 | CDC Line #4 | CDC Line #5 | CDC Line #6 | Average | Std. Dev. |
|---|---|---|---|---|---|---|---|---|
| CD95 | 99.80 | 97.60 | 99.60 | 65.60 | 99.80 | 99.70 | 93.68 | 13.78 |
| *CD97* | 27.90 | 18.30 | 17.60 | 22.50 | 44.50 | 86.80 | 36.27 | 26.65 |
| CD98 | 99.80 | 99.80 | 99.30 | 99.10 | 99.90 | 99.80 | 99.62 | 0.33 |
| CD99 | 99.50 | 97.10 | 99.30 | 99.00 | 99.40 | 99.00 | 98.88 | 0.90 |
| *CD99R* | 57.30 | 6.09 | 88.90 | 73.40 | 73.30 | 44.60 | 57.27 | 29.32 |
| CD100 | 3.61 | 0.60 | 1.27 |  | 2.71 | 1.27 | 1.89 | 1.23 |
| CD102 | 7.56 | 7.71 | 25.10 |  | 27.30 | 14.60 | 16.45 | 9.37 |
| CD103 | 1.97 | 0.34 |  |  | 1.61 | 1.06 | 1.24 | 0.71 |
| CD105 | 99.70 | 99.80 |  | 98.60 | 99.80 | 99.70 | 99.52 | 0.52 |
| CD106 | 4.20 | 4.09 | 2.85 | 2.92 | 2.62 | 14.90 | 5.26 | 4.77 |
| CD107a | 29.10 | 27.80 |  |  | 31.40 | 25.40 | 28.43 | 2.51 |
| CD107b | 5.45 | 11.20 | 20.90 | 8.99 | 17.00 | 8.18 | 11.95 | 5.85 |
| *CD108* | 95.20 | 94.90 | 79.70 | 4.26 | 98.10 | 92.00 | 77.36 | 36.39 |
| *CD109* | 39.70 | 47.60 | 14.90 | 1.08 | 20.80 | 58.10 | 30.36 | 21.64 |
| CD112 | 10.20 | 6.41 | 16.80 | 3.52 | 27.50 | 19.10 | 13.92 | 8.92 |
| CD114 | 2.20 | 0.53 | 1.46 | 0.80 | 2.72 | 1.24 | 1.49 | 0.83 |
| CD116 | 2.30 | 0.56 | 1.48 | 0.98 | 3.41 | 2.54 | 1.88 | 1.06 |
| CD117 | 2.80 | 0.76 | 2.49 |  | 3.53 | 1.44 | 2.20 | 1.10 |
| CD118 (LIF rcptr) | 3.62 | 6.22 | 4.95 | 1.96 | 3.74 | 2.10 | 3.77 | 1.64 |
| *CD119* | 50.80 | 8.11 |  | 11.60 | 59.40 | 62.10 | 38.40 | 26.42 |
| CD120a | 15.20 | 9.61 |  |  | 15.20 | 21.20 | 15.30 | 4.73 |
| CD121a | 12.20 | 7.78 | 3.57 | 2.31 | 3.98 | 7.84 | 6.28 | 3.69 |
| CD121b | 3.40 | 1.37 | 1.04 | 2.11 | 3.98 | 1.51 | 2.24 | 1.19 |
| CD122 | 2.82 | 1.97 | 2.02 | 1.48 | 3.40 | 2.94 | 2.44 | 0.73 |
| CD123 | 2.32 | 0.63 | 0.91 | 0.96 | 2.49 | 0.71 | 1.34 | 0.84 |
| CD124 | 5.41 | 2.62 | 1.93 | 1.22 | 1.64 | 0.00 | 2.14 | 1.82 |
| CD126 | 1.52 | 0.60 | 0.77 | 1.10 | 2.61 | 1.05 | 1.28 | 0.73 |
| CD127 | 2.15 | 0.66 | 1.27 | 1.15 | 2.19 | 1.48 | 1.48 | 0.60 |
| CD128b | 2.37 | 0.49 | 0.58 | 1.03 | 3.04 | 1.03 | 1.42 | 1.04 |
| *CD130* | 86.90 | 19.90 | 54.10 |  | 92.70 | 76.50 | 66.02 | 29.69 |
| CD134 | 2.64 | 1.43 | 1.15 | 1.17 | 3.47 | 1.46 | 1.89 | 0.95 |
| CD135 | 2.10 | 0.46 |  | 2.13 | 1.89 | 1.16 | 1.55 | 0.72 |
| CD137 | 3.43 | 1.97 |  | 1.02 | 3.18 | 9.72 | 3.86 | 3.41 |

*FIG. 19D*

Table 11 (continued).

| Marker | CDC Line #1 | CDC Line #2 | CDC Line #3 | CDC Line #4 | CDC Line #5 | CDC Line #6 | Average | Std. Dev. |
|---|---|---|---|---|---|---|---|---|
| CD137L | 4.18 | 2.21 | 2.87 | 1.36 | 3.73 | 3.08 | 2.91 | 1.02 |
| CD138 | 3.63 | 2.19 | 1.80 | 1.48 | 4.11 | 2.48 | 2.62 | 1.04 |
| *CD140a* | 45.30 | 20.80 | 28.30 |  | 59.10 | 75.00 | 45.70 | 22.14 |
| *CD140b* | 2.76 | 3.56 | 45.60 | 0.89 | 3.20 | 2.54 | 9.76 | 17.58 |
| *CD141* | 52.60 | 58.80 | 29.50 |  | 42.80 | 59.00 | 48.54 | 12.52 |
| *CD142* | 60.90 | 69.00 | 52.50 | 16.70 | 47.80 | 91.00 | 56.32 | 24.66 |
| CD144 | 14.40 | 16.40 | 13.00 | 7.55 | 29.30 | 22.80 | 17.24 | 7.71 |
| *CD146* |  | 46.60 | 77.90 | 14.10 | 46.90 | 54.60 | 48.02 | 22.86 |
| CD147 | 99.70 | 99.90 | 98.80 | 95.00 | 99.70 | 99.20 | 98.72 | 1.86 |
| CD150 | 3.06 | 0.66 | 1.53 | 1.04 | 3.74 | 1.25 | 1.88 | 1.23 |
| CD151 | 99.90 | 99.80 |  | 99.10 | 99.70 | 99.40 | 99.58 | 0.33 |
| CD152 | 8.69 | 5.14 |  | 4.63 | 8.39 | 14.40 | 8.25 | 3.90 |
| CD153 | 5.66 | 7.41 | 6.61 | 7.04 | 3.66 | 2.98 | 5.56 | 1.84 |
| CD154 | 3.77 | 2.06 | 1.43 | 1.86 | 4.81 | 1.47 | 2.57 | 1.40 |
| CD158a | 1.09 | 0.41 | 0.56 |  | 2.01 | 0.70 | 0.95 | 0.64 |
| CD158b | 2.32 | 0.81 | 0.67 | 1.34 | 2.39 | 1.37 | 1.48 | 0.73 |
| CD161 | 1.40 | 0.48 | 0.84 | 0.97 | 1.33 | 1.05 | 1.01 | 0.34 |
| CD162 | 3.80 | 1.49 | 1.00 | 1.24 | 3.64 | 2.00 | 2.19 | 1.23 |
| CD163 | 2.44 | 0.54 | 1.06 | 0.63 | 2.61 | 0.80 | 1.35 | 0.93 |
| *CD164* | 59.40 | 35.40 | 73.70 | 42.20 | 72.90 | 83.20 | 61.13 | 19.01 |
| *CD165* | 99.40 | 62.10 | 98.50 | 90.80 | 99.50 | 98.80 | 91.52 | 14.79 |
| CD166 | 99.70 | 99.70 | 99.50 | 98.30 | 99.80 | 99.20 | 99.37 | 0.56 |
| CD171 | 2.94 | 9.75 | 4.82 | 1.89 | 10.70 | 5.97 | 6.01 | 3.57 |
| CD172b | 17.50 | 1.51 | 2.83 | 0.86 | 6.80 | 2.98 | 5.41 | 6.27 |
| CD177 | 2.55 | 0.47 | 0.82 | 1.52 | 1.31 | 1.04 | 1.29 | 0.72 |
| CD178 | 2.80 | 0.70 | 0.50 | 1.14 | 3.45 | 1.03 | 1.60 | 1.22 |
| CD180 | 3.94 | 2.57 | 1.42 | 1.71 | 4.54 | 1.87 | 2.68 | 1.28 |
| CD181 | 3.12 | 2.66 | 6.17 | 2.45 | 2.42 | 2.52 | 3.22 | 1.47 |
| CD183 | 3.28 | 3.92 | 4.24 | 2.73 | 5.80 | 2.57 | 3.76 | 1.19 |
| CD184 | 5.29 | 2.28 | 2.30 | 1.67 | 4.43 | 2.49 | 3.08 | 1.43 |
| CD193 | 2.76 | 2.20 | 4.65 |  | 2.62 | 2.45 | 2.94 | 0.98 |
| CD195 | 1.99 | 0.52 | 0.44 | 0.69 | 3.97 | 1.16 | 1.46 | 1.36 |
| CD196 | 2.52 | 3.45 | 3.64 | 1.50 | 3.22 | 5.27 | 3.27 | 1.25 |

*FIG. 19E*

Table 11 (continued).

| Marker | CDC Line #1 | CDC Line #2 | CDC Line #3 | CDC Line #4 | CDC Line #5 | CDC Line #6 | Average | Std. Dev. |
|---|---|---|---|---|---|---|---|---|
| CD197 | 1.72 | 0.60 | 1.10 | 1.34 | 1.45 | 1.30 | 1.25 | 0.38 |
| CD200 | 99.80 | 79.20 | | 95.30 | 89.50 | 96.60 | 92.08 | 8.11 |
| CD205 | 1.35 | 0.63 | 1.08 | 1.41 | 3.41 | 5.05 | 2.16 | 1.71 |
| CD206 | 2.02 | 0.52 | 0.77 | 1.32 | 1.39 | 1.13 | 1.19 | 0.53 |
| CD209 | 10.10 | 12.10 | 10.60 | 6.30 | 5.67 | 3.41 | 8.03 | 3.39 |
| *CD220* | 32.10 | 17.50 | 3.05 | 4.89 | 19.20 | 69.20 | 24.32 | 24.40 |
| *CD221* | 75.70 | 27.10 | 26.60 | 4.16 | 50.40 | 72.10 | 42.68 | 28.29 |
| CD226 | 3.15 | 2.85 | 4.12 | 2.53 | 3.50 | 2.24 | 3.07 | 0.68 |
| *CD227* | 35.10 | 40.40 | 39.90 | 9.37 | 45.90 | 67.50 | 39.70 | 18.72 |
| CD229 | 1.21 | 1.35 | 0.73 | 0.51 | 13.70 | 1.06 | 3.09 | 5.21 |
| CD231 | 2.60 | 0.39 | 1.03 | 0.98 | 4.33 | 1.13 | 1.74 | 1.46 |
| CD235a | 2.02 | 2.81 | 11.40 | 0.26 | 5.19 | 2.55 | 4.04 | 3.94 |
| CD243 (p-glycoProtein) | 2.84 | 1.69 | 5.34 | 0.68 | 2.37 | 3.30 | 2.70 | 1.58 |
| *CD244* | 2.14 | 0.34 | 1.42 | 1.07 | 1.41 | 27.40 | 5.63 | 10.68 |
| CD255 (Tweak) | 11.10 | 2.54 | 3.09 | 1.08 | 3.83 | 22.70 | 7.39 | 8.28 |
| CD268 | 4.52 | 1.64 | 2.20 | | 19.90 | 2.36 | 6.12 | 7.78 |
| CD271 | 5.44 | 5.10 | 4.15 | 1.21 | 4.97 | 3.92 | 4.13 | 1.54 |
| *CD273* | 98.10 | 90.40 | 87.70 | 31.60 | 98.90 | 98.70 | 84.23 | 26.22 |
| *CD274* | 84.30 | 74.20 | 95.10 | | 97.50 | 98.60 | 89.94 | 10.47 |
| CD275 (B7-H2) | 3.89 | 4.82 | 5.14 | 2.47 | 4.77 | 3.62 | 4.12 | 1.00 |
| CD278 | 3.27 | 0.67 | 0.70 | 1.99 | 1.23 | 0.94 | 1.47 | 1.01 |
| CD279 | 0.88 | 2.70 | 0.73 | 0.92 | 0.20 | 2.35 | 1.30 | 0.99 |
| CD282 | 3.11 | 3.07 | 1.05 | 1.35 | 0.18 | 1.26 | 1.67 | 1.18 |
| CD305(LAIR-1) | 0.99 | 3.11 | 1.07 | 1.42 | 0.19 | 2.27 | 1.51 | 1.04 |
| CD309 | 4.30 | 5.27 | 0.60 | 1.23 | 0.46 | 7.08 | 3.16 | 2.78 |
| CD314(NKG2D) | 1.27 | 2.26 | 0.93 | 0.84 | 0.22 | 3.53 | 1.51 | 1.20 |
| *CD321(F11 Rcptr)* | 87.50 | 77.30 | 49.80 | 84.80 | 14.40 | 78.40 | 65.37 | 28.35 |
| CDw327 | 1.36 | 2.63 | 0.87 | 1.60 | 0.16 | 1.93 | 1.43 | 0.85 |
| CDw328 | 1.47 | 3.27 | | | 0.24 | 1.76 | 1.69 | 1.24 |
| CDw329 | 1.48 | 3.99 | | 0.99 | 0.26 | 2.84 | 1.91 | 1.49 |
| CD335(NKP46) | 3.76 | 2.97 | 1.36 | 1.06 | 0.20 | 11.20 | 3.43 | 4.02 |
| CD336 | 1.12 | 3.20 | 1.00 | 0.91 | 0.23 | 4.30 | 1.79 | 1.59 |
| CD337 | 1.42 | 2.87 | 1.45 | 0.64 | 0.30 | 2.26 | 1.49 | 0.96 |
| CD338(ABCG2) | 2.01 | 3.82 | 1.14 | 1.10 | 0.22 | 2.24 | 1.76 | 1.24 |

*FIG. 19F*

Table 11 (continued).

| Marker | CDC Line #1 | CDC Line #2 | CDC Line #3 | CDC Line #4 | CDC Line #5 | CDC Line #6 | Average | Std. Dev. |
|---|---|---|---|---|---|---|---|---|
| *CD340(Her2)* | 83.40 | 89.00 | | 52.90 | 14.60 | 99.10 | 67.80 | 34.37 |
| abTCR | 1.18 | 2.83 | 1.17 | 1.34 | 0.20 | 3.73 | 1.74 | 1.29 |
| *B2-uGlob* | 99.90 | 99.60 | 97.40 | 98.60 | 47.20 | 99.80 | 90.42 | 21.19 |
| BLTR-1 | 2.05 | 3.96 | 1.57 | 0.66 | 0.19 | 3.06 | 1.91 | 1.43 |
| CLIP | 4.02 | 4.04 | 1.85 | | 0.22 | 2.17 | 2.46 | 1.61 |
| CMRF-44 | 1.86 | 4.19 | 1.08 | 0.72 | 0.26 | 6.90 | 2.50 | 2.56 |
| CMRF-56 | 1.25 | 2.89 | | 1.00 | 0.23 | 2.20 | 1.51 | 1.04 |
| *EGF-r* | 99.20 | 93.20 | | | 48.40 | 99.60 | 85.10 | 24.64 |
| Fmlp-r | 1.30 | 3.60 | 1.09 | 0.91 | 0.18 | 3.37 | 1.74 | 1.41 |
| gd TCR | 1.73 | 3.14 | 1.03 | 1.10 | 0.26 | 5.30 | 2.09 | 1.84 |
| *Hem. Prog. Cell* | 7.08 | 5.18 | 0.85 | 0.74 | 0.32 | 36.50 | 8.44 | 14.02 |
| *HLA-A,B,C* | 99.60 | 99.80 | 99.50 | 99.40 | 47.10 | 99.50 | 90.82 | 21.42 |
| *HLA-A2* | 99.70 | 99.50 | 1.07 | 0.84 | 0.16 | 1.83 | 33.85 | 50.93 |
| *HLA-DQ* | 16.60 | 21.60 | 34.00 | 14.70 | 5.30 | 41.40 | 22.27 | 13.28 |
| HLA-DR | 1.28 | 3.34 | 1.54 | 1.04 | 0.15 | 2.12 | 1.58 | 1.08 |
| HLA-DR,DP,DQ | 1.83 | 2.85 | 0.89 | 0.81 | 0.20 | 3.01 | 1.60 | 1.16 |
| Invariant NKT | 2.50 | 2.70 | 1.65 | 0.95 | 0.22 | 1.50 | 1.59 | 0.93 |
| Disialoganglioside GD2 | 2.08 | 3.63 | 1.52 | 0.96 | 0.17 | 2.50 | 1.81 | 1.21 |
| *MIC A/B* | 54.80 | 70.70 | 13.40 | | 27.60 | 56.30 | 44.56 | 23.37 |
| NKB1 | 1.58 | 2.96 | 1.01 | 1.07 | 5.75 | 2.31 | 2.45 | 1.78 |
| SSEA-1 | 4.16 | 10.10 | 2.53 | 1.37 | 3.89 | 7.67 | 4.95 | 3.30 |
| SSEA-4 | 5.56 | 5.67 | 2.78 | 1.13 | 1.95 | 18.10 | 5.87 | 6.28 |
| TRA-1-60 | 1.05 | 2.63 | 0.78 | 1.15 | 0.29 | 1.17 | 1.18 | 0.78 |
| TRA-1-81 | 1.69 | 2.78 | 0.72 | 0.81 | 0.16 | 1.04 | 1.20 | 0.92 |
| Vb 23 | 1.94 | 2.51 | | 0.90 | 0.29 | 2.11 | 1.55 | 0.92 |
| Vb 8 | 1.85 | 3.04 | 1.41 | 0.92 | 0.24 | 4.62 | 2.01 | 1.59 |
| *CD49f* | 61.60 | 42.10 | 57.20 | 13.00 | 7.88 | 73.00 | 42.46 | 26.76 |
| CD104 | 18.40 | 1.56 | 3.19 | | 0.53 | 1.40 | 5.02 | 7.54 |
| CD120b | 1.21 | 2.14 | | | 0.46 | 1.64 | 1.36 | 0.71 |
| CD132 | 0.91 | 3.00 | 1.55 | | 0.39 | 6.18 | 2.41 | 2.33 |
| *CD201* | 67.20 | 49.00 | 80.20 | | 29.40 | 77.60 | 60.68 | 21.36 |
| CD210 | 1.39 | 2.59 | 1.14 | | 0.38 | 2.21 | 1.54 | 0.88 |
| CD212 | 1.64 | 3.27 | 0.96 | | 0.43 | 1.77 | 1.61 | 1.07 |
| *CD267* | 1.05 | 2.24 | 1.28 | | 0.49 | 58.60 | 12.73 | 25.65 |

*FIG. 19G*

Table 11 (continued).

| Marker | CDC Line #1 | CDC Line #2 | CDC Line #3 | CDC Line #4 | CDC Line #5 | CDC Line #6 | Average | Std. Dev. |
|---|---|---|---|---|---|---|---|---|
| CD294 | 1.00 | 2.69 | 1.17 | 1.66 | 0.60 | 3.91 | 1.84 | 1.24 |
| *CD326* | 9.74 | 7.61 | 3.55 | 1.21 | 0.51 | 33.80 | 9.40 | 12.48 |
| *Cutaneous Lymph. Antigen* | 0.82 | 2.16 | 0.97 | 1.71 | 0.52 | 60.20 | 11.06 | 24.08 |
| INT B7 | 0.82 | 2.53 | 1.00 | 0.90 | 0.42 | 2.31 | 1.33 | 0.87 |
| SSEA-3 | 1.11 | 3.02 | 5.65 | 1.48 | 0.48 | 14.90 | 4.44 | 5.45 |

*FIG. 19H*

Table 12. Comparison of CDC Marker Expression Versus EDC Marker Expression

| Marker | Comp #1 | Comp #2 | Comp #5 | Comp #6 | Avg. | Std. Dev. | CDC Min | CDC Max | EDC Min | EDC Max |
|---|---|---|---|---|---|---|---|---|---|---|
| CD1a | -0.49 | 38.53 | 0.88 | 20.60 | 14.88 | 18.48 | 1.15 | 39.60 | 0.39 | 2.56 |
| CD1b | 0.43 | 2.30 | 2.41 | -0.40 | 1.18 | 1.39 | 0.71 | 4.27 | 0.45 | 3.12 |
| CD1d | 8.74 | 1.62 | 0.82 | 53.89 | 16.27 | 25.33 | 0.47 | 55.30 | 0.31 | 7.56 |
| CD2 | 9.34 | 1.73 | 1.45 | 34.07 | 11.65 | 15.39 | 1.13 | 35.30 | 0.48 | 1.58 |
| CD3 | -2.43 | 10.77 | 1.33 | 2.50 | 3.04 | 5.56 | 1.78 | 12.00 | 0.45 | 5.58 |
| CD4 | -0.93 | 2.00 | 0.45 | 0.39 | 0.48 | 1.20 | 0.83 | 3.45 | 0.38 | 3.25 |
| CD4v4 | 2.12 | 5.95 | 3.68 | 1.64 | 3.35 | 1.94 | 2.18 | 8.56 | 0.98 | 4.26 |
| CD5 | -8.76 | 1.42 | 1.17 | 0.06 | -1.53 | -4.86 | 1.25 | 2.72 | 0.31 | 11.10 |
| CD6 | 18.08 | 2.80 | 0.75 | 0.92 | 5.64 | 8.35 | 0.66 | 20.50 | 0.47 | 2.42 |
| CD7 | 0.16 | 3.87 | 1.45 | 0.77 | 1.56 | 1.63 | 1.75 | 4.81 | 0.30 | 2.53 |
| CD8a | 1.58 | 2.41 | 1.05 | 1.78 | 1.70 | 0.56 | 0.75 | 3.43 | 0.36 | 1.85 |
| CD8b | 0.00 | 1.02 | 1.73 | 0.25 | 0.75 | 0.78 | 1.86 | 2.20 | 0.48 | 1.87 |
| CD9 | 0.00 | 0.00 | 0.30 | 0.30 | 0.15 | 0.17 | 96.60 | 99.90 | 99.50 | 99.80 |
| CD10 | 17.30 | 21.00 | 23.60 | 19.30 | 20.30 | 2.67 | 21.50 | 98.00 | 29.30 | 80.70 |
| CD11a | 0.88 | 0.77 | 0.83 | 54.16 | 14.16 | 26.67 | 1.38 | 55.70 | 0.55 | 4.01 |
| CD11b | 3.23 | 1.01 | 0.64 | 0.42 | 1.32 | 1.29 | 1.14 | 4.57 | 0.50 | 1.46 |
| CD11c | 0.64 | 10.42 | 0.80 | 2.06 | 3.48 | 4.67 | 1.04 | 11.40 | 0.25 | 1.52 |
| CD13 | 0.90 | 3.00 | 0.80 | 0.00 | 1.18 | 1.28 | 89.40 | 99.80 | 96.60 | 99.30 |
| CD14 | -0.06 | 8.77 | 1.16 | 4.49 | 3.59 | 3.95 | 2.50 | 10.40 | 1.34 | 5.52 |
| CD15 | 27.57 | 52.93 | 60.12 | 5.77 | 36.60 | 24.85 | 7.97 | 62.90 | 2.20 | 3.67 |
| CD15s | 0.23 | 2.59 | 0.93 | 0.84 | 1.15 | 1.01 | 1.21 | 3.27 | 0.29 | 1.62 |
| CD16 | 1.50 | 2.54 | 0.86 | 0.41 | 1.33 | 0.92 | 0.56 | 3.56 | 0.25 | 2.06 |
| CD18 | 2.23 | 6.23 | 0.86 | 0.49 | 2.45 | 2.63 | 1.36 | 7.17 | 0.50 | 2.00 |
| CD19 | 0.06 | 1.13 | 1.69 | 0.26 | 0.79 | 0.76 | 0.99 | 2.19 | 0.30 | 1.63 |
| CD20 | -0.48 | 1.60 | 2.04 | 26.00 | 7.29 | 12.52 | 2.23 | 27.70 | 0.29 | 2.71 |
| CD21 | 2.61 | 2.47 | 3.06 | 1.15 | 2.32 | 0.82 | 1.05 | 4.49 | 0.33 | 1.88 |
| CD22 | 1.42 | 0.72 | 0.86 | 70.33 | 18.33 | 34.67 | 1.32 | 71.90 | 0.47 | 3.58 |
| CD23 | 3.21 | 9.74 | 0.81 | 0.19 | 3.49 | 4.37 | 1.30 | 11.10 | 0.49 | 1.71 |
| CD24 | -5.59 | 16.06 | 2.77 | 27.10 | 10.09 | 14.43 | 6.98 | 37.60 | 4.21 | 13.70 |
| CD25 | 1.09 | 2.10 | 1.74 | 0.39 | 1.33 | 0.75 | 1.87 | 3.38 | 0.56 | 1.81 |
| CD26 | 0.30 | 0.50 | -0.30 | -0.10 | 0.10 | 0.37 | 98.40 | 99.90 | 99.30 | 99.90 |
| CD27 | 0.76 | 8.86 |  | -0.76 | 2.95 | 5.17 | 1.30 | 10.40 | 1.54 | 3.30 |
| CD28 | 0.66 | 4.06 |  | 0.71 | 1.81 | 1.95 | 1.69 | 5.27 | 1.21 | 2.47 |
| CD29 | -1.80 | -10.70 |  | 1.60 | -3.63 | -6.35 | 84.10 | 99.70 | 95.80 | 99.60 |

*FIG. 20A*

Table 12 (continued).

| Marker | Comp #1 | Comp #2 | Comp #5 | Comp #6 | Avg. | Std. Dev. | CDC Min | CDC Max | EDC Min | EDC Max |
|---|---|---|---|---|---|---|---|---|---|---|
| CD30 | 0.80 | 1.73 | | 0.98 | 1.17 | 0.49 | 1.06 | 18.00 | 4.78 | 17.20 |
| CD31 | 41.80 | 26.40 | | 29.50 | 32.57 | 8.15 | 12.70 | 67.40 | 19.90 | 25.60 |
| CD32 | -0.13 | 1.44 | | 8.10 | 3.14 | 4.37 | 0.86 | 9.44 | 1.34 | 2.64 |
| CD33 | 0.97 | 0.90 | | 1.07 | 0.98 | 0.09 | 0.96 | 2.97 | 1.44 | 2.00 |
| CD34 | -17.50 | 10.50 | | 51.70 | 14.90 | 34.81 | 11.10 | 77.10 | 25.40 | 28.60 |
| CD35 | 3.34 | 2.38 | | 0.27 | 2.00 | 1.57 | 1.68 | 5.13 | 1.27 | 1.79 |
| CD36 | -0.26 | 5.16 | | 2.27 | 2.39 | 2.71 | 2.03 | 7.18 | 2.02 | 3.76 |
| CD37 | 0.48 | 1.64 | | 0.24 | 0.79 | 0.75 | 1.09 | 2.75 | 1.11 | 2.10 |
| CD38 | 4.30 | 14.43 | | 1.02 | 6.58 | 6.99 | 1.99 | 16.00 | 1.57 | 5.29 |
| CD39 | 3.25 | 3.66 | | 43.91 | 16.94 | 23.36 | 1.51 | 48.80 | 1.50 | 4.89 |
| CD40 | -6.50 | -2.31 | | 1.40 | -2.47 | -3.95 | 1.21 | 17.40 | 10.60 | 23.60 |
| CD41a | 18.51 | 8.41 | | -4.74 | 7.39 | 11.66 | 1.28 | 20.80 | 1.09 | 6.71 |
| CD41b | 2.25 | 8.05 | | -1.11 | 3.06 | 4.63 | 0.80 | 9.10 | 1.05 | 3.35 |
| CD42a | 0.72 | 10.60 | 3.01 | -3.49 | 2.71 | 5.91 | 2.61 | 15.20 | 1.40 | 6.10 |
| CD42b | -0.53 | 1.97 | 1.97 | 5.38 | 2.20 | 2.43 | 1.07 | 8.38 | 0.12 | 4.34 |
| CD43 | 1.45 | 2.16 | 1.80 | 1.46 | 1.72 | 0.34 | 2.18 | 3.88 | 0.38 | 2.06 |
| CD44 | -0.20 | 0.90 | -0.20 | -0.50 | 0.00 | 0.00 | 90.30 | 99.70 | 98.80 | 99.90 |
| CD45 | -2.45 | 4.39 | 1.40 | 0.31 | 0.91 | 2.83 | 1.88 | 5.58 | 0.73 | 2.45 |
| CD45RA | 2.07 | 5.05 | 1.00 | 1.27 | 2.35 | 1.86 | 1.53 | 7.79 | 1.14 | 3.65 |
| CD45RB | -1.92 | 3.72 | -4.71 | 0.22 | -0.67 | -3.56 | 1.24 | 5.08 | 1.36 | 6.37 |
| CD45RO | 1.71 | 3.97 | 1.20 | -2.97 | 0.98 | 2.89 | 1.92 | 6.01 | 1.40 | 6.05 |
| CD46 | -0.30 | 0.70 | -0.40 | -0.10 | -0.02 | -0.50 | 96.50 | 99.80 | 99.10 | 99.80 |
| CD47 | -0.20 | -0.50 | 0.00 | 0.30 | -0.10 | -0.34 | 91.80 | 99.90 | 99.60 | 99.80 |
| CD48 | 64.84 | 2.27 | | -9.91 | 19.07 | 40.11 | 1.99 | 67.70 | 1.57 | 11.90 |
| CD49a | -7.70 | 46.20 | | 8.10 | 15.53 | 27.71 | 32.50 | 91.80 | 15.10 | 83.70 |
| CD49b | -0.10 | 0.30 | | -0.10 | 0.03 | 0.23 | 98.00 | 99.80 | 99.50 | 99.80 |
| CD49c | 0.10 | 0.00 | | 0.00 | 0.03 | 0.06 | 98.70 | 99.90 | 99.80 | 99.90 |
| CD49d | 10.90 | 7.60 | | 22.50 | 13.67 | 7.83 | 71.00 | 97.00 | 70.80 | 86.10 |
| CD49e | -0.10 | 1.40 | | -0.20 | 0.37 | 0.90 | 97.40 | 99.80 | 98.40 | 99.90 |
| CD50 | 9.92 | 8.94 | | 0.86 | 6.57 | 4.97 | 3.95 | 15.70 | 2.46 | 5.78 |
| CD51/61 | 0.00 | 0.70 | | 0.40 | 0.37 | 0.35 | 92.80 | 99.90 | 99.10 | 99.90 |
| CD53 | 2.64 | 3.58 | | -4.17 | 0.68 | 4.23 | 1.99 | 5.63 | 2.05 | 6.16 |
| CD54 | -2.70 | 2.40 | | -0.20 | -0.17 | -2.55 | 95.60 | 98.70 | 93.20 | 99.00 |
| CD55 | 0.20 | 1.00 | | 0.40 | 0.53 | 0.42 | 92.70 | 99.80 | 98.70 | 99.50 |
| CD56 | 27.40 | -3.60 | | -1.30 | 7.50 | 17.27 | 1.26 | 71.80 | 16.40 | 44.40 |

*FIG. 20B*

Table 12 (continued).

| Marker | Comp #1 | Comp #2 | Comp #5 | Comp #6 | Avg. | Std. Dev. | CDC Min | CDC Max | EDC Min | EDC Max |
|---|---|---|---|---|---|---|---|---|---|---|
| CD57 | 27.01 | 2.18 | | -25.34 | 1.28 | 26.19 | 1.35 | 29.50 | 1.39 | 27.00 |
| CD58 | 0.40 | 0.20 | | -0.20 | 0.13 | 0.31 | 91.00 | 99.90 | 99.50 | 99.90 |
| CD59 | 0.10 | 0.50 | | -0.20 | 0.13 | 0.35 | 98.50 | 99.90 | 99.40 | 99.70 |
| CD61 | 0.00 | -0.10 | | -0.20 | -0.10 | -0.10 | 95.00 | 99.90 | 99.80 | 99.90 |
| CD62E | 10.81 | -1.10 | | 5.67 | 5.13 | 5.97 | 1.39 | 17.10 | 3.38 | 6.29 |
| CD62L | 2.51 | 2.08 | | -1.93 | 0.89 | 2.45 | 2.48 | 5.78 | 1.98 | 4.50 |
| CD62P | 8.40 | 10.39 | | 2.91 | 7.23 | 3.87 | 1.98 | 18.60 | 3.51 | 10.20 |
| CD63 | -0.80 | -1.30 | | 2.00 | -0.03 | -1.78 | 94.60 | 99.50 | 95.90 | 99.50 |
| CD64 | 2.63 | 2.13 | | -3.80 | 0.32 | 3.58 | 1.57 | 15.70 | 0.67 | 5.37 |
| CD66(a.c.d.e) | 4.71 | 24.52 | | -15.70 | 4.51 | 20.11 | 6.69 | 29.00 | 4.48 | 29.40 |
| CD66b | 53.06 | 5.51 | | -4.12 | 18.15 | 30.61 | 2.61 | 55.60 | 1.85 | 6.73 |
| CD66f | 1.00 | 2.46 | | -3.54 | -0.03 | -3.13 | 1.32 | 3.52 | 1.06 | 5.43 |
| CD69 | -1.45 | 2.15 | | -38.65 | -12.65 | -22.59 | 1.25 | 5.12 | 2.97 | 43.30 |
| CD70 | 3.04 | 11.01 | | -55.91 | -13.95 | -36.55 | 0.88 | 12.60 | 1.59 | 59.80 |
| CD71 | 2.40 | 3.30 | | 36.00 | 13.90 | 19.14 | 51.70 | 98.60 | 54.40 | 84.40 |
| CD72 | -0.19 | -1.56 | | -2.78 | -1.51 | -1.30 | 2.34 | 95.00 | 3.90 | 12.20 |
| CD73 | 0.10 | -0.10 | | 0.30 | 0.10 | 0.20 | 99.60 | 99.90 | 99.60 | 99.90 |
| CD74 | 12.21 | -0.33 | | 0.14 | 4.01 | 7.11 | 1.24 | 15.40 | 1.65 | 3.19 |
| CD75 | 3.62 | 2.07 | | -5.06 | 0.21 | 4.63 | 2.17 | 8.11 | 4.49 | 9.15 |
| CD77 | -0.60 | 5.10 | | -12.85 | -2.78 | -9.17 | 6.55 | 20.00 | 13.10 | 20.60 |
| CD79b | 2.84 | 6.97 | | -5.86 | 1.32 | 6.55 | 2.58 | 11.20 | 4.23 | 8.44 |
| CD80 | 11.30 | 35.12 | | 10.21 | 18.88 | 14.08 | 1.41 | 38.00 | 2.88 | 12.20 |
| CD81 | -5.40 | 0.50 | | -0.50 | -1.80 | -3.16 | 93.50 | 99.80 | 98.90 | 99.90 |
| CD83 | 0.05 | 5.31 | | -12.55 | -2.40 | -9.18 | 1.24 | 7.05 | 1.74 | 15.30 |
| CD84 | 5.80 | 23.33 | | -1.94 | 9.06 | 12.95 | 1.62 | 24.60 | 1.27 | 4.13 |
| CD85 | 24.27 | 11.18 | | 45.22 | 26.89 | 17.17 | 0.39 | 48.30 | 1.02 | 5.03 |
| CD86 | 0.15 | -1.60 | | 5.30 | 1.28 | 3.59 | 0.54 | 7.42 | 2.12 | 2.92 |
| CD87 | 9.60 | -70.14 | | 8.10 | -17.48 | -45.61 | 0.97 | 58.90 | 32.10 | 73.10 |
| CD88 | -0.98 | -1.53 | | -0.23 | -0.91 | -0.65 | 0.54 | 3.08 | 1.55 | 4.06 |
| CD89 | 0.33 | -1.39 | | -0.08 | -0.38 | -0.90 | 0.61 | 2.79 | 2.00 | 2.29 |
| CD90 | -7.50 | -10.20 | | 14.70 | -1.00 | -13.66 | 30.70 | 97.70 | 83.00 | 94.20 |
| CD91 | -16.90 | -28.30 | | -9.00 | -18.07 | -9.70 | 47.40 | 70.00 | 70.70 | 79.00 |
| CDw93 | 2.01 | -4.91 | | -10.58 | -4.49 | -6.31 | 0.72 | 15.50 | 2.82 | 14.00 |
| CD94 | -0.07 | -1.67 | | 0.25 | -0.50 | -1.03 | 0.69 | 3.71 | 1.40 | 2.36 |
| CD95 | 0.00 | -2.30 | | 0.80 | -0.50 | -1.61 | 65.60 | 99.80 | 98.90 | 99.90 |

*FIG. 20C*

Table 12 (continued).

| Marker | Comp #1 | Comp #2 | Comp #5 | Comp #6 | Avg. | Std. Dev. | CDC Min | CDC Max | EDC Min | EDC Max |
|---|---|---|---|---|---|---|---|---|---|---|
| CD97 | -33.10 | -40.40 | | 20.10 | -17.80 | -33.02 | 17.60 | 86.80 | 58.70 | 66.70 |
| CD98 | 0.00 | 0.20 | | -0.10 | 0.03 | 0.15 | 99.10 | 99.90 | 99.60 | 99.90 |
| CD99 | 0.20 | -2.50 | | -0.80 | -1.03 | -1.37 | 97.10 | 99.50 | 99.30 | 99.80 |
| CD99R | 3.40 | -58.31 | | -15.70 | -23.54 | -31.59 | 6.09 | 88.90 | 53.90 | 64.40 |
| CD100 | 1.28 | -1.58 | | -0.22 | -0.17 | -1.43 | 0.60 | 3.61 | 1.49 | 2.33 |
| CD102 | -11.54 | -32.19 | | 0.80 | -14.31 | -16.67 | 7.56 | 27.30 | 13.80 | 39.90 |
| CD103 | 0.60 | -1.50 | | -0.24 | -0.38 | -1.06 | 0.34 | 1.97 | 1.30 | 1.84 |
| CD105 | 0.20 | 0.00 | | 0.20 | 0.13 | 0.12 | 98.60 | 99.80 | 99.50 | 99.80 |
| CD106 | -8.50 | -7.61 | | 1.10 | -5.00 | -5.30 | 2.62 | 14.90 | 11.70 | 13.80 |
| CD107a | -46.30 | -37.30 | | -0.10 | -27.90 | -24.49 | 25.40 | 31.40 | 25.50 | 75.40 |
| CD107b | -16.25 | -3.80 | | -5.52 | -8.52 | -6.75 | 5.45 | 20.90 | 13.70 | 21.70 |
| CD108 | 12.10 | -2.50 | | -0.80 | 2.93 | 7.98 | 4.26 | 98.10 | 83.10 | 97.40 |
| CD109 | 11.20 | -25.60 | | 14.10 | -0.10 | -22.13 | 1.08 | 58.10 | 28.50 | 73.20 |
| CD112 | -5.50 | -26.59 | | 6.50 | -8.53 | -16.75 | 3.52 | 27.50 | 12.60 | 33.00 |
| CD114 | -0.50 | -1.24 | | -0.52 | -0.75 | -0.42 | 0.53 | 2.72 | 1.76 | 2.70 |
| CD116 | -0.57 | -2.37 | | -0.51 | -1.15 | -1.06 | 0.56 | 3.41 | 2.87 | 3.05 |
| CD117 | 0.15 | -2.13 | | -0.43 | -0.80 | -1.19 | 0.76 | 3.53 | 1.87 | 2.89 |
| CD118 (LIF rcptr) | -5.22 | 2.50 | | -0.92 | -1.21 | -3.87 | 1.96 | 6.22 | 3.02 | 8.84 |
| CD119 | -7.00 | -71.89 | | 5.60 | -24.43 | -41.58 | 8.11 | 62.10 | 56.50 | 80.00 |
| CD120a | -11.80 | -29.79 | | -1.90 | -14.50 | -14.14 | 9.61 | 21.20 | 23.10 | 39.40 |
| CD121a | -0.50 | 7.78 | | -8.76 | -0.49 | -8.27 | 2.31 | 12.20 | 0.00 | 16.60 |
| CD121b | 0.19 | -3.18 | | -0.70 | -1.23 | -1.75 | 1.04 | 3.98 | 2.21 | 4.55 |
| CD122 | -0.24 | -1.74 | | -0.45 | -0.81 | -0.81 | 1.48 | 3.40 | 3.06 | 3.71 |
| CD123 | 0.25 | -3.64 | | -0.61 | -1.33 | -2.04 | 0.63 | 2.49 | 1.32 | 4.27 |
| CD124 | -3.77 | -5.51 | | -6.25 | -5.18 | -1.27 | 0.00 | 5.41 | 6.25 | 9.18 |
| CD126 | -0.71 | -1.56 | | 0.30 | -0.66 | -0.93 | 0.60 | 2.61 | 0.75 | 2.23 |
| CD127 | 0.04 | -1.24 | | -0.32 | -0.51 | -0.66 | 0.66 | 2.19 | 1.80 | 2.11 |
| CD128b | -0.05 | -1.96 | | -0.61 | -0.87 | -0.98 | 0.49 | 3.04 | 1.64 | 2.44 |
| CD130 | 3.70 | -74.00 | | -1.60 | -23.97 | -43.41 | 19.90 | 92.70 | 78.10 | 93.90 |
| CD134 | -10.76 | -2.27 | | -0.99 | -4.67 | -5.31 | 1.15 | 3.47 | 2.45 | 13.40 |
| CD135 | 0.56 | -1.95 | | -0.41 | -0.60 | -1.27 | 0.46 | 2.13 | 1.54 | 2.41 |
| CD137 | -3.29 | -9.33 | | 0.25 | -4.12 | -4.84 | 1.02 | 9.72 | 6.72 | 11.30 |
| CD137L | 0.43 | -2.47 | | -1.55 | -1.20 | -1.48 | 1.36 | 4.18 | 3.75 | 4.68 |
| CD138 | 0.74 | -5.07 | | 0.00 | -1.44 | -3.16 | 1.48 | 4.11 | 2.48 | 7.26 |

*FIG. 20D*

Table 12 (continued).

| Marker | Comp #1 | Comp #2 | Comp #5 | Comp #6 | Avg. | Std. Dev. | CDC Min | CDC Max | EDC Min | EDC Max |
|---|---|---|---|---|---|---|---|---|---|---|
| CD140a | -3.50 | -62.30 | | 0.80 | -21.67 | -35.26 | 20.80 | 75.00 | 48.80 | 83.10 |
| CD140b | 0.38 | -5.07 | | -13.06 | -5.92 | -6.76 | 0.89 | 45.60 | 2.38 | 15.60 |
| CD141 | -24.90 | -26.90 | | -12.50 | -21.43 | -7.80 | 29.50 | 59.00 | 71.50 | 85.70 |
| CD142 | -28.70 | -22.20 | | -0.90 | -17.27 | -14.54 | 16.70 | 91.00 | 89.60 | 91.90 |
| CD144 | 4.10 | -2.80 | | 17.34 | 6.21 | 10.23 | 7.55 | 29.30 | 5.46 | 19.20 |
| CD146 | -64.50 | -43.60 | | -13.40 | -40.50 | -25.69 | 14.10 | 77.90 | 64.50 | 90.20 |
| CD147 | 0.10 | 0.40 | | -0.50 | 0.00 | 0.46 | 95.00 | 99.90 | 99.50 | 99.70 |
| CD150 | -18.94 | -4.40 | | -1.01 | -8.12 | -9.53 | 0.66 | 3.74 | 2.26 | 22.00 |
| CD151 | 0.30 | 0.50 | | -0.30 | 0.17 | 0.42 | 99.10 | 99.90 | 99.30 | 99.70 |
| CD152 | -21.41 | -27.26 | | 6.04 | -14.21 | -17.78 | 4.63 | 14.40 | 8.36 | 32.40 |
| CD153 | 1.51 | 1.85 | | -6.81 | -1.15 | -4.90 | 2.98 | 7.41 | 4.15 | 9.79 |
| CD154 | 1.63 | -5.22 | | -1.44 | -1.68 | -3.43 | 1.43 | 4.81 | 2.14 | 7.28 |
| CD158a | -0.13 | -1.74 | | -0.91 | -0.93 | -0.81 | 0.41 | 2.01 | 1.22 | 2.15 |
| CD158b | -0.21 | -25.79 | | -0.80 | -8.93 | -14.60 | 0.67 | 2.39 | 2.17 | 26.60 |
| CD161 | -0.50 | -1.91 | | -0.20 | -0.87 | -0.91 | 0.48 | 1.40 | 1.25 | 2.39 |
| CD162 | 0.81 | -3.25 | | 0.55 | -0.63 | -2.27 | 1.00 | 3.80 | 1.45 | 4.74 |
| CD163 | 0.94 | -1.67 | | -1.09 | -0.61 | -1.37 | 0.54 | 2.61 | 1.50 | 2.21 |
| CD164 | -21.60 | -45.70 | | 29.70 | -12.53 | -38.51 | 35.40 | 83.20 | 53.50 | 81.10 |
| CD165 | 4.00 | -37.30 | | 0.10 | -11.07 | -22.80 | 62.10 | 99.50 | 95.40 | 99.40 |
| CD166 | 0.00 | -0.10 | | -0.50 | -0.20 | -0.26 | 98.30 | 99.80 | 99.70 | 99.80 |
| CD171 | -2.13 | -14.65 | | 3.08 | -4.57 | -9.11 | 1.89 | 10.70 | 2.89 | 24.40 |
| CD172b | 10.61 | -18.59 | | -0.29 | -2.76 | -14.76 | 0.86 | 17.50 | 3.27 | 20.10 |
| CD177 | 0.53 | -7.29 | | -0.22 | -2.33 | -4.32 | 0.47 | 2.55 | 1.26 | 7.76 |
| CD178 | 1.05 | -10.40 | | -1.40 | -3.58 | -6.03 | 0.50 | 3.45 | 1.75 | 11.10 |
| CD180 | 0.86 | -1.47 | | -1.44 | -0.68 | -1.34 | 1.42 | 4.54 | 3.08 | 4.04 |
| CD181 | -0.29 | -6.83 | | -1.57 | -2.90 | -3.47 | 2.42 | 6.17 | 3.41 | 9.49 |
| CD183 | -1.98 | -2.72 | | -1.91 | -2.20 | -0.45 | 2.57 | 5.80 | 4.48 | 6.64 |
| CD184 | 1.27 | -3.96 | | 0.17 | -0.84 | -2.76 | 1.67 | 5.29 | 2.32 | 6.24 |
| CD193 | 0.70 | -0.29 | | -0.27 | 0.05 | 0.57 | 2.20 | 4.65 | 2.06 | 2.72 |
| CD195 | -1.21 | -3.10 | | -0.60 | -1.64 | -1.31 | 0.44 | 3.97 | 1.76 | 3.62 |
| CD196 | -0.80 | 0.91 | | 1.44 | 0.52 | 1.17 | 1.50 | 5.27 | 2.54 | 3.83 |
| CD197 | -1.35 | -1.55 | | -2.15 | -1.68 | -0.42 | 0.60 | 1.72 | 2.15 | 3.45 |
| CD200 | 1.10 | -13.00 | | 0.90 | -3.67 | -8.08 | 79.20 | 99.80 | 92.20 | 98.70 |
| CD205 | -3.31 | -3.91 | | 0.41 | -2.27 | -2.34 | 0.63 | 5.05 | 4.54 | 4.66 |
| CD206 | 0.35 | -5.94 | | -0.03 | -1.87 | -3.53 | 0.52 | 2.02 | 1.16 | 6.46 |

*FIG. 20E*

Table 12 (continued).

| Marker | Comp #1 | Comp #2 | Comp #5 | Comp #6 | Avg. | Std. Dev. | CDC Min | CDC Max | EDC Min | EDC Max |
|---|---|---|---|---|---|---|---|---|---|---|
| CD209 | 4.89 | -2.20 | | -10.99 | -2.77 | -7.96 | 3.41 | 12.10 | 5.21 | 14.40 |
| CD220 | -21.20 | -29.50 | | 1.40 | -16.43 | -15.99 | 3.05 | 69.20 | 47.00 | 67.80 |
| CD221 | -11.90 | -34.50 | | 4.70 | -13.90 | -19.68 | 4.16 | 75.70 | 61.60 | 87.60 |
| CD226 | -0.39 | -4.95 | | -2.19 | -2.51 | -2.30 | 2.24 | 4.12 | 3.54 | 7.80 |
| CD227 | -36.40 | -40.50 | | -13.10 | -30.00 | -14.78 | 9.37 | 67.50 | 71.50 | 80.90 |
| CD229 | -0.34 | -0.56 | | -0.57 | -0.49 | -0.13 | 0.51 | 13.70 | 1.55 | 1.91 |
| CD231 | -9.40 | -2.50 | | -0.62 | -4.17 | -4.62 | 0.39 | 4.33 | 1.75 | 12.00 |
| CD235a | -3.01 | -0.37 | | -0.32 | -1.23 | -1.54 | 0.26 | 11.40 | 2.87 | 5.03 |
| CD243 (p-glycoProtein) | 0.13 | -1.58 | | -2.68 | -1.38 | -1.42 | 0.68 | 5.34 | 2.71 | 5.98 |
| CD244 | 0.83 | -3.45 | | 25.31 | 7.56 | 15.52 | 0.34 | 27.40 | 1.31 | 3.79 |
| CD255 (Tweak) | 9.24 | -5.87 | | 17.92 | 7.10 | 12.04 | 1.08 | 22.70 | 1.86 | 8.41 |
| CD268 | 2.11 | -27.96 | | 1.25 | -8.20 | -17.12 | 1.64 | 19.90 | 1.11 | 29.60 |
| CD271 | -7.56 | -31.60 | | -1.72 | -13.63 | -15.84 | 1.21 | 5.44 | 5.64 | 36.70 |
| CD273 | 9.00 | 60.00 | | 9.40 | 26.13 | 29.33 | 31.60 | 98.90 | 30.40 | 89.30 |
| CD274 | -13.10 | -21.70 | | 6.20 | -9.53 | -14.29 | 74.20 | 98.60 | 92.40 | 97.40 |
| CD275 (B7-H2) | -1.81 | -0.32 | | -3.45 | -1.86 | -1.57 | 2.47 | 5.14 | 5.14 | 7.07 |
| CD278 | 0.08 | -1.71 | | 0.28 | -0.45 | -1.09 | 0.67 | 3.27 | 0.66 | 3.19 |
| CD279 | -3.79 | 1.25 | | 0.90 | -0.55 | -2.82 | 0.20 | 2.70 | 1.45 | 4.67 |
| CD282 | -0.12 | 2.05 | | 0.20 | 0.71 | 1.17 | 0.18 | 3.11 | 1.02 | 3.23 |
| CD305(LAIR-1) | -2.73 | 1.86 | | 1.01 | 0.05 | 2.44 | 0.19 | 3.11 | 1.25 | 3.72 |
| CD309 | -10.90 | 0.52 | | 5.49 | -1.63 | -8.40 | 0.46 | 7.08 | 1.59 | 15.20 |
| CD314(NKG2D) | -2.42 | 0.66 | | 2.13 | 0.12 | 2.32 | 0.22 | 3.53 | 1.40 | 3.69 |
| CD321(F11 Rcptr) | -4.10 | 18.10 | | 23.70 | 12.57 | 14.70 | 14.40 | 87.50 | 54.70 | 91.60 |
| CDw327 | -2.92 | 1.20 | | 0.68 | -0.35 | -2.24 | 0.16 | 2.63 | 1.25 | 4.28 |
| CDw328 | -2.70 | 0.95 | | -0.07 | -0.61 | -1.88 | 0.24 | 3.27 | 1.83 | 4.17 |
| CDw329 | -2.32 | 2.02 | | 0.45 | 0.05 | 2.20 | 0.26 | 3.99 | 1.97 | 3.80 |
| CD335(NKP46) | 0.14 | 1.52 | | 9.08 | 3.58 | 4.81 | 0.20 | 11.20 | 1.45 | 3.62 |
| CD336 | -2.51 | 1.92 | | 2.91 | 0.77 | 2.89 | 0.23 | 4.30 | 1.28 | 3.63 |
| CD337 | -2.90 | 0.51 | | -2.09 | -1.49 | -1.78 | 0.30 | 2.87 | 2.36 | 4.35 |
| CD338(ABCG2) | -13.69 | 0.94 | | -0.67 | -4.47 | -8.02 | 0.22 | 3.82 | 2.88 | 15.70 |

*FIG. 20F*

Table 12 (continued).

| Marker | Comp #1 | Comp #2 | Comp #5 | Comp #6 | Avg. | Std. Dev. | CDC Min | CDC Max | EDC Min | EDC Max |
|---|---|---|---|---|---|---|---|---|---|---|
| CD340(Her2) | -15.40 | -9.60 |  | 4.00 | -7.00 | -9.96 | 14.60 | 99.10 | 95.10 | 98.80 |
| abTCR | -3.01 | 0.14 |  | 0.36 | -0.84 | -1.89 | 0.20 | 3.73 | 2.69 | 4.19 |
| B2-uGlob | 0.60 | 0.50 |  | 0.40 | 0.50 | 0.10 | 47.20 | 99.90 | 99.10 | 99.40 |
| BLTR-1 | -2.98 | 1.68 |  | 0.35 | -0.32 | -2.40 | 0.19 | 3.96 | 2.28 | 5.03 |
| CLIP | -1.29 | 1.95 |  | 0.11 | 0.26 | 1.62 | 0.22 | 4.04 | 2.06 | 5.31 |
| CMRF-44 | -7.80 | -0.56 |  | 4.05 | -1.44 | -5.97 | 0.26 | 6.90 | 2.85 | 9.66 |
| CMRF-56 | -3.78 | 0.12 |  | -0.06 | -1.24 | -2.20 | 0.23 | 2.89 | 2.26 | 5.03 |
| EGF-r | 0.40 | -6.00 |  | 0.00 | -1.87 | -3.59 | 48.40 | 99.60 | 98.80 | 99.60 |
| Fmlp-r | -3.47 | 1.79 |  | 0.90 | -0.26 | -2.82 | 0.18 | 3.60 | 1.81 | 4.77 |
| gd TCR | -2.88 | 1.24 |  | 2.89 | 0.42 | 2.97 | 0.26 | 5.30 | 1.90 | 4.61 |
| Hem. Prog. Cell | -37.02 | -10.12 |  | -2.00 | -16.38 | -18.33 | 0.32 | 36.50 | 15.30 | 44.10 |
| HLA-A,B,C | 0.00 | 0.50 |  | -0.30 | 0.07 | 0.40 | 47.10 | 99.80 | 99.30 | 99.80 |
| HLA-A2 | 0.30 | 0.10 |  | 0.22 | 0.21 | 0.10 | 0.16 | 99.70 | 1.61 | 99.40 |
| HLA-DQ | -38.00 | -8.70 |  | 16.60 | -10.03 | -27.32 | 5.30 | 41.40 | 24.80 | 54.60 |
| HLA-DR | -3.24 | 1.69 |  | 0.32 | -0.41 | -2.54 | 0.15 | 3.34 | 1.65 | 4.52 |
| HLA-DR,DP,DQ | -3.70 | 0.34 |  | 0.23 | -1.04 | -2.30 | 0.20 | 3.01 | 2.51 | 5.53 |
| Invariant NKT | -1.92 | 1.23 |  | -0.13 | -0.27 | -1.58 | 0.22 | 2.70 | 1.47 | 4.42 |
| Disialogangliosid e GD2 | -8.42 | 1.35 |  | 0.32 | -2.25 | -5.37 | 0.17 | 3.63 | 2.18 | 10.50 |
| MIC A/B | -18.20 | -24.40 |  | 37.90 | -1.57 | -34.32 | 13.40 | 70.70 | 18.40 | 95.10 |
| NKB1 | -2.16 | 1.11 |  | 0.43 | -0.21 | -1.73 | 1.01 | 5.75 | 1.85 | 3.74 |
| SSEA-1 | -18.54 | -9.50 |  | 1.08 | -8.99 | -9.82 | 1.37 | 10.10 | 6.59 | 22.70 |
| SSEA-4 | -46.84 | -26.43 |  | -12.00 | -28.42 | -17.51 | 1.13 | 18.10 | 30.10 | 52.40 |
| TRA-1-60 | -1.71 | 1.54 |  | -0.07 | -0.08 | -1.63 | 0.29 | 2.63 | 1.09 | 2.76 |
| TRA-1-81 | -0.91 | 1.49 | -0.10 | -0.24 | 0.06 | 1.02 | 0.16 | 2.78 | 0.26 | 2.60 |
| Vb 23 | -2.10 | -0.09 | -0.55 | -0.43 | -0.79 | -0.89 | 0.29 | 2.51 | 0.84 | 4.04 |
| Vb 8 | -2.41 | 0.85 | -0.55 | 2.52 | 0.10 | 2.09 | 0.24 | 4.62 | 0.79 | 4.26 |
| CD49f | -7.80 | -11.70 | 7.88 | 29.30 | 4.42 | 18.62 | 7.88 | 73.00 | 0.00 | 69.40 |
| CD104 | 15.84 | 0.04 | -0.02 | 0.19 | 4.01 | 7.89 | 0.53 | 18.40 | 0.55 | 2.56 |
| CD120b | -2.36 | 0.36 | -0.12 | 0.48 | -0.41 | -1.33 | 0.46 | 2.14 | 0.58 | 3.57 |

*FIG. 20G*

Table 12 (continued).

| Marker | Comp #1 | Comp #2 | Comp #5 | Comp #6 | Avg. | Std. Dev. | CDC Min | CDC Max | EDC Min | EDC Max |
|---|---|---|---|---|---|---|---|---|---|---|
| CD132 | -2.58 | 1.23 | -0.41 | 5.12 | 0.84 | 3.25 | 0.39 | 6.18 | 0.80 | 3.49 |
| CD201 | 8.30 | -16.90 | -26.00 | 7.10 | -6.88 | -17.24 | 29.40 | 80.20 | 55.40 | 70.50 |
| CD210 | -2.97 | 0.97 | -0.20 | 0.41 | -0.45 | -1.75 | 0.38 | 2.59 | 0.57 | 4.36 |
| CD212 | -1.98 | 1.98 | -0.18 | 0.61 | 0.11 | 1.65 | 0.43 | 3.27 | 0.61 | 3.62 |
| CD267 | -3.05 | 0.95 | -0.09 | 57.49 | 13.83 | 29.16 | 0.49 | 58.60 | 0.57 | 4.10 |
| CD294 | -3.37 | 1.35 | -0.43 | 2.87 | 0.10 | 2.68 | 0.60 | 3.91 | 1.03 | 4.37 |
| CD326 | -34.86 | -9.09 | -22.69 | 23.40 | -10.81 | -25.12 | 0.51 | 33.80 | 10.40 | 44.60 |
| Cutaneous Lymph. Antigen | -67.58 | -23.64 | -20.48 | 36.60 | -18.78 | -42.72 | 0.52 | 60.20 | 21.00 | 68.40 |
| INT B7 | -2.91 | 1.16 | -0.03 | 1.17 | -0.15 | -1.92 | 0.42 | 2.53 | 0.45 | 3.73 |
| SSEA-3 | -14.39 | -21.28 | -27.02 | -1.90 | -16.15 | -10.81 | 0.48 | 14.90 | 15.50 | 27.50 |

*FIG. 20H*

OPTIMIZED METHODS FOR GENERATION OF CARDIAC STEM CELLS FROM CARDIAC TISSUE AND THEIR USE IN CARDIAC THERAPY

RELATED CASES

This application is a continuation application of U.S. application Ser. No. 14/403,078, filed on Jan. 23, 2015, which is the U.S. National Phase entry under 35 U.S.C. § 371 of International Application No. PCT/US2013/043772, filed on May 31, 2013, which claims the benefit of U.S. Provisional Application No. 61/655,928, filed on Jun. 5, 2012, the entire disclosure of which is incorporated by reference herein.

STATEMENT REGARDING FEDERALLY SPONSORED R&D

This work was funded, at least in part, by grants from the National Institutes of Health, NHLBI RC3 Grant No. HL103356 and NHLBI SBIR Grant No. HL095203, awarded to Capricor, Inc. The government may have certain rights in the inventions disclosed herein.

BACKGROUND

Field

The present application relates generally to methods and compositions for generating stem cells for the repair or regeneration of damaged cells or tissue. For example, in several embodiments the methods and compositions disclosed herein may be used for the repair and/or regeneration of cardiac tissue. In particular, the methods disclosed herein relate to methods for scaling up the processing of tissue samples, for example cardiac tissue, and culturing of the processed tissue to generate a quantity of cardiac stem cells from the tissue sufficient for use in treatment of one or more subjects in need of cardiac tissue repair.

Description of the Related Art

The scope of human disease that involves loss of or damage to cells is vast and includes, but is not limited to neurodegenerative disease, endocrine diseases, cancers, and cardiovascular disease. For example, coronary heart disease is presently the leading cause of death in the United States, taking more than 650,000 lives annually. According to the American Heart Association, 1.2 million people suffer from a heart attack (or myocardial infarction, MI) every year in America. Of those who survive a first MI, many (25% of men and 38% of women survivors) will still die within one year of the MI. Currently, 16 million Americans are MI survivors or suffer from angina (chest pain due to coronary heart disease). Coronary heart disease can deteriorate into heart failure for many patients. 5 million Americans are currently suffering from heart failure, with 550,000 new diagnoses each year. Regardless of the etiology of their conditions, many of those suffering from coronary heart disease or heart failure have suffered permanent heart tissue damage, which often leads to a reduced quality of life.

SUMMARY

In view of the need for ready to use cardiac stem cells for repair or regeneration of diseased or damaged cardiac tissue, there are provided for herein methods for preparing cardiosphere derived cells (CDCs) suitable for allogeneic cardiac stem cell therapy, comprising receiving donor cardiac tissue from a subject, processing the piece of donor cardiac tissue into a plurality of tissue explants, enzymatically digesting the explants, culturing the explants area until cells migrate from the explant, collecting the cells that migrate from the explant; culturing the collected cells in order to generate CDCs; harvesting the CDCs; filtering the harvested CDCs to remove particles greater than about 50 µm, thereby generating CDCs suitable for allogeneic cardiac stem cell therapy.

In several embodiments, there is also provided methodology for preparing filtered CDCs for allogeneic cell therapy comprising processing donor cardiac tissue from a subject into a plurality of tissue explants, partially enzymatically digesting said explants, culturing said explants until cells migrate from said explant, collecting the cells that migrate from the explant, culturing the collected cells in order to generate CDCs, harvesting the CDCs, and filtering said harvested CDCs to remove particles greater than about 50 µm in diameter to isolate CDCs less than about 50 µm in diameter to facilitate allogeneic cardiac stem cell therapy. In particular, in several embodiments, the filtered CDCs with particles greater than 50 µm in diameter removed are suitable for intracoronary delivery and passage into cardiac arterioles having an inner diameter of about 50 µm, which advantageously reduces the risks of adverse side effects associated with CDC administration, such as, for example, arrhythmia, vascular blockage, therapy-induced ischemia, and the like.

In several embodiments, the processing of donor cardiac tissue involves transferring the explants from a digestion (and/or dissection) vessel to a culture vessel by flooding the explant with culture media rather than hand-placing (including automated placing) the explant in the culture vessel. Advantageously, in several embodiments, transfer by flooding the explant with media not only reduces risk of contamination, but also reduces perturbation of the explant, and thereby improves one or more of the yield of cells from the explant, potency of the CDCs derived from the explant, and reduction of time to generate CDCs from the explant.

In several embodiments, the plurality of explants comprises a plurality of explants obtained from a single region of the donor cardiac tissue (e.g., each of the plurality of explants are derived from, for example, the atria). In contrast, in several embodiments, the plurality of explants comprises explants obtained from more than one region of the donor cardiac tissue. In some embodiments, the mixture of explants obtained from various regions improves the yield, potency and/or growth of the CDCs, as the explants are exposed to a cytokine and/or signaling mileu in culture that more closely resembles the in vivo environment. For example, explants from the atria co-cultured with explants from the septum may chemically interact (e.g., cytokine, chemokine, or paracrine factor cross-talk or signaling) more so than explants from more separated regions of the heart. However, in several embodiments, explants from distinct regions of the heart are readily co-cultured with one another.

In several embodiments, the cells that arise from the explant may clump as they migrate off the explant. In some embodiments, the clumping reduces the ultimate yield or quality of the CDCs, and thus, in some embodiments, an anti-clumping agent is utilized. For example, in some embodiments, heparin is used to supplement the explant culture media to reduce cell clumping. In some embodiments, the explant culture media is supplemented with L-glutamine in order to reduce clumping of cells migrating from said explant. Combinations of heparin and L-glutamine (and/or other agents) are used in some embodiments. Manual disaggregation of cell clumps is also employed in several embodiments. However, in several embodiments, additional steps or agents to reduce cell clumping are not utilized.

In several embodiments, the tissue explants are processed into a size ranging from about 100 µm³ to about 800 µm³, including about 100 µm³ to about 700 µm³, about 200 µm³ to about 600 µm³, about 100 µm³ to about 600 µm³, about 200 µm³ to about 500 µm³, about 200 µm³ to about 400 µm³, about 300 µm³ to about 500 µm³, about 300 µm³ to about 400 µm³, and overlapping ranges thereof. In several embodiments, the processing is fully automated. In some embodiments, manual processing, or manual and automated processing are used in combination. In some embodiments, the donor tissue is optionally frozen prior to processing. In some embodiments, other treatments (e.g., saline perfusions or oxygenated Krebs solution) are employed prior to, during, or after the processing. In several embodiments, size of the explant is determined by one or more of age, health, disease status of the donor and/or time since harvest of the donor tissue. In several embodiments, the explants range from about 0.1 to about 0.9 grams, including about 0.1 to about 0.8 grams, about 0.1 to about 0.7 grams, about 0.1 to about 0.6 grams, about 0.2 to about 0.6 grams, about 0.3 to about 0.6 grams, about 0.3 to about 0.5 grams, about 0.3 to about 0.4 grams, and overlapping ranges thereof. Depending on the embodiment greater or lesser masses may be used. The mass of the tissue is also determined in some embodiments, in part, by the region of the heart from which it is collected. In several embodiments, the explants are processed to be cuboidal in shape, though in some embodiments other shapes or approximations of shapes are used. Thus, in several embodiments, the combination of size and tissue mass is used to determine the overall dimensions of the explants for a particular donor tissue (or region of donor tissue). In several embodiments, the overall dimensions are based on the number of explants to be cultured in a given production run and/or within a given culture vessel (e.g., explant density). In several embodiments, the overall dimensions are based on the region (or regions) of the heart from which the explants were derived.

In some embodiments, tissue explants are digested for a time ranging from about 30 seconds to about 5 minutes, including about 30 seconds to about 4 minutes, about 30 seconds to about 3 minutes, about 30 seconds to about 2 minutes, about 30 seconds to about 1 minutes, about 30 seconds to about 90 seconds, about 30 seconds to about 120 seconds, about 30 seconds to about 200 seconds, about 30 seconds to about 250 seconds, and overlapping ranges thereof. Similar to the determination of the overall size and mass of the donor tissue, enzymatic digestion can be tailored (by enzyme choice, enzyme concentration, and/or digestion time) based on the parameters that provide optimal tissue digestion and viability of resultant cells. For example, in some embodiments, if a larger explant is used, a longer digestion time may be used to ensure that the enzyme reaches the central portions of the explant. In some embodiments, enzymatic digestion is optionally eliminated. In several embodiments, digestion is complete (e.g., the fragment is completely dispersed into cells), while in some embodiments the digestion is partial (e.g., portions of the explant remain intact).

In several embodiments, the explants are cultured at a density of about 1 explant per 400 to 700 cm² culturing surface, including about 1 explant per 400 cm², about 1 explant per 450 cm², about 1 explant per 500 cm², about 1 explant per 550 cm², about 1 explant per 600 cm², about 1 explant per 650 cm², and overlapping densities therebetween. In some embodiments, more than one explant is cultured within a single culture vessel. In some embodiments, a plurality of explants are cultured, separated (e.g., divided) within a single vessel, such that the cells from one explant do not interact directly with cells from another explant. In some embodiments, the cells cannot interact, but the various regions of the culture vessel are in fluid communication with one another, thereby allowing, for example, paracrine interaction between the various explants and their respective cells.

In several embodiments, the methods further comprise freezing the CDCs suitable for allogeneic cardiac stem cell therapy. In some embodiments, the culturing process is tailored to end prior to generation of CDCs (e.g., at the cardiosphere stage). Thus the cardiospheres may, in some embodiments, also be stored, and later used to generate CDCs.

In several embodiments, the donor cardiac tissue ranges in size from about 1 gram to about 300 grams, including about 1 to about 20 grams, about 20 to about 50 grams, about 50 to about 75 grams, about 75 to about 150 grams, about 150 to about 200 grams, about 200 to about 250 grams, about 250 to about 300 grams, and overlapping ranges thereof. In some embodiments, a whole heart is used. In some such embodiments, a portion of the heart may be processed at a first time, and the remainder processed at a later time. For example, in some embodiments, a portion of tissue is processed and used to generate CDCs while the remainder of the tissue is optionally frozen between processing stages. However, in some embodiments, the remainder of the tissue is stored in cold cardioplegia (or its functional equivalent). In several embodiments, the donor cardiac tissue is processed within about 3 days from removal from the subject, though in some embodiments (e.g., frozen or hypothermic storage conditions) longer times are still suitable for generation of cells. In several embodiments, the tissue samples can be frozen for about 1 to about 90 days prior to being processed, including about 1 to about 4 days, about 4 to about 7 days, about 7 to about 10 days, about 10 to about 14 days, about 14 to about 28 days, about 28 to about 36 days, about 36 to about 48 days, about 48 to about 60 days, about 60 to about 75 days, about 75 to about 90 days, and overlapping times of frozen storage therebetween.

In several embodiments, the filtering comprises filtering the harvested CDCs through a first filter to remove particles greater in size than about 140 µm and through a second filter to remove particles greater than about 50 µm. While in some embodiments, the filters may be separate devices, in some embodiments, the first and the second filter comprise a single two-stage filter device. In several embodiments, multiple passes through one or more filters are performed to account for filtration efficiencies less than 100%.

In several embodiments, the CDCs suitable for allogeneic cardiac stem cell therapy comprise less than 1% particles greater than 150 µm. In several embodiments, the CDCs suitable for allogeneic cardiac stem cell therapy comprise essentially 0% particles greater than 150 µm. In several embodiments, the CDCs suitable for allogeneic cardiac stem cell therapy also comprise less than 1% particles greater than 50 µm. As a result of the sizes of particles (and cells) in the cellular composition resulting from the claimed methods, the CDCs suitable for allogeneic cardiac stem cell therapy are suitable for intracoronary delivery. Because virtually none of the components of the resultant cellular composition are greater than 150 μm, the composition can freely flow through a coronary artery (diameter on average of 150-170 μm). Moreover, the very small proportion of components of the resultant cellular composition that are greater than 50 μm reduces the risk of adverse events (e.g., arrhythmias) due to reduction of blood or oxygen flow through the cardiac arterioles.

In several embodiments, the methods further comprise cryogenically storing cells until such time as they are to be administered to a subject. In several embodiments, in contrast, the methods further comprise directly delivering said isolated CDCs to a subject. In several embodiments, the delivery is via intracoronary delivery, though as discussed herein, other routes are optionally used (e.g., intravenous, direct injection, etc.).

There is also provided herein a method for preparing cardiac stem cells suitable for allogeneic cardiac stem cell therapy, comprising receiving donor cardiac tissue from a first subject, processing the piece of donor cardiac tissue into a plurality of cuboidal tissue explants ranging from about 0.3 to about 0.6 grams, culturing the explants at a density of about 1 explant per 400 to 700 cm$^2$ culturing surface area until cells migrate from the explant, collecting the cells that migrate from the explant, culturing the collected cells in order to generate cardiac stem cells; harvesting the cardiac stem cells, and filtering the harvested cardiac stem cells to remove particles greater than about 50 μm, thereby generating cardiac stem cells suitable for allogeneic cardiac stem cell therapy.

There is also provided herein a composition comprising CDCs produced by any of the methods disclosed herein. There is also provided for herein isolated CDCs suitable for allogeneic cardiac stem cell therapy comprising, a plurality of CDCs generated from donor cardiac tissue from a first subject, less than 1% particles greater than 140 μm in size, less than 1% particles greater than 50 μm in size, wherein the composition is suitable for administration to a subject via an intracoronary delivery route.

In several embodiments, the composition comprises a substantially pure population of CDCs. In several embodiments, the composition comprises a substantially uniformly sized population of CDCs, wherein greater than about 90%, greater than about 95%, greater than about 98%, greater than about 99%, or about 100% of all CDCs are less than 40 μm.

Additionally provided for herein is a composition comprising a population of CDCs suitable for allogeneic cardiac stem cell therapy, comprising a plurality of CDCs generated from donor cardiac tissue from a first subject, wherein at least about 70% of said CDCs express one or more of CD9, CD13, CD26, CD29, CD44, CD46, CD49b, CD49c, CD49d, CD49e, CD51/61, CD54, CD55, CD58, CD59, CD61, CD63, CD73, CD81, CD95, CD98, CD99, CD105, CD147, CD151, CD165, CD166, CD200, CD273, CD274, beta 2 microglobulin, epidermal growth factor receptor, and Human leukocyte antigen A,B,C. In several embodiments, at least about 80% of the CDCs express one or more of the listed markers. In several embodiments, at least about 90% of the CDCs express one or more of the listed markers. In several embodiments, at least about 95% of the CDCs express one or more of the listed markers. In several embodiments, at least about 97% of the CDCs express one or more of the listed markers. In several embodiments, at least about 99% of the CDCs express one or more of the listed markers. In several embodiments, the entire population expresses at least one of the markers. In several embodiments, the population of CDCs is distinguishable from other cells (e.g., other stem cells and/or other intermediate cells produced during the methods disclosed herein) by virtue of the various markers expressed (and/or the level of expression). Thus, in several embodiments, the marker profile of CDCs can be used to specifically identify a cell as a CDC (or not a CDC), determine the purity of a CDC preparation, and/or identify variability (and potential sources of that variability, be they donor-to-donor variations, production-to-production variation, etc.) between CDC production runs.

In several embodiments, there is also provided a composition comprising CDCs suitable for allogeneic cardiac stem cell therapy comprising a plurality of CDCs generated from donor cardiac tissue from a first subject, less than about 1% particles greater than about 140 μm in size, less than about 1% particles greater than about 50 μm in size, and wherein at least about 70% of said CDCs express one or more of CD9, CD13, CD26, CD29, CD44, CD46, CD49b, CD49c, CD49d, CD49e, CD51/61, CD54, CD55, CD58, CD59, CD61, CD63, CD73, CD81, CD95, CD98, CD99, CD105, CD147, CD151, CD165, CD166, CD200, CD273, CD274, beta 2 microglobulin, epidermal growth factor receptor, and Human leukocyte antigen A,B,C. In several embodiments, at least about 80% of the CDCs express one or more of the listed markers. In several embodiments, at least about 90% of the CDCs express one or more of the listed markers. In several embodiments, at least about 95% of the CDCs express one or more of the listed markers. In several embodiments, at least about 97% of the CDCs express one or more of the listed markers. In several embodiments, at least about 99% of the CDCs express one or more of the listed markers. In several embodiments, the entire population expresses at least one of the markers.

In some embodiments, between about 20 percent and about 80 percent of the CDCs express one or more of CD10, CD15, CD31, CD34, CD49a, CD56, CD71, CD72, CD87, CD90, CD91, CD97, CD99R, CD107a, CD108, CD109, CD119, CD130, CD140a, CD141, CD142, CD164, CD220, CD221, CD227, CD321, CD340, Human leukocyte antigen A2, Human leukocyte antigen DQ, MIC A/B, CD49f, and CD201.

In several embodiments, the CDC compositions are produced by processing donor cardiac tissue into a plurality of tissue explants, and culturing the explants until cells migrate from said explant, thereby generated explant-derived cells (EDCs), which can be further processed to generate CDCs. In several embodiments, at least about 70% of said EDCs express one or more of CD9, CD13, CD26, CD29, CD44, CD46, CD47, CD49b, CD49c, CD49e, CD51/61, CD54, CD55, CD58, CD59, CD61, CD63, CD73, CD81, CD90, CD95, CD98, CD99, CD105, CD108, CD130, CD142, CD147, CD151, CD165, CD166, CD200, CD274, CD340, beta 2 microglobulin, epidermal growth factor receptor, and Human leukocyte antigen A,B,C. In several embodiments, at least about 80% of the EDCs express one or more of the listed markers. In several embodiments, at least about 90% of the EDCs express one or more of the listed markers. In several embodiments, at least about 95% of the EDCs express one or more of the listed markers. In several embodiments, at least about 97% of the EDCs express one or more of the listed markers. In several embodiments, at least about 99% of the EDCs express one or more of the listed markers. In several embodiments, the entire EDC population expresses at least one of the markers.

In several embodiments, the marker profile of the EDCs is consistent with the marker profile of the resultant CDCs. However, in several embodiments, the marker profile may vary, in that one or more markers present on EDCs may exhibit increased or decreased expression on CDCs. In several embodiments, the differences in marker expression allow a CDC population to be distinguished from its precursor EDC population. In several embodiments, the ability to distinguish is advantageous because the purity of the CDCs can be verified. Thus, in several embodiments, the CDC populations can be identified as comprising less than about 30%, less than about 20%, less than about 15%, less than about 5%, or less than about 1% EDCs. Additionally, in several embodiments, CDCs can be distinguished from EDC by detecting a reduction in expression of one or more of SSEA-4, CD141, and CD227 by said CDCs as compared to said EDCs.

In several embodiments, marker profiles of the EDCs can be used as a predictor of the viability and/or therapeutic potency of the resultant CDC population. In several embodiments, for example the presence of a particular marker profile on the EDCs can be correlated with CDCs that have suitable clinical efficacy. Thus, in several embodiments, profiling the EDCs can be used as a screening step to determine if the production of CDCs from a particular tissue source (e.g., production may be deemed to be worthwhile to continue if the CDCs are predicted to be therapeutically efficacious) should continue. Depending on the embodiments and the variable being assessed, the screening is used to identify potential discrepancies in expression between the EDCs and CDCs (e.g., those markers known to decrease or increase) or similarities between the EDCs and the CDCs (e.g., presence of certain marker on the EDC will result in presence of that marker in similar quantities on the CDC, thus indicating that the CDC will, or will not, have a desired characteristic).

BRIEF DESCRIPTION OF THE DRAWINGS

FIGS. 6A-6C depict donor differences in allogeneic CDC yields. A) Amount of CDCs grown from each donor over time. B) Growth rate of CDCs per gram of tissue per day for each donor. Comparison of groups using t test: *p<0.05 vs DCD. C) Master cell bank creation and total CDC yields for each donor. Total yields are extrapolated from data collected while expanding part of the MCB.

FIGS. 12A-12J depict the average expression levels of 242 cell surface markers on EDCs from four separate production runs.

FIGS. 18A-18H depict Table 10, entitled, "EDC Cell Surface Marker Expression by EDC Line and Average." Table 10 spans across FIGS. 18A-18H.

FIGS. 19A-19H depict Table 11, entitled, "CDC Cell Surface Marker Expression by CDC Line and Average." Table 11 spans across FIGS. 19A-19H.

FIGS. 20A-20H depict Table 12, entitled, "Comparison of CDC Marker Expression Versus EDC Marker Expression." Table 12 spans across FIGS. 20A-20H.

DETAILED DESCRIPTION

Figure 1:
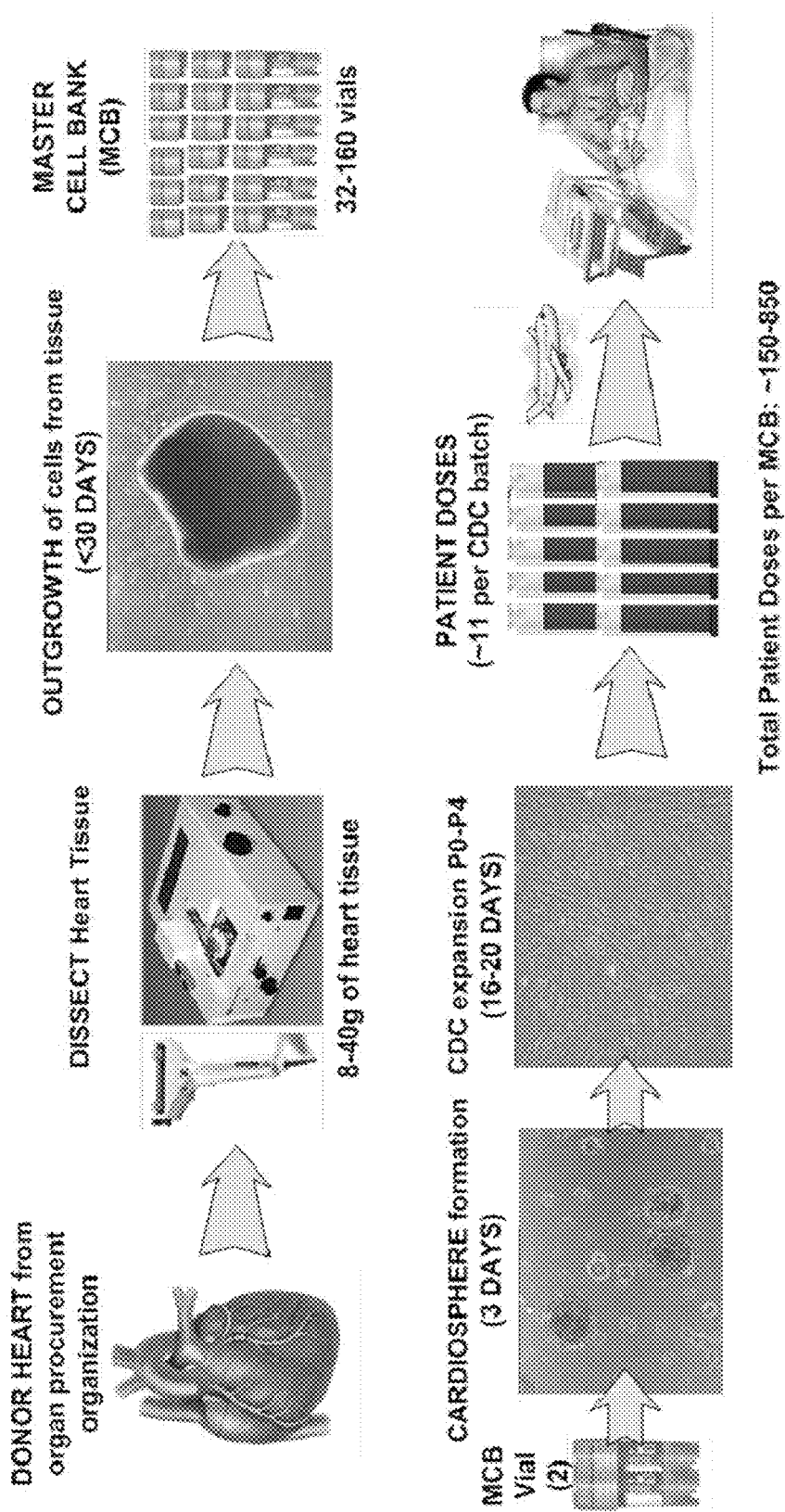
FIG. 1 depicts a schematic process flow for the generation of a master cell bank from a donor heart, from which cardiospheres and/or cardiosphere-derived cells (CDCs) are produced.

Cell therapy, the introduction of new cells into a tissue in order to treat a disease, represents a promising new method for repairing or replacing diseased tissue with healthy tissue. In several embodiments, there are disclosed various methods of preparing tissue for harvesting and expansion of resident stem cells from the tissue. In several embodiments, the methods disclosed herein allow the generation of a greatly expanded quantity of cells from a relatively small mass of starting material, thereby allowing creation of a "master cell bank". In several embodiments, this master cell bank serves as a repository for stem cells that can be used in treating a plurality of patients in need of cardiac stem cell therapy.

Cardiac Stem Cell Therapy

There are provided herein optimized methods for production of stem cells to be used for administration to subject having damaged or diseased cardiac tissue in order to repair, regenerate, and/or improve the anatomy and/or function of the damaged or diseased cardiac tissue. While multiple types of stem cells may be processed according to the methods disclosed herein, in several embodiments, cardiac stem cells are generated by processing cardiac tissue.

Multiple types of cardiac stem cells can be obtained according to the methods disclosed herein, including but not limited to cardiospheres and cardiosphere-derived cells (CDCs). Additional information regarding cardiospheres and CDCs, may be found, for example, in U.S. Pat. No. 8,268,619, issued Sep. 18, 2012, and U.S. patent application Ser. No. 11/666,685, filed Apr. 21, 2007; and U.S. Ser. No. 13/412,051, filed Mar. 5, 2012, the entireties of each of which are incorporated by reference herein.

Cardiac several embodiments herein is used, in several embodiments, to treat or repair damaged or diseased cardiac tissue that results from one or more of acute heart failure (e.g., a stroke or MI) or chronic heart failure (e.g., congestive heart failure). In several embodiments, about $1\times10^5$ to about $1\times10^7$ of cardiac stem cells are administered. In several embodiments, the dose is varied depending on the size and/or age of a subject receiving the cells. In some embodiments smaller numbers or larger numbers of cells are optionally administered. Different routes of administration are also used, depending on the embodiment. For example, the cardiac stem cells may be administered by intravenous, intra-arterial, intracoronary, or intramyocardial routes (or other routes) of administration.

Cardiac stem cell therapy (and the methods disclosed herein) may be autologous, allogeneic, syngeneic, or xenogeneic, depending on the embodiment. In several embodiments, allogeneic therapy is employed, as the ready availability of tissue sources (e.g., organ donors, etc.) enables a scaled-up production of a large quantity of cells that can be stored and subsequently used in an "off the shelf" fashion.

Interestingly, the potential for ready scale-up when using an allogeneic tissue source presents a variety of technical challenges, which are discussed in more detail and addressed by the methods disclosed herein.

Issues to Address During Scale-Up of Cardiac Tissue Preparation

Similar to scaling-up a lab protocol or cooking recipe, scale-up of tissue processing and culturing to generate cardiac stem cells for therapeutic use is not achieved simply by 'doubling' or increasing batch size. One challenge is the ability to process, in a timely fashion, the potentially larger donor tissue sample size that is obtained in the context of allogeneic cardiac stem cell therapy. While autologous cell therapy typically employs a one or more endomyocardial biopsy samples (a total tissue mass of ~0.27 g), allogeneic tissue sources can easily range from between about 8 to about 40 grams (if not larger, for example with an entire donor heart). Processing this amount of tissue requires improved efficiencies of scale and time, in order to utilize as much of the tissue as possible before the tissue becomes unsuitable for use.

Another issue to address in large-scale cardiac stem cell processing is cell clumping. Because several embodiments of cardiac stem cell therapy employ a vessel-based route of administration (e.g., intracoronary, intravenous, etc.), clumping of cells increase the risk of adverse side effects upon administration. These include, but are not limited to arrhythmia, embolism or blockage of smaller cardiac vasculature.

Consistency of the resultant pool of cardiac stem cells is also an issue, in some embodiments, as multiple different cardiac tissue subtypes (e.g., atria, septum, ventricle) may be received and processed from a single donor sample. Because each of these subtypes of tissues have different characteristics in culture (e.g., growth rate) and, in several embodiments, cells isolated from distinct areas will be pooled to create a master cell bank, the batch to batch characteristics may vary. As discussed below, the methods disclosed herein address the issues above, among others, in order to provide optimized scale-up of cardiac stem cell generation.

Tissue Harvesting and Processing

As discussed above, in several embodiments employing allogeneic donor cardiac tissue, the potentially large amount of tissue obtained may require specific processing methods. While manual processing is often used with endomyocardial biopsies (though automation could be used), in several embodiments manual processing would be insufficient from a temporal perspective to process the larger amount of tissue received. Thus, in several embodiments, automated methods and/or machinery are used to process the received tissue in a more efficient, timely, and cost effective manner. As a result, a better yield is obtained, in several embodiments, based on these methods.

For example, in several embodiments, after receiving donor cardiac tissue and making a gross dissection to produce manageable tissue fragments, an automated dermatome is used in some embodiments, to make an initial cut, for example in the z-axis. In several embodiments, this initial incision is used to cut fragments of cardiac tissue ranging from about 0.2 to about 1.5 g (to be used for a single culture dish). In some embodiments, the initial fragment ranges from about 0.2 to about 0.3 g, about 0.3 to about 0.4 g, about 0.4 to about 0.5, about 0.5 to about 0.6 g, about 0.6 to about 0.8 g, about 0.8 to about 1.0 g, about 1.0 to about 1.2 g, about 1.2 to about 1.5 g, and overlapping ranges thereof. After the initial fragment is generated, cuts in the x-axis and the y-axis are made to generate a cube of tissue (e.g., an explant). In several embodiments, the explant size varies depending on the subtype of tissue, while in other embodiments, a constant explant size is used for the entire donor tissue, regardless of tissue subtype. In some embodiments, the explant ranges from about 100 to about 200 $\mu m^3$, about 200 to about 300 $\mu m^3$, about 300 to about 400 $\mu m^3$, about 400 to about 500 $\mu m^3$, about 500 to about 600 $\mu m^3$, about 600 to about 700 $\mu m^3$, about 700 to about 800 $\mu m^3$, about 800 to about 900 $\mu m^3$, about 900 to about 1000 $\mu m^3$, and overlapping ranges thereof. In some embodiments, the explant size is determined based on the quality of the tissue (e.g., fresh donor tissue versus aged donor tissue). In some embodiments, the explant size is selected to improve the efficiency of downstream steps, including but not limited to enzymatic treatment of the explant (e.g., due to more even penetration of the enzyme into the central portion of the explant).

In several embodiments, the resultant explant is moved from the dissection dish to a culture dish by flooding the explant with culture media and allowing it to come to rest in the culture vessel (as opposed to hand-placement of the explant). Thereafter the explant can be cultured undisturbed for a period of days, and in the interim, additional donor cardiac can be processed in a timely fashion. In some embodiments, the methods disclosed herein enable the use of one or more robotic systems in one or more steps of the process, including, but not limited to, automated flask processing stations. Thus, in some embodiments, human error is reduced, as is, in some embodiments risk of contamination of the culture. The overall scheme for processing and generation of a master cell bank is shown generally in FIG. 1.

Culturing of Tissue Explants

Subsequent to the processing of the donor tissue discussed above, a cardiac tissue explant is cultured undisturbed for a period of days in suitable culture media. In several embodiments, the lack of perturbation allows the explant to adhere to the surface of the culture dish (which in several embodiments is coated with a basement membrane-like material such as, for example, laminin, fibronectin, poly-L-orinthine, or combinations thereof) more effectively, which in turn allows the more rapid and robust generation of cells for harvesting. In several embodiments, the culture flasks are treated such that coatings are not necessary (e.g., the explants can, in some embodiments, be cultured in the absence of fibronectin, etc.).

The tissue explants are cultured until a layer of stromal-like cells arise from the adherent explants. This phase of culturing is further identifiable by small, round, phase-bright cells that migrate over the stromal-cells. In certain embodiments, the explants are cultured until the stromal-like cells grow to confluence. At or before that stage, the phase-bright cells are harvested. In certain embodiments, phase-bright cells are harvested by manual methods, while in others, enzymatic digestion, for example trypsin (or a non-animal derived equivalent enzyme), is used. These harvested cells (which are termed Explant-Derived Cells, or EDCs) can then be used to generate cardiospheres, CDCs, frozen for later generation of cardiospheres or CDCs, or subjected to various quality control analyses. Additional information regarding generation of cardiospheres and CDCs, may be found, for example in U.S. patent application Ser. No. 10/567,008, filed Jul. 13, 2006; Ser. No. 11/666,685, filed Apr. 21, 2007; and Ser. No. 13/412,051, filed Mar. 5, 2012, the entireties of each of which are incorporated by reference herein.

In several embodiments, the size of the culture vessels selected to receive the sized explant is varied. In some embodiments, the surface area of the culture vessel is selected to allow one or more explants to be adhered within a single vessel. In some embodiments, the surface area allotted to an explant ranges from about 200 to about 300 $cm^2$, about 300 to about 400 $cm^2$, about 400 to about 500 $cm^2$, about 500 to about 600 $cm^2$, about 600 to about 700 $cm^2$, about 700 to about 800 $cm^2$, about 800 to about 900 $cm^2$, about 900 to about 1000 $cm^2$, about 1000 to about 1100 $cm^2$, about 1100 to about 1200 $cm^2$, and overlapping ranges thereof. In several embodiments, a range between about 400 $cm^2$ and 450 $cm^2$, about 450 $cm^2$ and 500 $cm^2$, about 500 $cm^2$ and 550 $cm^2$, about 550 $cm^2$ and 600 $cm^2$, about 600 $cm^2$ and 550 $cm^2$, about 650 $cm^2$ and 700 $cm^2$, and overlapping ranges thereof (per explant) is used. In some embodiments, commercial culture vessels are used, while in other embodiments, custom vessels are generated.

In several embodiments, particular surface area dedicated to a single explant allows improved growth of cells from the implant. In some embodiments, this is due to reduced contact inhibition or other type of growth inhibition from cells arising from other explants. In some embodiments, the density of resultant cells enables sufficient cell-cell interaction (contact, paracrine, or otherwise) without overgrowth of the cells. In addition to overall improved yield, this also improves the predictability of cell growth such that cell harvesting can be optimized (e.g., avoiding undergrowth or overgrowth). Utilizing the methods disclosed herein, a large number of cells can be generated from the donor tissue. In several embodiments (as compared to the per gram amount of starting tissue) the number of cells generated as a result of the methods disclosed herein is about $1 \times 10^5$, about $2 \times 10^5$, about $4 \times 10^5$, about $6 \times 10^5$, about $8 \times 10^5$, about $1 \times 10^6$, about $2 \times 10^6$, about $4 \times 10^6$, about $10 \times 10^6$, about $20 \times 10^6$, about $30 \times 10^6$, about $35 \times 10^6$, about $40 \times 10^6$, about $1 \times 10^7$, about $1 \times 10^8$, or greater, depending on the embodiment. Thus the ratio of starting tissue mass, based on the unexpectedly advantageous expansion of clinical quality cells based on the methods herein, to clinical doses is about 1:4, about 1:5, about 1:6 about 1:7, about 1:8, about 1:9, about 1:10, and in some cases about 1:20, or greater. Thus, a starting material mass of about 24 grams of cardiac donor tissue will yield about 30 cryovials of explant derived cells, which is suitable, depending on the dose, for approximately 150 patient therapeutic doses.

In addition to the dedicated surface area allotted to an explant, in several embodiments, the subtypes of cardiac tissue derived from the donor sample are optimized. Certain regions of cardiac tissue exhibit distinct characteristics of growth when subjected to the processing described herein. For example, in several embodiments, atrial explants exhibit a rapid cell growth, such that a culture vessel becomes confluent (ready for harvest) prior to explants from other regions. Interestingly, other regions exhibit different growth patterns. See for example, FIGS. 2A-2B. In some embodiments, the various characteristics of the different regions can be exploited in a single culture format, e.g., the explants from multiple regions can be combined (e.g., cultured together) to allow the synergistic interplay between the explants and cells, thereby resulting, in several embodiments, unexpectedly further enhanced growth (as compared to growth of cells from any region alone). For example, in several embodiments, atrial explants are combined with one or more explants from other cardiac regions, for example the right ventricle, septum, left ventricle, or apex and cultured together. In some embodiments, the ratio of mass of the first region is tailored with respect to the mass of the second region. For example, in some embodiments, the ratio is about 1:1, about 1:2, about 1:3, about 1:4, about 1:5, about 1:6, about 1:10, about 1:20 about 20:1, about 10:1, about 6:1, about 5:1, about 4:1, about 3:1, about 2:1, and other ratios within those listed above. In some embodiments, the amount of a first tissue (e.g., atrial to septal, atrial to ventricular, ventricular to septal, atrial to apex, apex to septal, etc.) is about 5% of the amount of the second subtypes, about 10% of the amount of the second subtype, about 15% of the amount of the second subtype, about 20% of the amount of the second subtype, about 25% of the amount of the second subtype, about 30% of the amount of the second subtype, about 35% of the amount of the second subtype, about 40% of the amount of the second subtype, about 45% of the amount of the second subtype, about 50% of the amount of the second subtype, or overlapping ranges thereof. In some embodiments, other ratios or combinations are used. Selection of the ratio is based, in some embodiments, on the status (e.g., quality and/or amount) of the donor tissue. In several embodiments, there is a synergistic communication between the various cells growing (e.g., contact or paracrine) allowing the unexpected increased overall yield and/or rate of cell generation. In several embodiments, various extracellular matrix proteins deposited by the different cells promote the growth and/or viability of cells from a different tissue subtype. In still additional embodiments, other protein-protein interactions occur between the cell types to benefit the growth of the combination of cells. Moreover, as the master cell bank is, in several embodiments, a combination of cells harvested off of each of a plurality of implants, the combination of two (or more) cardiac tissue subtypes yields a more consistent end stem cell batch.

Post-Culturing Processing

After the harvesting of cells growing off of the explants and generation of cardiospheres or CDCs, several processing steps are employed (either alone or in combination) in order to address the final quality of the stem cells to be used in treating damaged cardiac tissue of a subject. As mentioned above, one side-effect of scaling-up tissue processing and growth can be cell clumping. It is possible that this side effect is due to changes in the conditions experienced by the explants/cells during larger-scale culturing (e.g., more contact with neighboring cells, such as from a higher seeding density). As several embodiments of cardiac repair using stem cells generated with the methods disclosed herein are via the vasculature cell clumping tolerated only to a limited extent, due to the possibility of arrhythmia induction, vessel blockade, etc. Administration via the intracoronary route (diameter of ~150-170 µm) with passage into the cardiac arterioles (diameter of ~40-50 µm) therefore requires particular attention to limiting cell clumps.

In several embodiments, addition of one or more reagents to the culture media reduces the tendency of certain cells to clump or join together. In several embodiments, addition of L-glutamine to the media helps reduce cell clumping. In some embodiments, heparin supplementation reduces cell clumping. Given that the passageways of the cardiac vasculature are tubular in nature, cells that are joined in a linear fashion (e.g., daisy chain) are suitable for use given that in one dimension their size is sufficient to navigate the cardiac vasculature, despite that in another dimension, their size would be too great.

Filtration is also used in several embodiments, to reduce the risk of arrhythmias (or other adverse event). In several embodiments, filtration also functions to reduce the risk of granuloma formation, which can occur when the immune system attempts to wall off substances that it perceives as foreign but is unable to eliminate. However, in several embodiments, maintenance and use of particulate-free culture-ware largely (or completely) obviates the need to filter for purposes of reducing granulomas.

In several embodiments, gross filtration and/or sedimentation are used as a first pass to remove large foreign bodies, cellular clumps and/or explant fragments. In some embodiments, filtration through a particulate filter with a 150 µm pore size reduces the presence of particles greater than about 150 µm (e.g., microscopic foreign bodies). In some embodiments, multiple passes through 150 µm filters are used, in order to account for filtration efficiencies that may be less than 100%. In some embodiments, this filtration results in a resultant cell composition having less than about 5%, less than about 1%, less than about 0.1%, or less than about 0.01% particles greater than 150 µm. In several embodiments, the resultant cell composition comprises greater than about 80%, greater than about 85%, greater than about 90%, greater than about 95%, greater that about 98%, greater than about 99%, or more, of all particles in the cell composition are less than 150 µm. In several embodiments, the composition is substantially free of particles greater than 150 µm. In several embodiments, the composition is pure, in that there are no particles greater than 150 µm. It shall be appreciated that other filter sizes may be used in other embodiments, for example, filters having pore sizes ranging from about 100 to about 110 µm, about 110 to about 120 µm, about 120 to about 125 µm, about 125 to about 130 µm, about 130 to about 135 µm, about 135 to about 140 µm, about 140 to about 145, about 145 µm to about 150 µm, and overlapping ranges thereof. In addition, the term "filter" shall be given its ordinary meaning and shall also refer to any means for separating a first substance from a second substance based on one or more of size, shape, surface features, mass, density and the like. Thus, additional filtration means may also be used, including but not limited to filters, sieves, membranes, mechanical filters, chemical filters, optical filters, biological filters, etc.

To further reduce the risk of arrhythmia or other adverse event, in several embodiments, a further filtration step (or steps) are performed. In some embodiments, filters having a pore diameter of 40 µm are used to filter the cell composition previously filtered at 150 µm. In other embodiments filters of other pore sizes may be used, such as for example, pores ranging from about 20 to about 25 µm, about 25 to about 30 µm, about 30 to about 35 µm, about 35 to about 40 µm, and overlapping ranges thereof. In some embodiments, multiple passes through such secondary filters are used, in order to account for filtration efficiencies that may be less than 100%. In some embodiments, therefore, the resultant cell mixture comprises less than about 5%, less than about 1%, less than about 0.1%, or less than about 0.01% particles greater than 40 µm. In several embodiments, the resultant cell composition comprises greater than about 80%, greater than about 85%, greater than about 90%, greater than about 95%, greater that about 98%, greater than about 99%, or more, of all CDCs are less than about 40 µm. In several embodiments, the composition is substantially free of particles greater than about 40 µm. In several embodiments, the composition is pure, in that there are no particles greater than about 40 µm.

In still additional embodiments, and with the added advantage of reduced sample handling (and the associated reduction in contamination risk) a single filtration is performed using a filter (or filters) having a pore diameter of about 40 µm are used to filter the cell composition. As discussed above, other filters of other pore sizes may be used in some embodiments, such as for example, pores ranging from about 20 to about 25 µm, about 25 to about 30 µm, about 30 to about 35 µm, about 35 to about 40 µm, and overlapping ranges thereof. In some embodiments, multiple passes through such filters are used, in order to account for filtration efficiencies that may be less than 100%. In some embodiments, therefore, the resultant cell mixture comprises less than about 10%, less than about 5%, less than about 1%, less than about 0.1%, or less than about 0.01% particles greater than 40 µm and less than about 5%, less than about 1%, less than about 0.1%, less than about 0.01%, or substantially no particles greater than 150 µm. In several embodiments, the resultant cell composition comprises greater than about 80%, greater than about 85%, greater than about 90%, greater than about 95%, greater than about 98%, greater than about 99%, or more, of all CDCs are less than 40 µm. In several embodiments, the composition is substantially free of particles greater than 40 µm. In several embodiments, the composition is pure, in that there are no particles greater than 40 µm.

It shall also be appreciated that, depending on the embodiment and the quantity of cellular culture that is to be filtered, various filtration mechanisms can be used. Pre-sterilized, disposable filters are used in some embodiments. In other embodiments, a repeatedly sterilizable and reusable filter device is employed. In some embodiments, centrifugal filtration systems are used. In some embodiments, in-line or syringe tip filters are used. In several embodiments, screen filters are used. Concentric filters are used in additional embodiments. Two step (or multistep) filters (e.g., those having more than one filter pore size in sequential filtration regions) are used in some embodiments. Advantageously, in several embodiments, such filters reduce the risk of contamination as, in some embodiments, multistage filters are self-contained. Combinations of filters are also used, in some embodiments.

Thus, in some embodiments, the resultant cell mixture comprises less than 5%, less than 1%, less than 0.1%, or less than 0.01% particles greater than 150 µm and less than 5%, less than 1%, less than 0.1%, or less than 0.01% particles greater than 50 µm. Such embodiments advantageously reduce the risk of arrhythmia generation (or other adverse effects such as granulomas) upon administration to a subject. It shall be appreciated that the sizes above are the size restrictions, in some cases, on a group of cells. In other words, if two CDCs of 20 µm in size are joined or otherwise adherent to one another, the pair of cells will still pass the filtration, as the overall size is sufficiently small to pass through the cardiac arterioles.

EXAMPLES

Examples provided below are intended to be non-limiting embodiments of the inventions disclosed herein.

Example 1—Development of Scale-Up Allogeneic Manufacturing

Cardiosphere have previously been harvested from percutaneous endomyocardial biopsies (e.g., those obtained from humans or pigs) as an autologous source tissue. In some cases, an allogeneic stem cell therapy approach may be preferable. The present study tested the ability to successfully scale-up production of cardiac stem cells (e.g., cardiospheres or CDCs from test allogeneic whole hearts collected from organ donors. Two human hearts were obtained for research purposes (one from a donor after cardiac death [DCD]). Hearts were subjected to established manufacturing processes for autologous CDCs and the resulting products characterized with respect to growth and phenotypic identity. The effects of tissue storage and tissue sampling from various regions of the heart were examined. Comparative methods as disclosed herein were developed to allow for process scale-up. Additionally, pig CDCs were manufactured for a preclinical study from two pig hearts were obtained, one for analysis of process changes and one for preclinical study manufacturing. Human CDCs were also utilized to assess the effect of process changes.

Materials and Methods

Immediately upon receipt, hearts were grossly dissected into five separate regions of interest: atria (both right and left), apex, left ventricular epicardium (LV), right ventricular epicardium (RV), and right septal epicardium (the region from which endomyocardial biopsies are typically obtained). Tissue from each region was cut into biopsy-sized pieces of about 25 mg each (500 µm×500 µm×500 µm; though in some embodiments, other sizes are used), referred to as explants. Human hearts were cut using scissors and a scalpel as described (see e.g., U.S. patent application Ser. No. 10/567,008, filed Jul. 13, 2006 which is incorporated in its entirety by reference herein), while pig hearts were cut using a automated tissue slicer (Zimmer® Dermatome) and automated tissue chopper (McIlwain™ Tissue Chopper, Ted Pella, Inc.). Explants were then processed as previously described (see e.g., Smith et al. 2007 and U.S. patent application Ser. No. 11/666,685, filed Apr. 21, 2007 and U.S. Ser. No. 13/412,051, filed Mar. 5, 2012, the entireties of each of which are incorporated by reference herein), or subjected to storage. Cold stored tissue was kept at 4° C. for three or six days in cardioplegia solution (VIASPAN, DuPont Merck) with 100 U/mL heparin (APP Pharma). Cryopreserved tissue was resuspended (75 mg/mL) in CryoStor® CS5 or CS10 (BioLife Solutions) in cryovials, placed directly in a CryoMed (ThermoFisher) controlled-rate freezer, and then transferred to liquid nitrogen.

Allogeneic CDC Storage and Formulation

In order to generate allogeneic CDCs, after digestion with 1 mg/mL collagenase for 15 minutes at 37° C., explants were plated on a 100 mm fibronectin (25 ng/mL; BD Biosciences) coated dish or CELLBIND® CellSTACK® vessels (Corning Life Sciences). After 1-2 weeks, cellular outgrowth emerging from the explants became confluent. These explant derived cells (EDCs) were harvested using 1× TrypLE™ (Invitrogen). EDCs were either cryopreserved as the master cell bank (MCB), and then cultured as cardiospheres (CSps), or placed immediately into CSp culture conditions. CSps were grown on poly-D-lysine (20 mg/mL; BD Biosciences) coated plates or UltraLow CellSTACK® vessels (Corning Life Sciences). Allogeneic CDCs were grown by seeding CSps on fibronectin-coated dishes or CELLBIND® HYPERFlask® vessels (Corning Life Sciences) or Nunc* TripleFlasks (Thermo Scientific), and passaging when confluent. In some instances (for use in non-clinical experiments), CDCs were utilized hypothermic (never frozen). In these cases, CDCs were resuspended in phosphate-buffered saline (PBS). Alternatively in preparation for cryopreservation, allogeneic CDCs were resuspended (2.5 million/mL [human] or 1.25 million/mL [pig]) in CryoStor CS5 or CS10 with or without 100 U/mL heparin (as noted). In some instances (as noted) CDCs were filtered through a mesh with a pore size of 40 µm (Steriflip® Filter Units, Millipore) prior to cryopreservation, though other pore sizes may be used in other embodiments. The CDC suspensions were loaded into cryobags (PL07 PermaLife Bags, OriGen Biomedical Inc), placed directly in a CryoMed controlled-rate freezer, and then transferred to liquid nitrogen. Upon thawing, in some instances (as noted) allogeneic CDCs were filtered prior to use with a pediatric blood filter (Charter Medical) with pore size of 150 µm. Cell clumps were assessed in each preparation using a Multisizer™ 4 COULTER COUNTER® (Beckman Coulter).

Statistical Analysis

All results are presented as mean±SD. Statistical significance between two groups was determined using the 2-tailed unpaired t test and among groups by ANOVA followed by the Tukey test to compare all pairs. Differences were considered significant for p<0.05.

Results

Human Donor Profiles

Figure 3B:
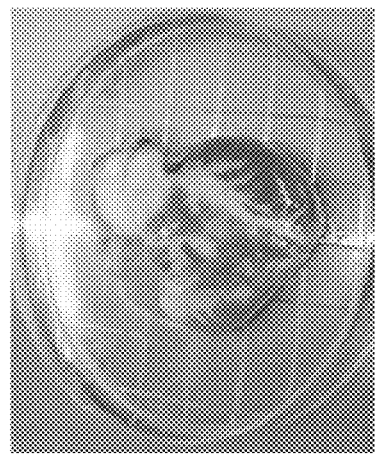
FIGS. 3A-3C depict aspects of human donor hearts used for allogeneic CDC manufacturing. A) Donor heart #1 prior to dissection. B) Donor heart #2 prior to dissection. C) CDC culture process, including: explant with 7 days of cellular outgrowth, (left panel) cardiospheres after 3 days of being plated on poly-D-lysine (center panel), monolayer of CDCs at 90% confluency plated on fibronectin (right panel).
Figure 3A:
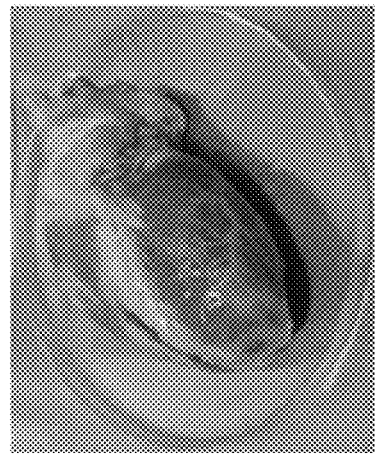
Figure 3C:
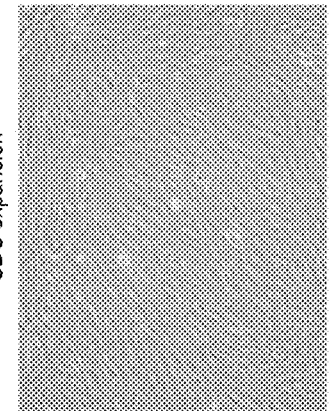
Figure 3C:
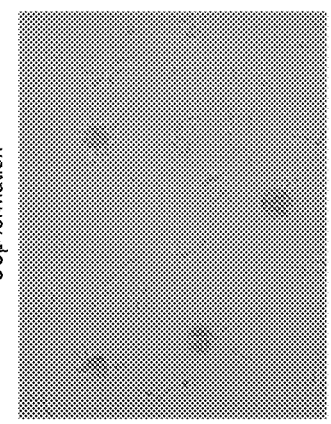
Figure 3C:
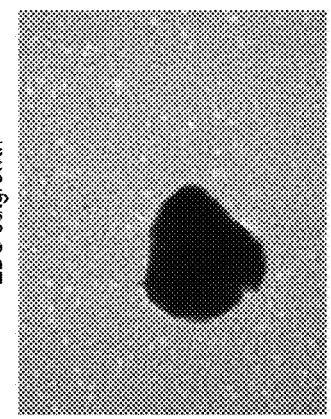

Two hearts were obtained from NDRI (Table 1). The first donor heart (OD35211, FIG. 3a) was obtained from an 11 year-old DCD (donation after cardiac death) male, had been subjected to 39 minutes of warm ischemic time, where 5 minutes is more typical, was delivered within 28.5 hours of cross-clamp, and had explants seeded within 49 hours of cross-clamp. This heart had been a candidate for valve harvesting and so had cuts made in the right and left ventricle on either side of the septum. Cut edges were slightly browned and tissue from the edges was discarded. The second donor heart (OD35220, FIG. 3b) was obtained from a 3 year-old male who was not DCD, was delivered within 27 hours of cross-clamp, and had explants seeded within 34.5 hours of cross-clamp. FIG. 3c depicts various steps in the culture process. No major differences were observed culturing CDCs from the allogeneic source tissue as compared to the autologous source tissue used in prior studies.

TABLE 1

Human Donor Profiles

| Parameter | DCD Donor | Non-DCD Donor |
|---|---|---|
| ID | OD35211 | OD35220 |
| Age | 11 yo | 3 yo |
| Sex | male | male |
| Race | Caucasian | Caucasian |
| Warm Ischemic Time | 39 min | NA |
| Time from cross-clamp to delivery | 28.5 hr | 27 hr |
| Time from cross-clamp to explants | 49 hr | 34.5 hr |
| Heart Weight | 190 g | 75 g |

Effects of Tissue Storage

Figure 4A:
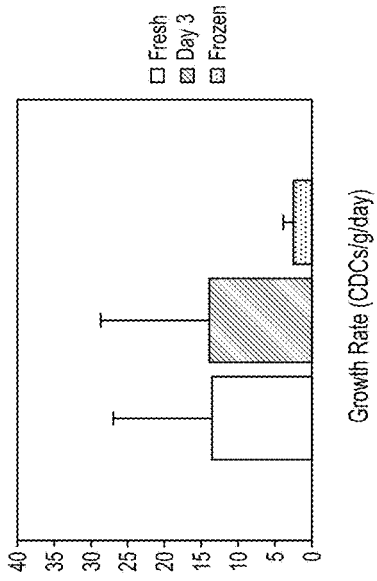
FIGS. 4A-4C depict effects of tissue and allogeneic CDC storage conditions. A) Amount of CDCs generated over time from explants plated either the day of dissection (Fresh), after three days in cold storage (Day 3), or after freezing and thawing (Frozen). B) Growth rate of CDCs expressed per gram of tissue per day processed fresh, stored cold, or frozen. ANOVA=0.0612. C) Effect on viability, recoverability, and proliferation of CDCs frozen and then thawed at different time points.
Figure 4B:
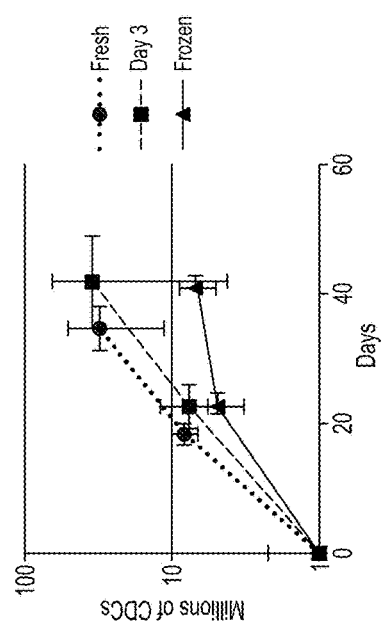

The potential effect of tissue storage was examined using both donor hearts. Four out of 12 specimens taken from the DCD heart (overall 17% of specimens) and stored for 6 days failed to yield CDCs, illustrating that 6 days of storage, in some embodiments, produce less than optimal CDC yield. Accounting for those specimens which did yield CDCs, data demonstrate a slight effect of 3 days of cold storage in terms of the time required to achieve a similar CDC yield (FIG. 4a), and a larger effect seen after freezing and thawing the specimen manifested as both a decrease in average yield and an increase in processing time (FIG. 4a). Overall, calculated growth rates were somewhat impacted by cryopreservation (Fresh=13±13, Day 3=14±15, Frozen=2±1 M CDCs/g/day; FIG. 4b); however, no process failures occurred following either 3 days of cold storage or cryopreservation. Given the enormous amount of flexibility created with frozen tissue, tissue banking prior to processing that is optionally used, in some embodiments. Further, cold storage allows for several days of additional flexibility in processing.

Effects of CDC Storage

Figure 4C:
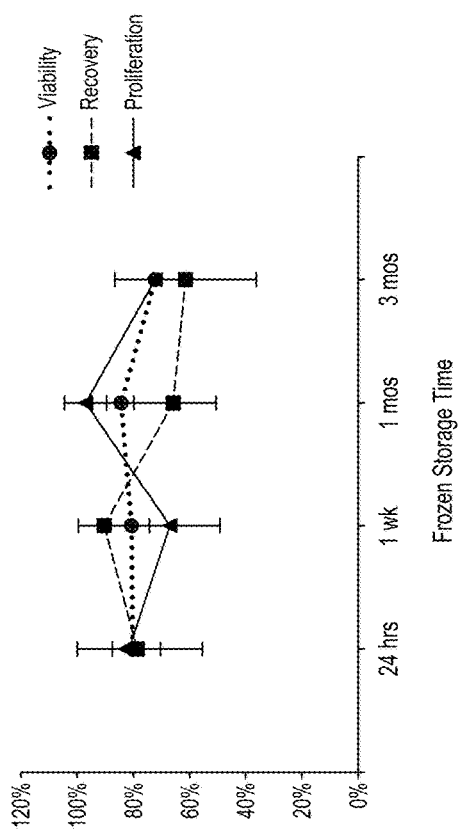

The potential effect of cryopreservation on cell viability, recovery, and proliferation was evaluated by comparing fresh CDCs to those frozen and thawed after a period of 1-90 days (FIG. 4c). Post-thaw viability of CDCs averaged 80±9% after 1 day of cryopreservation, recovery 79±22%, and proliferation over the course of 6 days was 82±6% of baseline. No significant changes in any parameter occurred as the period of cryopreservation was extended out to 90 days when compared to the 1 day control. These data demonstrate that, in several embodiments, generating CDCs from whole hearts stored temporarily and of banking cells is a viable methodology in some manufacturing embodiments.

Regional Differences in CDCs

Figure 2B:
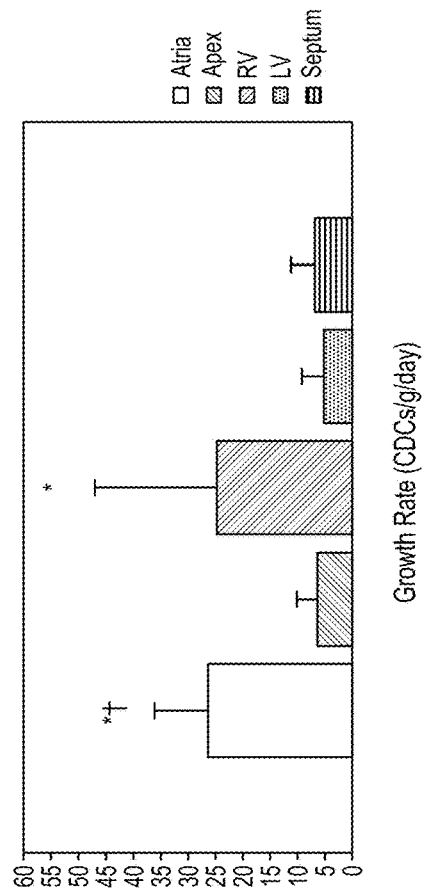
FIGS. 2A-2B depict data related to the growth of CDCs produced from various regions of the heart. A) Amount of CDCs produced over time from the atria, apex, right ventricle, left ventricle, or septum. B) Growth rate of CDCs per gram of tissue per day for each of the five regions. ANOVA=0.003. Comparison for all pairs using Tukey test: *p<0.05 vs LV, †p<0.05 vs apex.
Figure 2A:
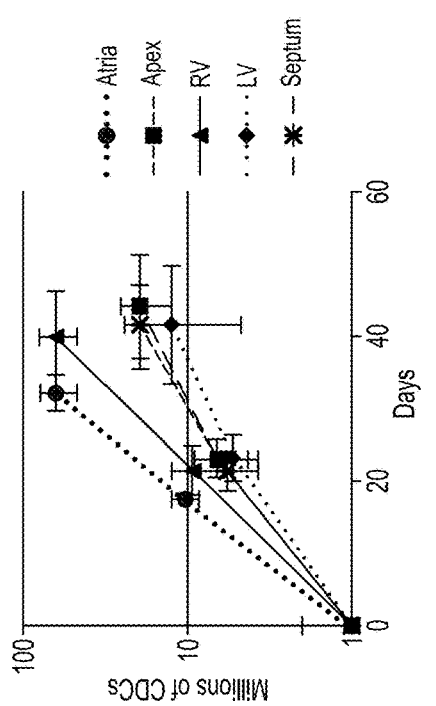

Data pooled from the two donors also demonstrate that yields from the atria and right ventricle were greater than yields from the other regions, but that CDCs could be produced using tissue from all regions reliably (FIG. 2a). When calculated growth rates were compared, tissue samples from the atria and right ventricle yielded 4 to 6-fold more CDCs compared to other regions (atria=26±10, RV=25±22, apex=6±4, LV=5±5, septum=7±4 M CDCs/g/day; FIG. 2b).

Figure 5:
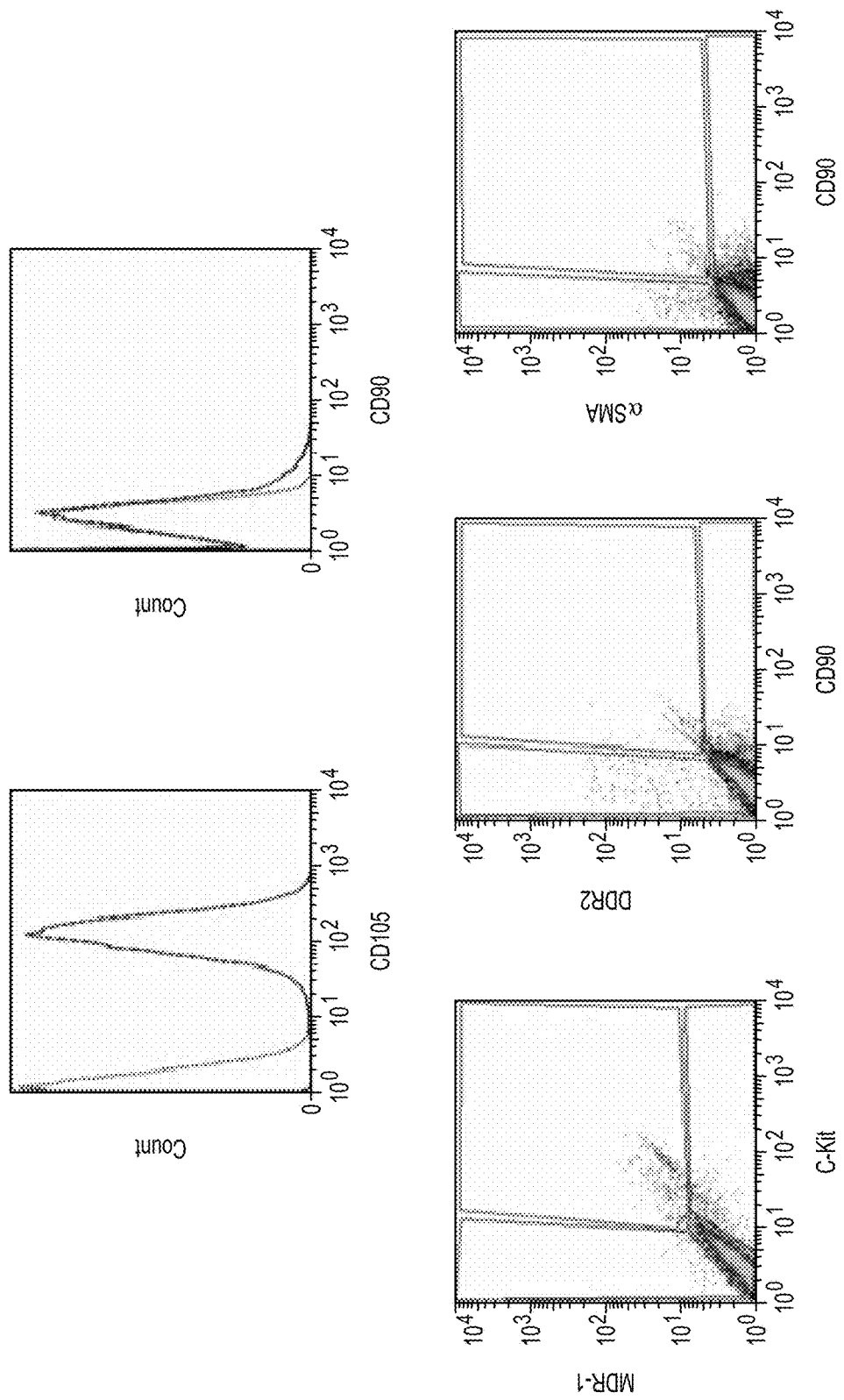
FIG. 5 depicts an example phenotype of Allogeneic CDCs. Histograms show CDC expression of CD105 and CD90. Solid lines represent labeled cells. Dotted lines are isotype controls. Dot plots show co-expression of c-Kit with MDR-1, CD90 with DDR2, and CD90 with αSMA.

A panel of markers was next used to define CDCs generated from each region (Table 2). It is established that human CDCs express CD105 (the regulatory component of the TGF-β receptor complex), are negative for CD45, and contain multiple cell sub-populations of cardiac progenitor cells (c-Kit+CD90−), cardiac mesenchymal-like cells (CD90+c-Kit−), and endothelial progenitor cells (CD31+c-Kit− or CD34+c-Kit−). Data shown here are consistent with prior expression profiles. MDR-1 and Abcg2, both multi-drug resistance pumps, have also been described as antigens present on adult cardiac progenitor cells and constitute a small fraction of CDCs with MDR-1 being co-expressed in 31% of c-Kit+ cells (FIG. 5). CD133 is yet another antigen used to identify endothelial progenitors, but is largely lacking on CDCs. CD29, CD44, CD73, and CD166 are present on adult bone marrow mesenchymal stem cells as well as CDCs. DDR2 was added to the marker panel in order to distinguish cardiac mesenchymal-like cells from cardiac fibroblasts and αSMA to identify cardiac myofibroblasts. Results show that CD90+ CDCs are a relatively homogeneous population, not cardiac fibroblasts or myofibroblasts, but cardiac mesenchymal cells (FIG. 4). Fibroblasts and myofibroblasts in fact make up <5% of the CDC population. The fraction of cardiac progenitors (i.e. c-Kit+, MDR1+, or Sca-1+ CDCs) or supporting cells (i.e. CD90+, DDR2+, or αSMA+ CDCs) derived did not vary much among regions and on average there were 1.9-fold more supporters than progenitors.

TABLE 2

Regional Similarities in Phenotype for Allogeneic CDCs

| | Region | | | | | |
|---|---|---|---|---|---|---|
| Marker | Atria | Apex | RV | LV | Septum | Average |
| c-Kit | 1.6 | 2.4 | 2.6 | 2.4 | 2.4 | 2.3 ± 0.4 |
| MDR-1 | 1.5 | 2.1 | 0.6 | 2.2 | 2.4 | 1.8 ± 0.7 |
| Sca-1 | 1.1 | 1.1 | 1.1 | 0.5 | 0.8 | 0.9 ± 0.3 |
| Abcg2 | 0.7 | 1.9 | 0.4 | 0.6 | 0.7 | 0.9 ± 0.6 |
| CD133 | 0.9 | 0.8 | 0.3 | 0.6 | 0.6 | 0.6 ± 0.2 |
| CD31 | 1.0 | 0.8 | 0.4 | 0.7 | 0.8 | 0.7 ± 0.2 |
| CD34 | 0.9 | 2.1 | 0.7 | 1.3 | 1.0 | 1.2 ± 0.5 |
| CD45 | 0.9 | 0.8 | 0.9 | 0.6 | 0.7 | 0.8 ± 0.1 |
| CD105 | 99.5 | 98.6 | 97.8 | 99.8 | 99.6 | 99.1 ± 0.8 |
| CD29 | 100.0 | 99.7 | 100.0 | 99.9 | 99.8 | 99.9 ± 0.1 |
| CD44 | 99.9 | 99.7 | 99.4 | 99.5 | 99.7 | 99.6 ± 0.2 |
| CD73 | 100.0 | 99.6 | 99.9 | 99.8 | 99.9 | 99.8 ± 0.2 |
| CD166 | 99.2 | 99.2 | 99.4 | 98.6 | 98.5 | 99.0 ± 0.4 |
| CD90 | 4.0 | 13.4 | 8.7 | 6.4 | 2.9 | 7.1 ± 4.2 |
| DDR2 | 1.8 | 2.2 | 1.4 | 2.3 | 1.7 | 1.9 ± 0.4 |
| αSMA | 0.3 | 0.8 | 0.6 | 0.5 | 0.5 | 0.5 ± 0.2 |

Human Donor Differences

No significant differences were observed while culturing CDCs from the two donors, although CDCs from the non-DCD donor grew somewhat better than the DCD donor (FIG. 6a) and calculated growth rates were significantly higher for the non-DCD donor (21±16 vs 7±8 M CDCs/g/day; FIG. 6b). Despite the yield differences, CDCs were generated reliably using tissue from both the DCD and the non-DCD heart.

Next, the amount of tissue equivalent to an endomyocardial biopsy (250 mg) was collected from the septum of each of the two hearts. Both a master cell bank (MCB) of CDCs and a batch of CDCs prepared for theoretical use at P5 were generated. The DCD heart generated a MCB of 41.4 million CDCs and a calculated total of 4.4 billion CDCs at P5. The non-DCD heart generated a MCB of 37.2 million CDCs and a calculated total of 60.6 billion CDCs at P5 (FIG. 6c). CDCs from the non-DCD heart were expanded further to the point of in vitro senescence, which occurred at P10. It is advantageous that senescence occurs with 15 population doublings of the MCB as this can reduce the concern for tumorgenicity in vivo (a theoretical concern never realized in hundreds of animals treated with CDCs but still monitored in clinical studies). In several embodiments, passage 5 presents an optimal time to use CDCs therapeutically, given that P5 CDCs were still in the linear portion of their growth curve. These data demonstrate the feasibility of manufacturing from the allogeneic tissue source at a relevant scale.

Manufacturing Scale-Up Optimization

Figure 7:
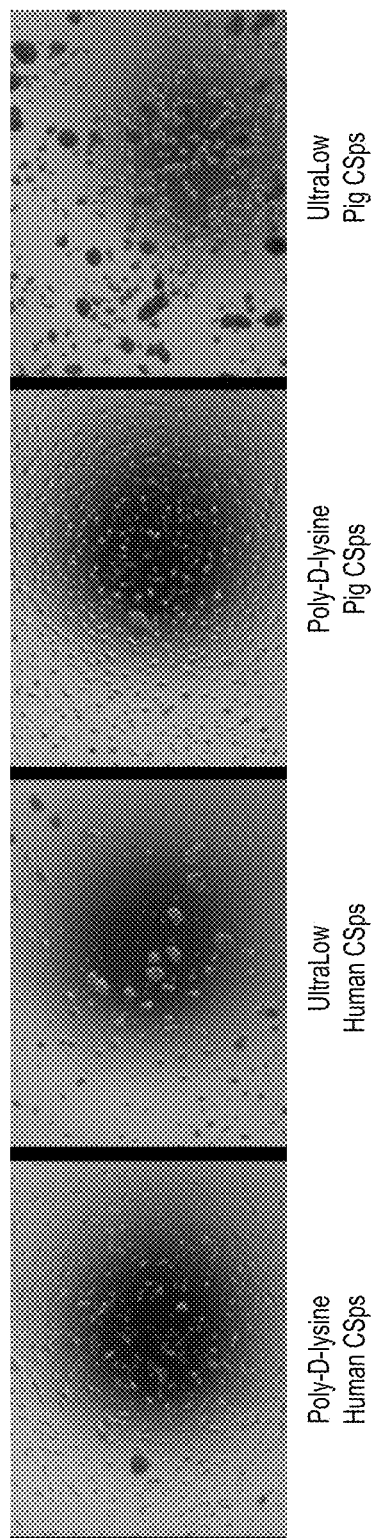
FIG. 7 depicts cardiospheres created using both human and pig cells with the small-scale and large-scale methods.

Tissue was collected from a pig heart in order to test multiple variations on the manufacturing process that would allow for starting with a larger amount of tissue and ease the burden of culturing the resulting number of cells. A tissue slicer and tissue chopper were incorporated into the explant creation stage to enable rapid creation of viable, uniform tissue pieces. Two types of culture vessels, each available with two types of surface treatment, were incorporated into the EDC outgrowth, CSp formation, and CDC expansion stages to reduce the vessel footprint, reduce the total number of culture vessels, and eliminate two reagents (poly-D-lysine and human fibronectin, though these reagents, or their functional equivalents/alternatives may optionally be used, in several embodiments). A comparison of the small-scale and large-scale methods (Table 3) revealed no difference in the culture time required before harvesting EDCs, no significant difference in EDC yield (the cell population that would make up the MCB), a decrease in the culture time required before collecting CSps, no significant difference in CSp appearance (FIG. 7) or yield (expressed as subsequent P1 CDC yield), and no significant difference in CDC doubling time in a head-to-head comparison using the same pig source tissue and/or human MCB. A summary of the impact of certain manufacturing changes is shown in Table 4.

In several embodiments, the disclosed methods are suitable for the processing of large quantities of donor heart tissue. For example, an average lab, using the disclosed methods could routinely process 40 grams of donor tissue at a time. At this scale, extrapolating from the human data above, approximately 850 intracoronary doses of allogeneic cardiac stem cells can be derived, even after accounting for necessary quality control losses (driven largely by the viral agent testing required on the MCB). It shall be appreciated that in view of the optimized procedures disclosed herein, further scale-up (e.g., by processing additional tissue) could result, in several embodiments, in even greater capacity and flow-through. A comparison the efficiency of growing explant derived cells from the autologous and allogeneic process is shown in Table 5. As evidenced by these data, the scale up processes disclosed herein maintain the overall efficiency of the harvest of cells (on a per gram tissue basis) as compared to more time consuming and less automated methods used previously yet allow unexpectedly increased overall yields. Moreover, the increased starting material available, coupled with the reduced manpower (e.g., due to, at least in part increased automation) the disclosed methods allow for a large yield of therapeutic cells as well as substantial cost and time savings.

TABLE 3

Results of Manufacturing Scale-Up

| Process Step | Small-scale Method | Large-scale Method |
| --- | --- | --- |
| Explant Creation | 11 days to harvest EDCs: | 11 days to harvest EDCs: |
| EDC Outgrowth | 5.9M pig EDCs | 5.8M pig EDCs |
| CSp Formation | 6 days to harvest CSps: | 3 days to harvest CSps: |
|  | 0.75M pig P1 CDCs | 0.54M pig P1 CDCs |
|  | 2.0M human P1 CDCs | 1.4M human P1 CDCs |
| CDC Expansion | doubling time of 2.2 days for human CDCs | doubling time of 2.4 days for human CDCs |

TABLE 4

Summary of Manufacturing Scale-Up

| Process Step | Small-scale Method | Large-scale Method | Result |
| --- | --- | --- | --- |
| Explant Creation | Scissors and scalpel | Tissue slicer | Slice tissue quickly at uniform 500 μm thickness |
|  |  | Tissue chopper | Chop slices quickly into uniform explants 500 μm³ |
| EDC Outgrowth | Human fibronectin coating | CellBIND surface | Eliminate human reagent |
|  | 100 mm petri dishes | CellSTACK flasks | Reduce 830 dishes to 80 flasks |
| CSp Formation | Poly-D-lysine coating | Ultra-Low surface | Eliminate reagent variability |
|  | 6 well plates | CellSTACK flasks | Reduce 11 plates to 1 flask |
| CDC Expansion | Human fibronectin coating | CellBIND surface | Eliminate human reagent |
|  | T175 flasks | HYPERFlasks or Triple flasks | Reduce 150 flasks to 15-48 flasks |

TABLE 5

Cell Culture Performance

|  | EDCs/gram of tissue | Average EDC Yield |
| --- | --- | --- |
| CAP-1001 | 35.6 × 10⁶ EDCs/g[1] | 9.8 × 10⁶ cells[2] |
| CAP-1002 | 34.9 × 10⁶ EDCs/g[3] | 281.7 × 10⁶ cells[4] |

Figure 8:
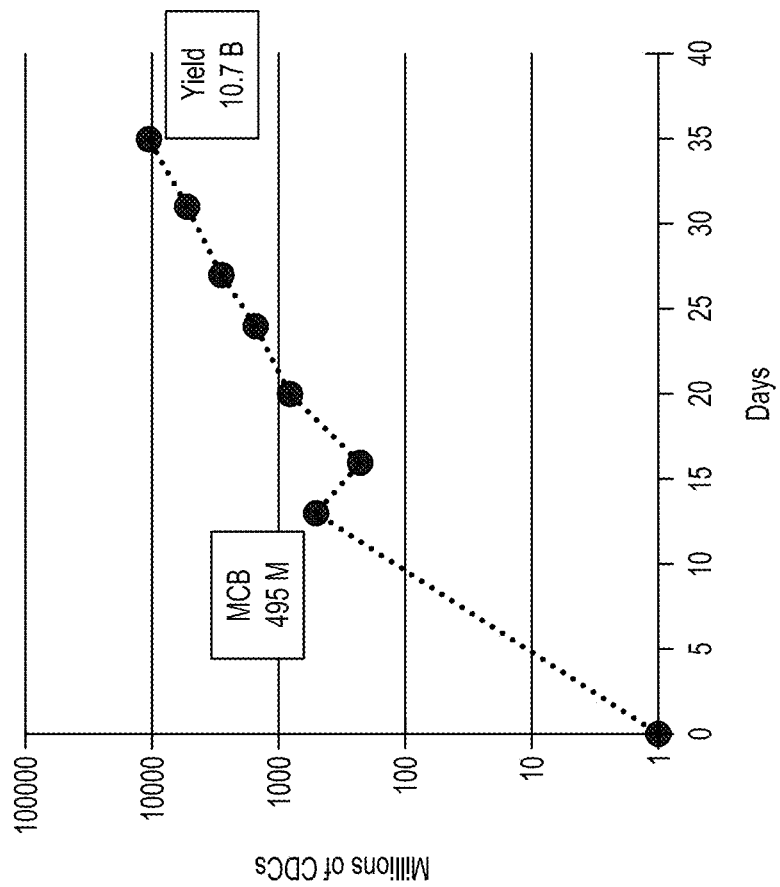
FIG. 8 depicts master cell bank creation and total CDC yield for allogeneic pig donor tissue.

[1] Assumes average biopsy 0.276 g (Makkar et al., 2012)
[2] Average EDC Yield 19 autologous productions (IND#13930)
[3] Calculated based on Grams of Tissue seeded and EDC Yield from 6 Allogeneic Preclinical and Clinical batches
[4] Calculated from 6 Allogeneic Preclinical and Clinical batches Pig CDC Manufacturing A second pig heart (0111) was processed using the scaled-up procedures. The donor pig was SLA (swine leukocyte antigen) typed in order to ensure the greatest degree of mismatch between the donor and the on-study recipients. Tissue (a total of 8.5 g) was collected from the septum, atria, LV, and RV of the donor pig heart and used to generate a master cell bank. The MCB consisted of 495 million cells, which when fully expanded would generate 10.7 billion allogeneic CDCs (FIG. 8).

Figure 9:
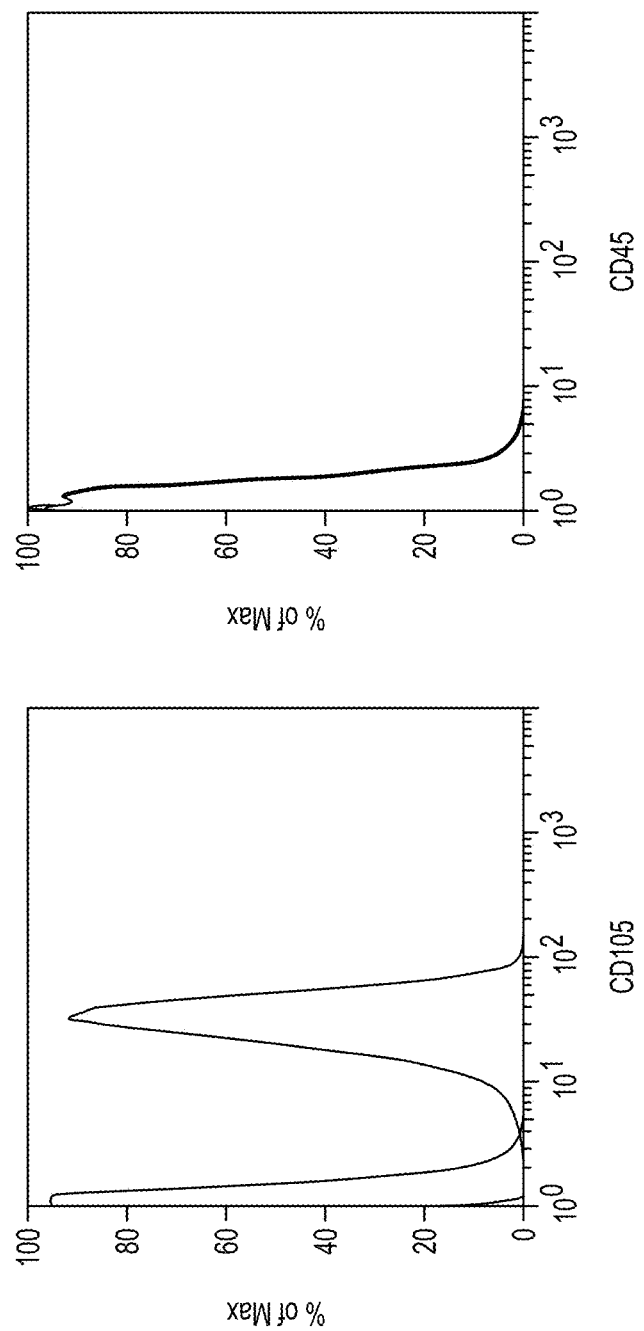
FIG. 9 depicts the immunophenotype of pig CDCs.

FIG. 9 demonstrates that CDCs derived from pigs harbor the same basic markers as those derived from humans in that they are CD105$^+$ and largely negative for CD45.

Catheter Compatibility Testing

Both human and pig CDCs were tested with the various commercially available catheters. CDCs pass readily through either such catheters with no decrease in viability (80±7% pre-test vs 80±8% post-test) and excellent recovery (98±3%, corroborated by 2±3% loss due to adherence) (raw data not shown).

Manufacturing Optimization for Safety

Figure 10:
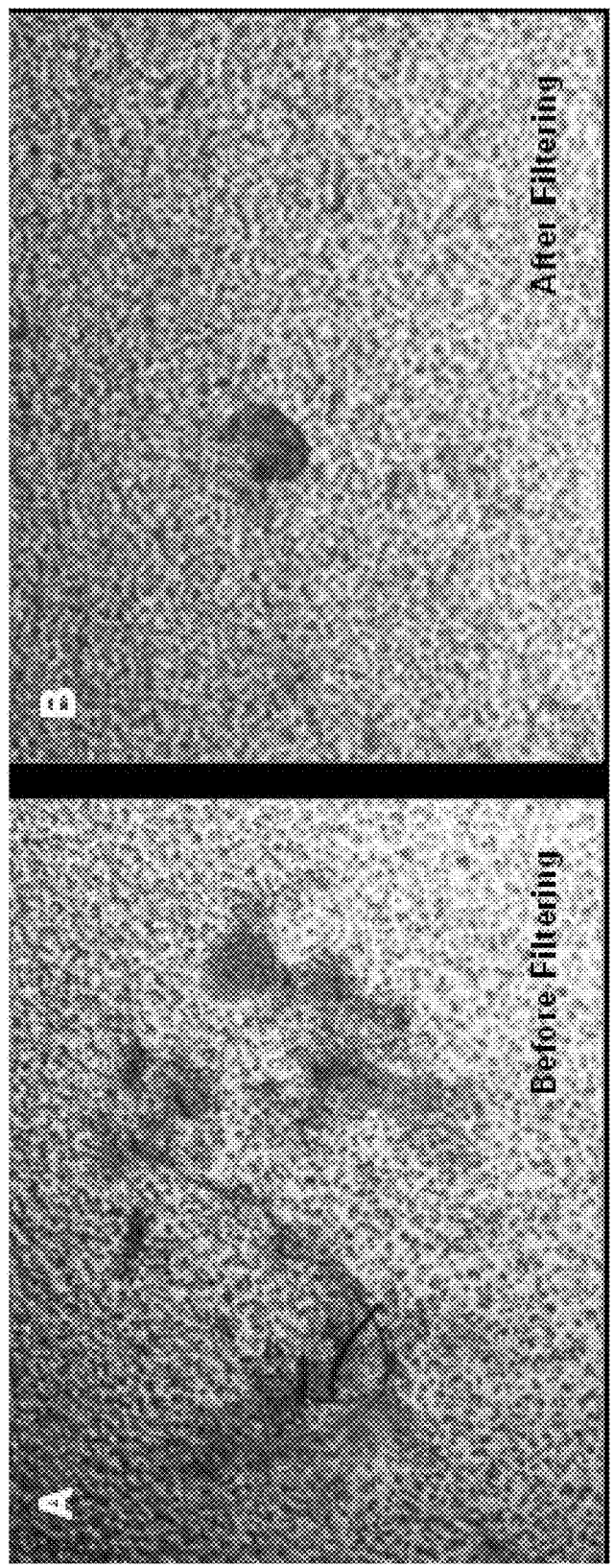
FIGS. 10A-10B depict the effect of filtering on pig allogeneic CDCs. A) Allogeneic pig CDCs thawed as without filtration, a large, rare CDC clump is depicted. B) Allogeneic pig CDCs thawed and filtered. A small, rare CDC clump still remaining is depicted.

To avoid cell clumps prior to administration a filtering step after product thawing and prior to administration was tested. The effect of filtering was first tested in vitro. Filtering using a pediatric blood filter with a pore size of 150 μm was found to have no effect on CDC viability (74% pre-filter vs 85% post-filter viability by Trypan Blue), to result in little product loss (130,000 of 12.5 M Allogeneic CDCs obtained with backwash, ~1% product loss), and to reduce both the size and frequency of cell clumps (FIGS. 10A-10B). As discussed above, a variety of other filter pore sizes and filtration episodes can be used, in various embodiments. In conjunction, in several embodiments, the relative frequency of particulate matter detectable in certain culture vessels can be evaluated and lead to changes in filtration protocols, as needed (e.g., flasks with greater particulate matter can be used with greater filtration stringency).

Figure 11:
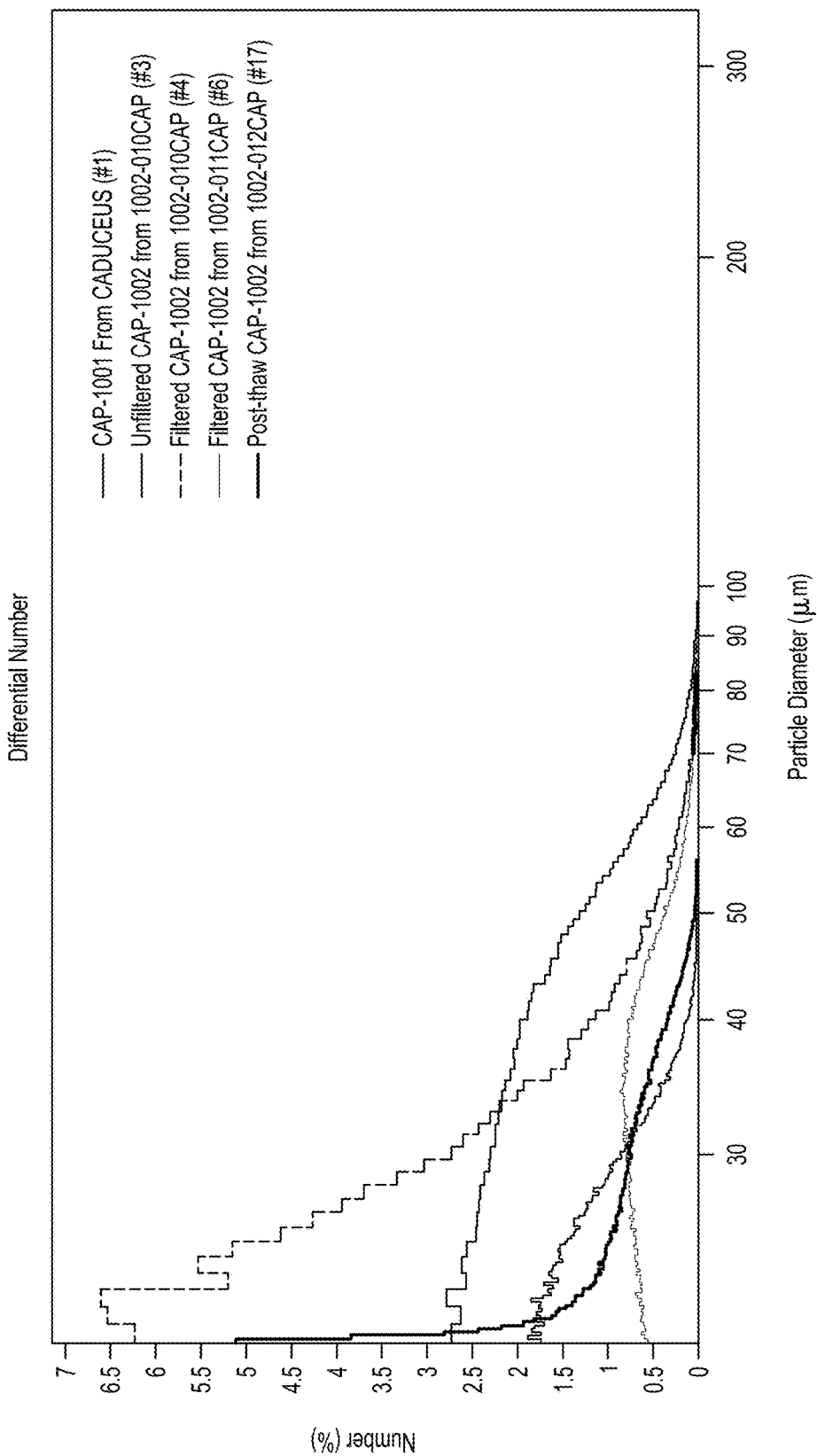
FIG. 11 depicts analysis of cell clumps and particulates present in different CDC preparations. Samples 1, 3, 4, 6, and 17 from Table 6 are depicted.
Figure 12A:
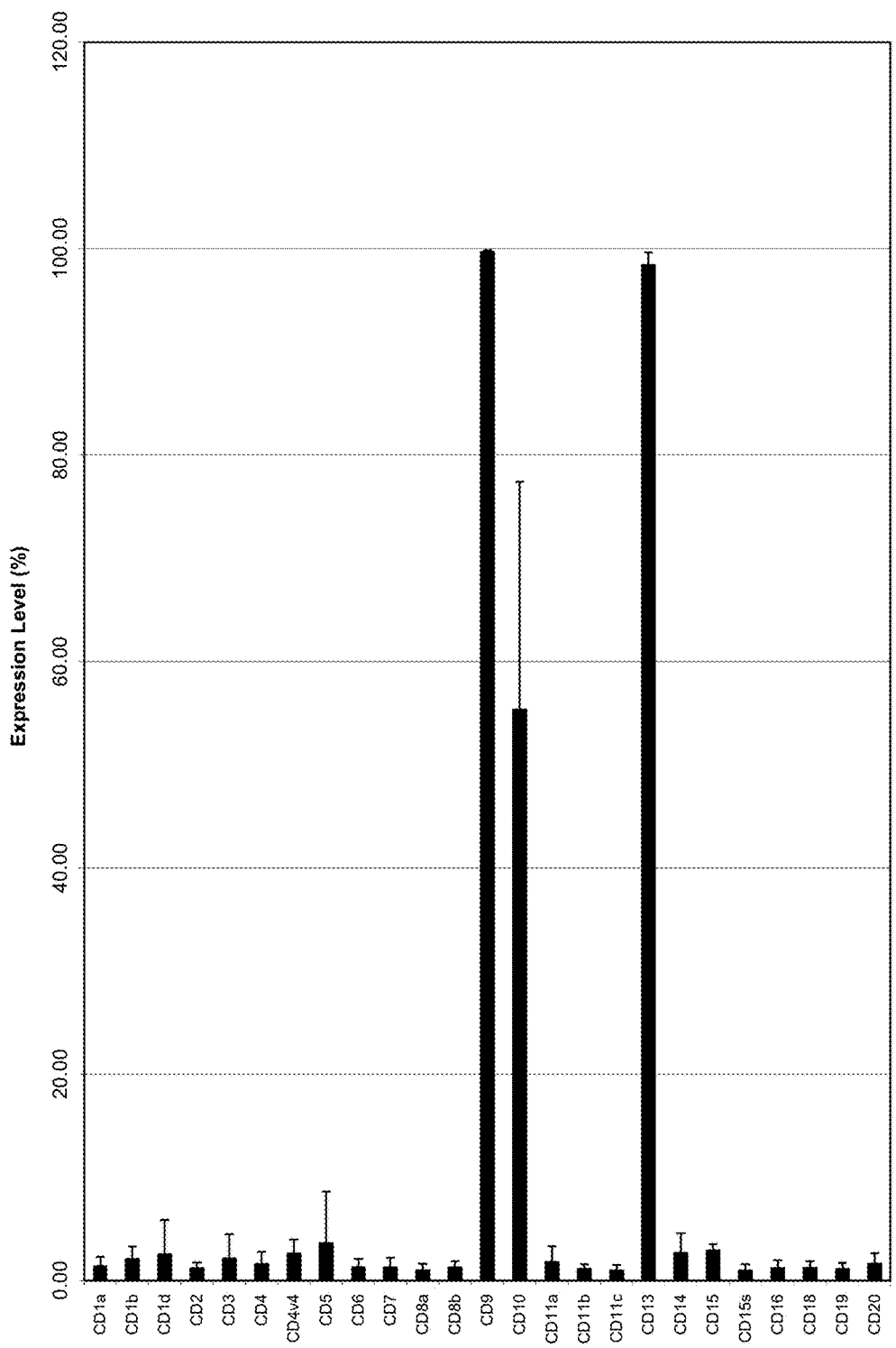
Figure 12B:
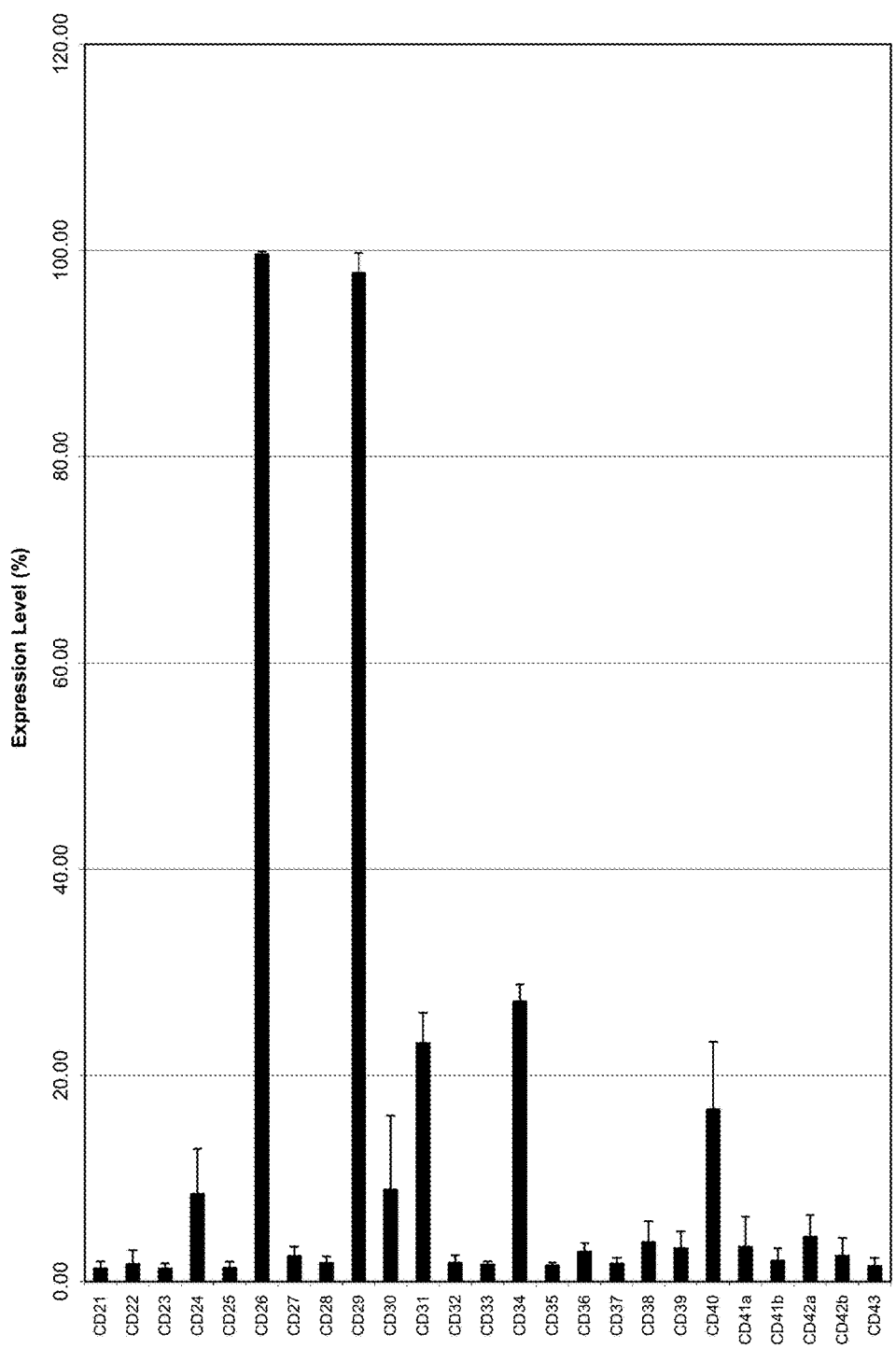
Figure 12C:
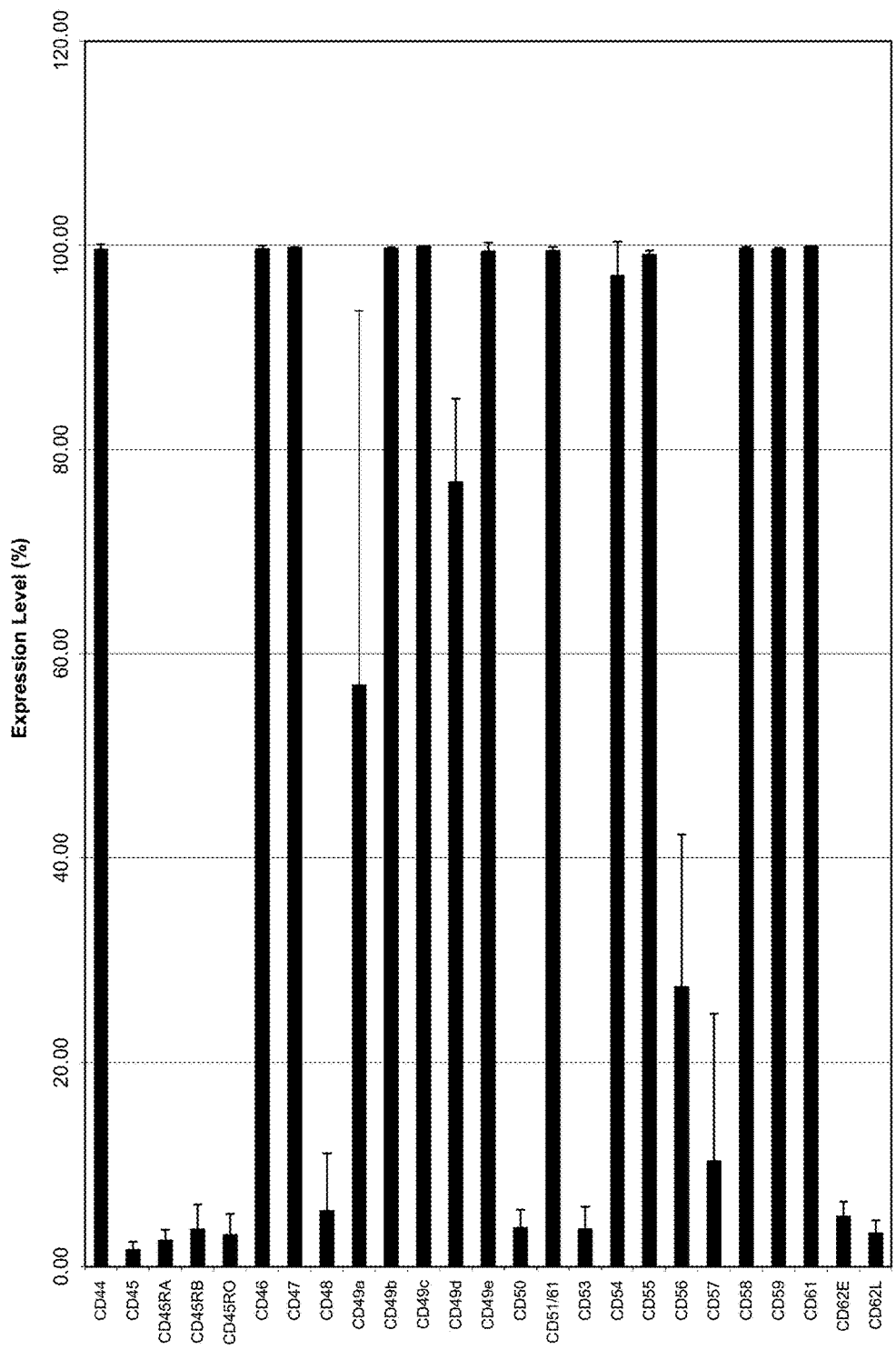
Figure 12E:
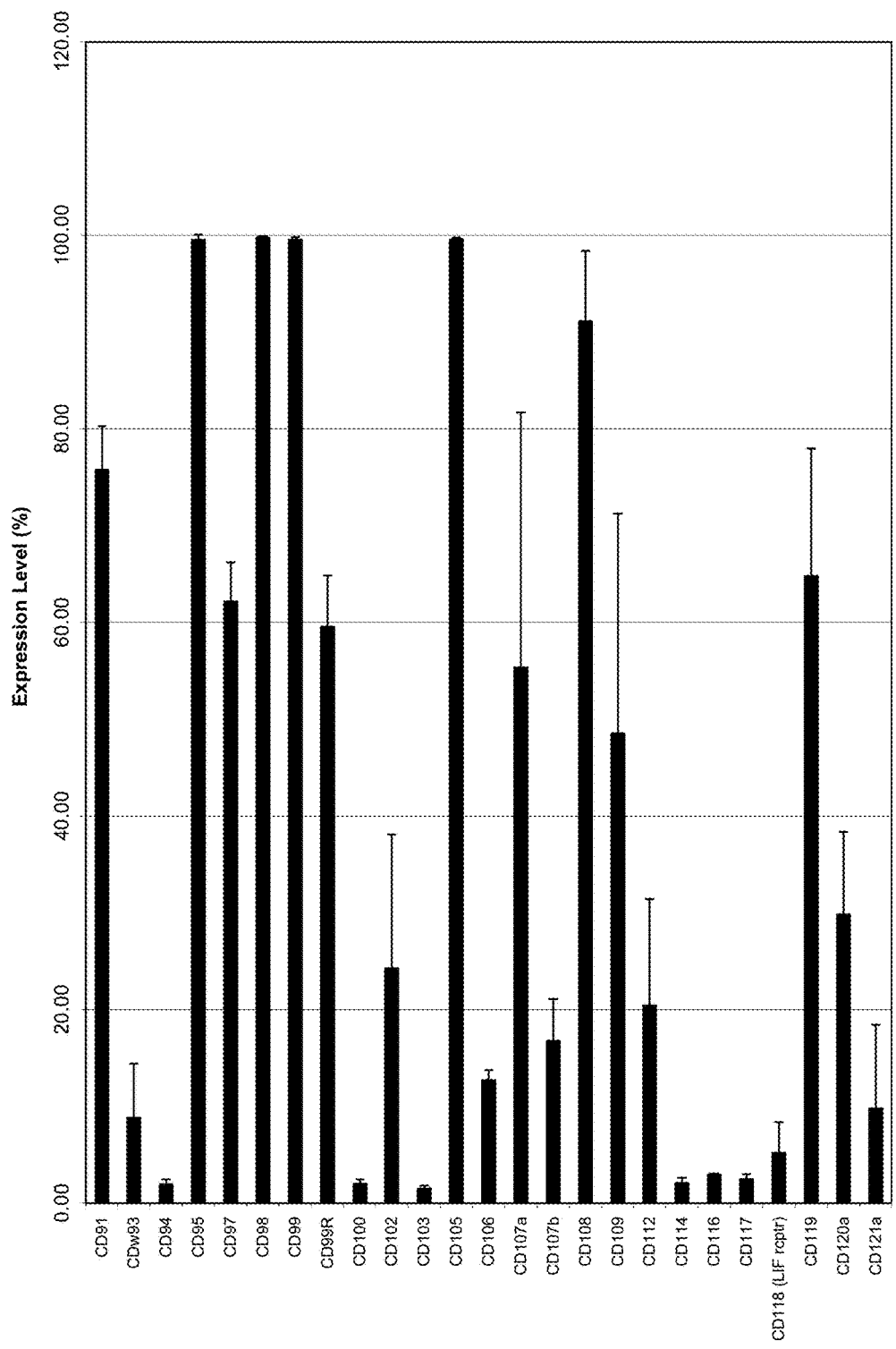
Figure 12F:
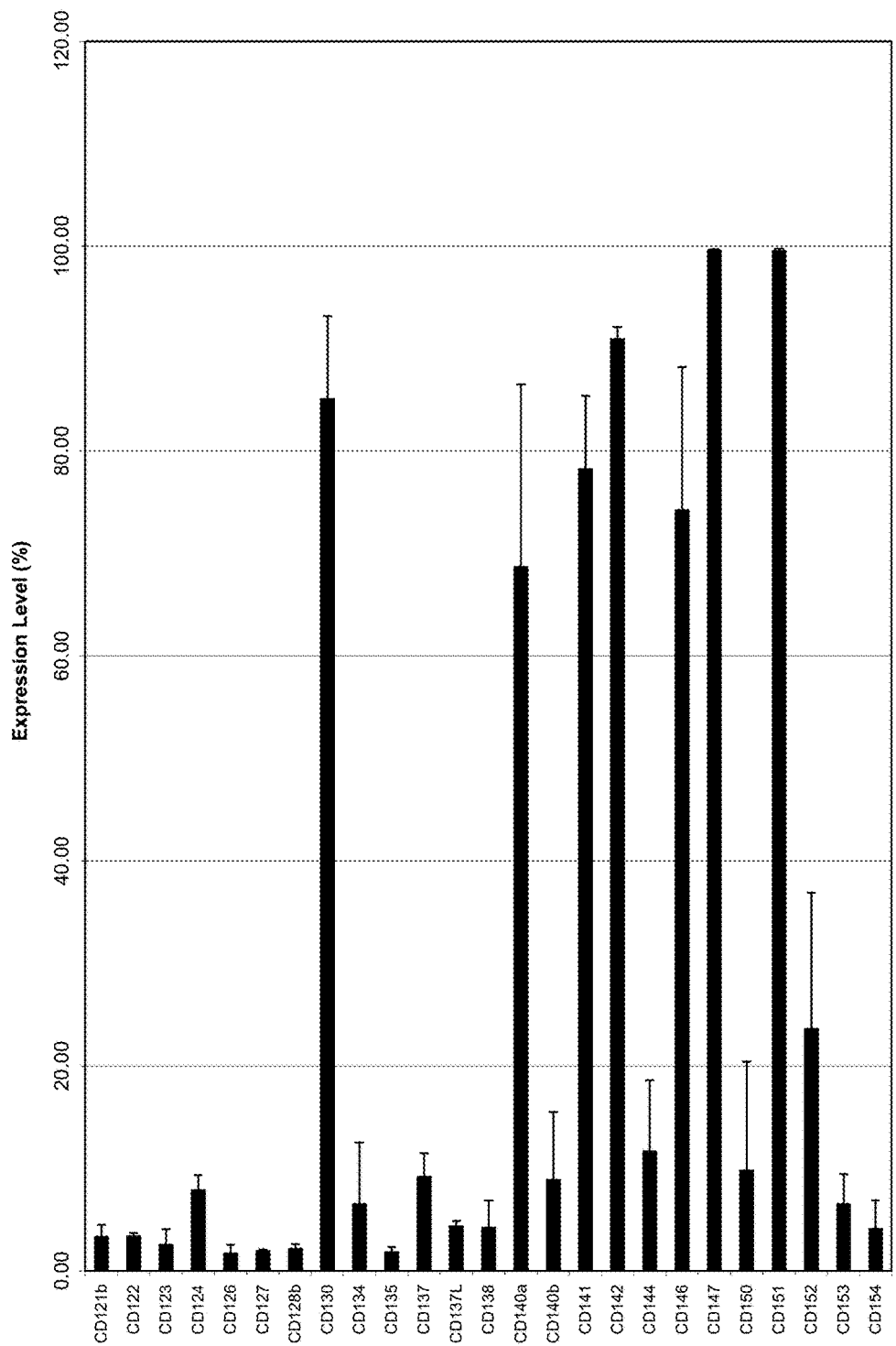
Figure 12G:
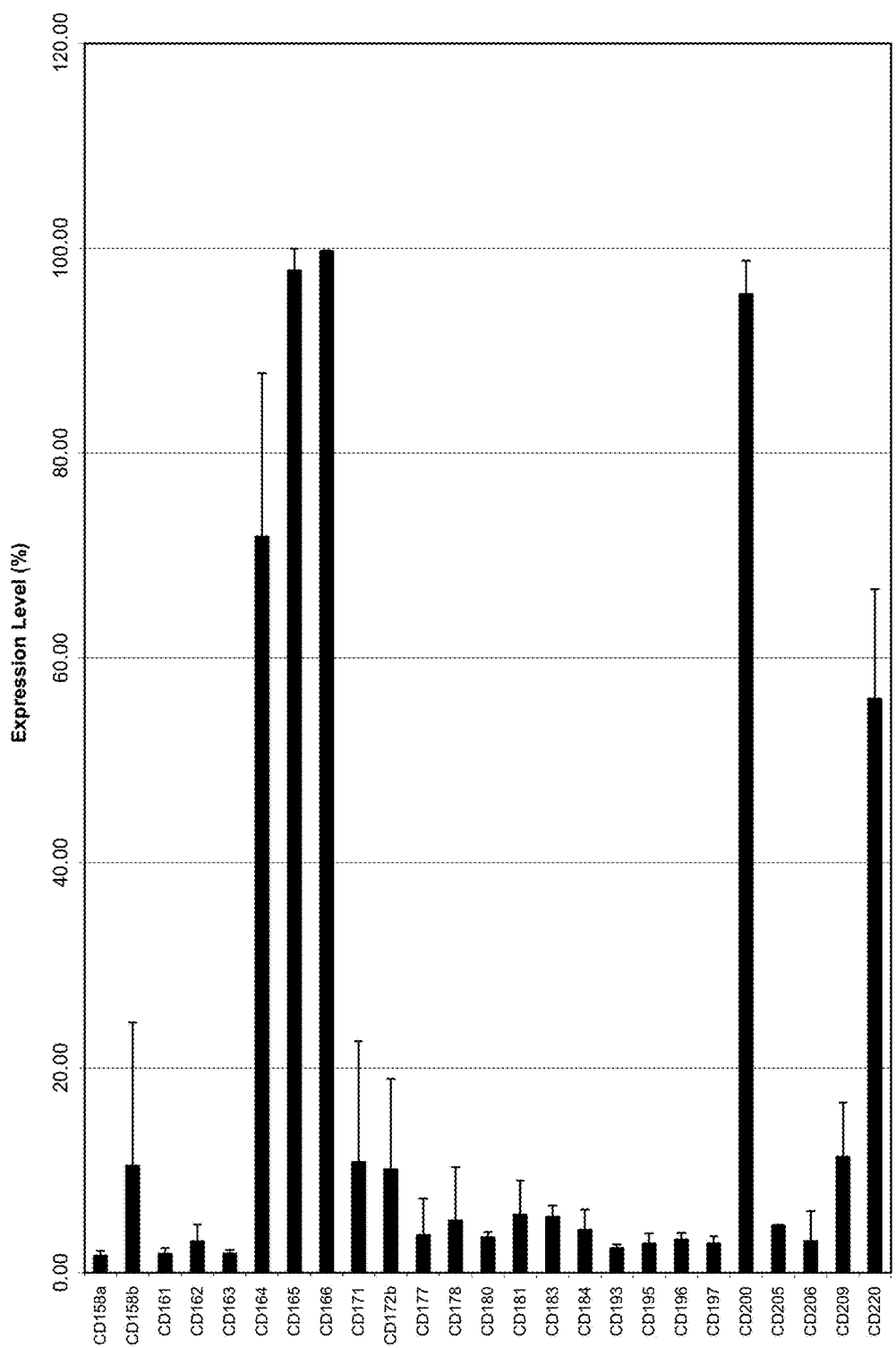
Figure 12H:
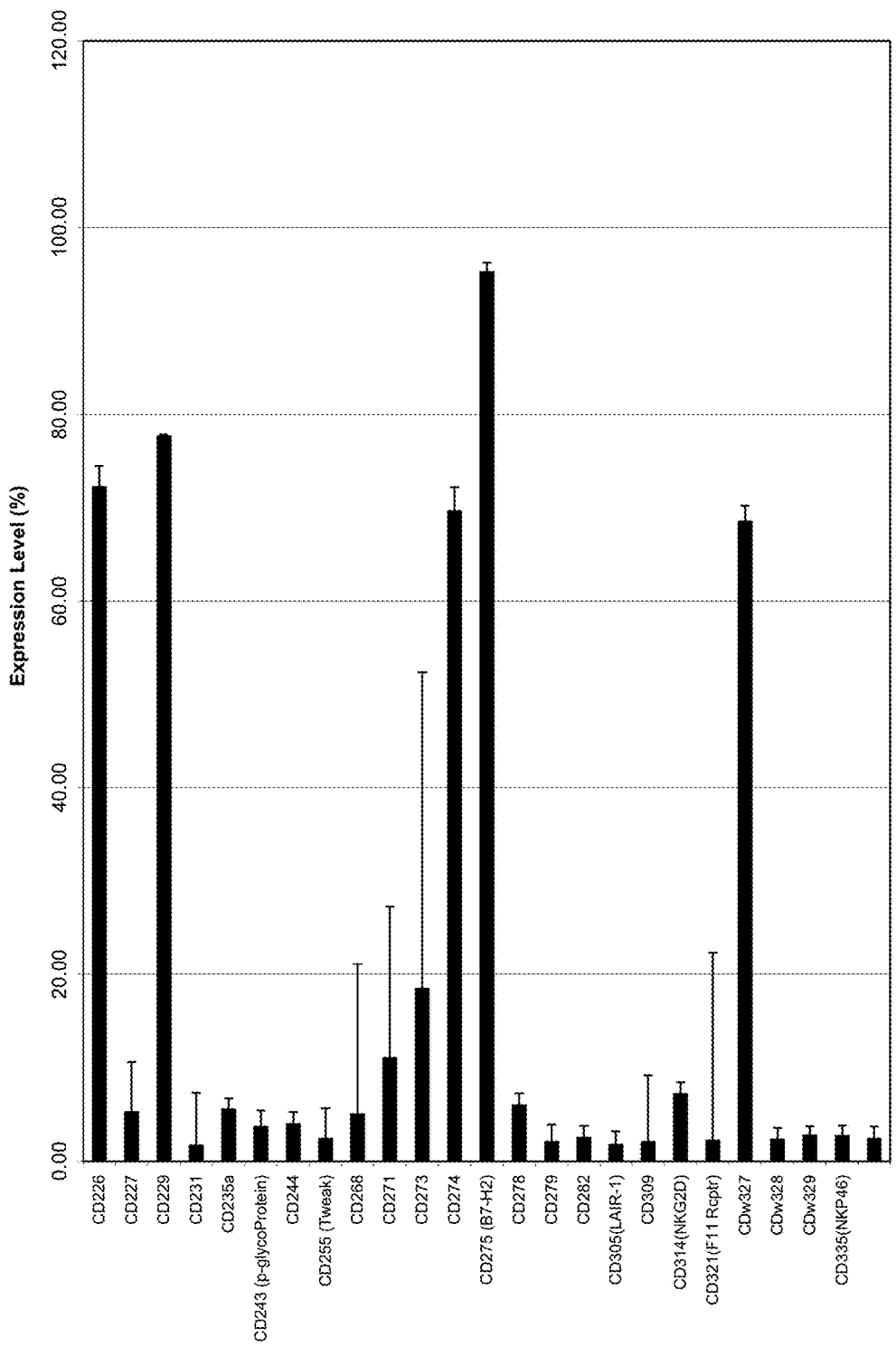
Figure 12I:
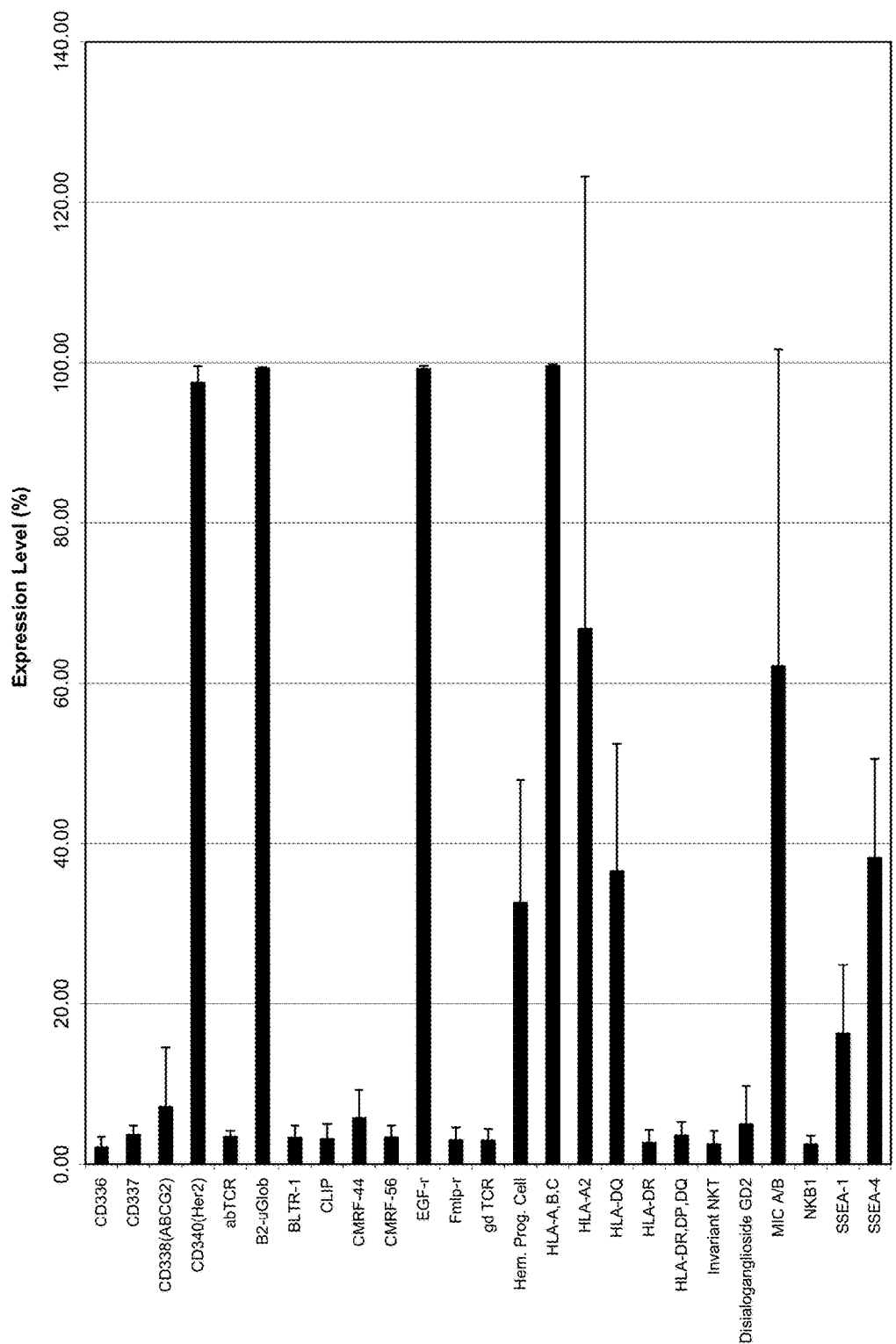
Figure 12J:
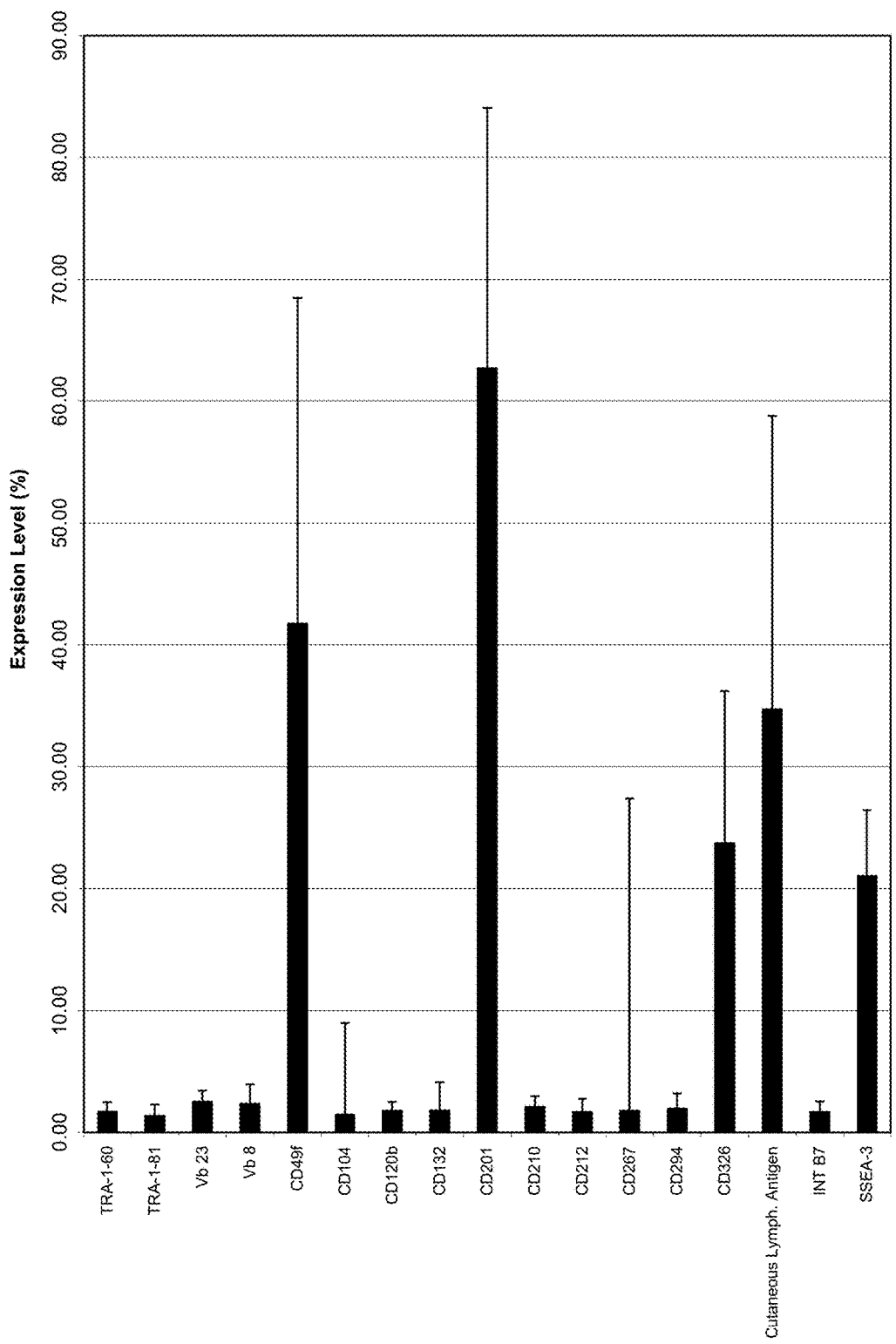
Figure 13A:
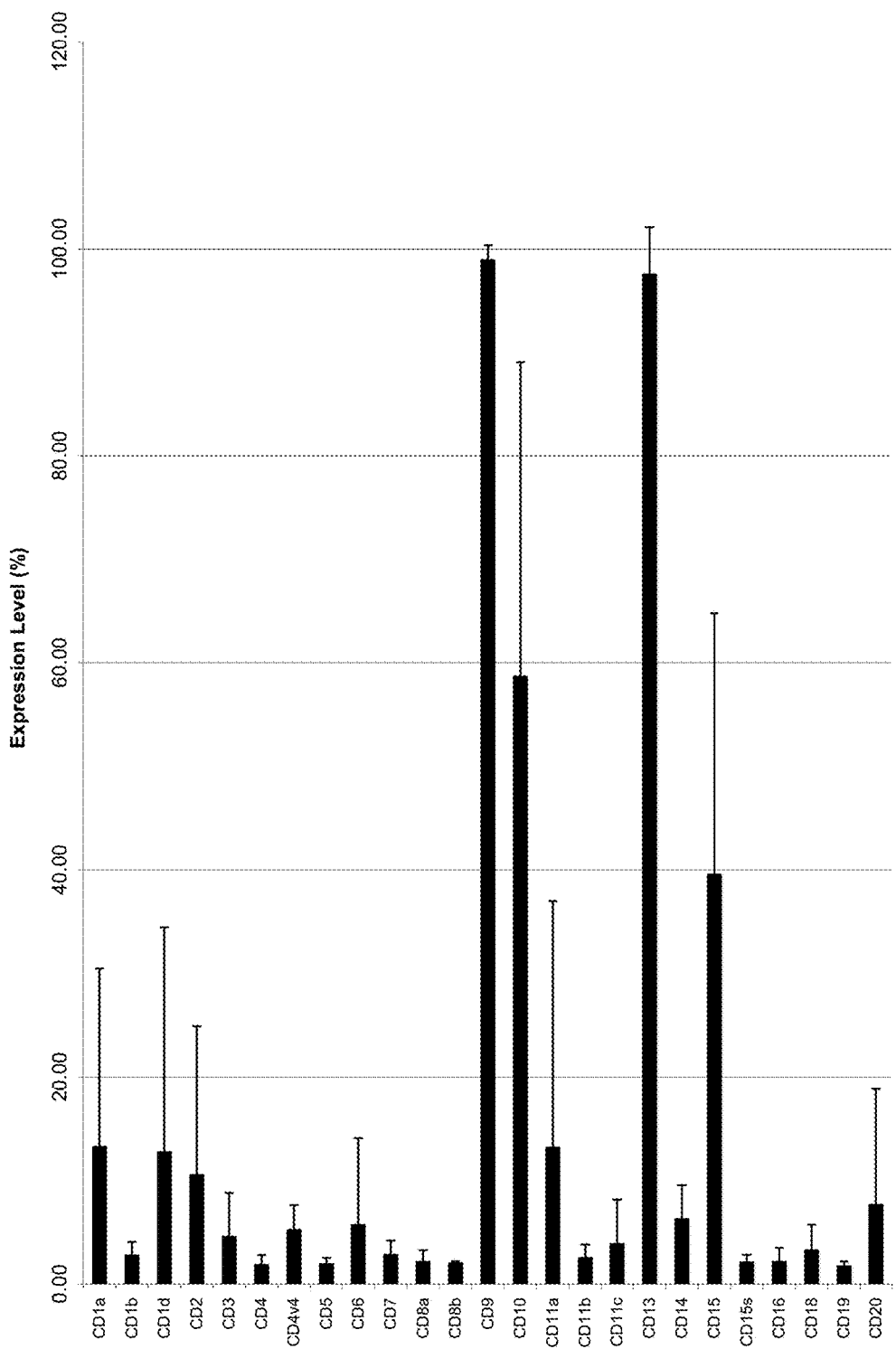
FIGS. 13A-13J depict the average expression levels of 242 cell surface markers on CDC from six separate production runs.
Figure 13B:
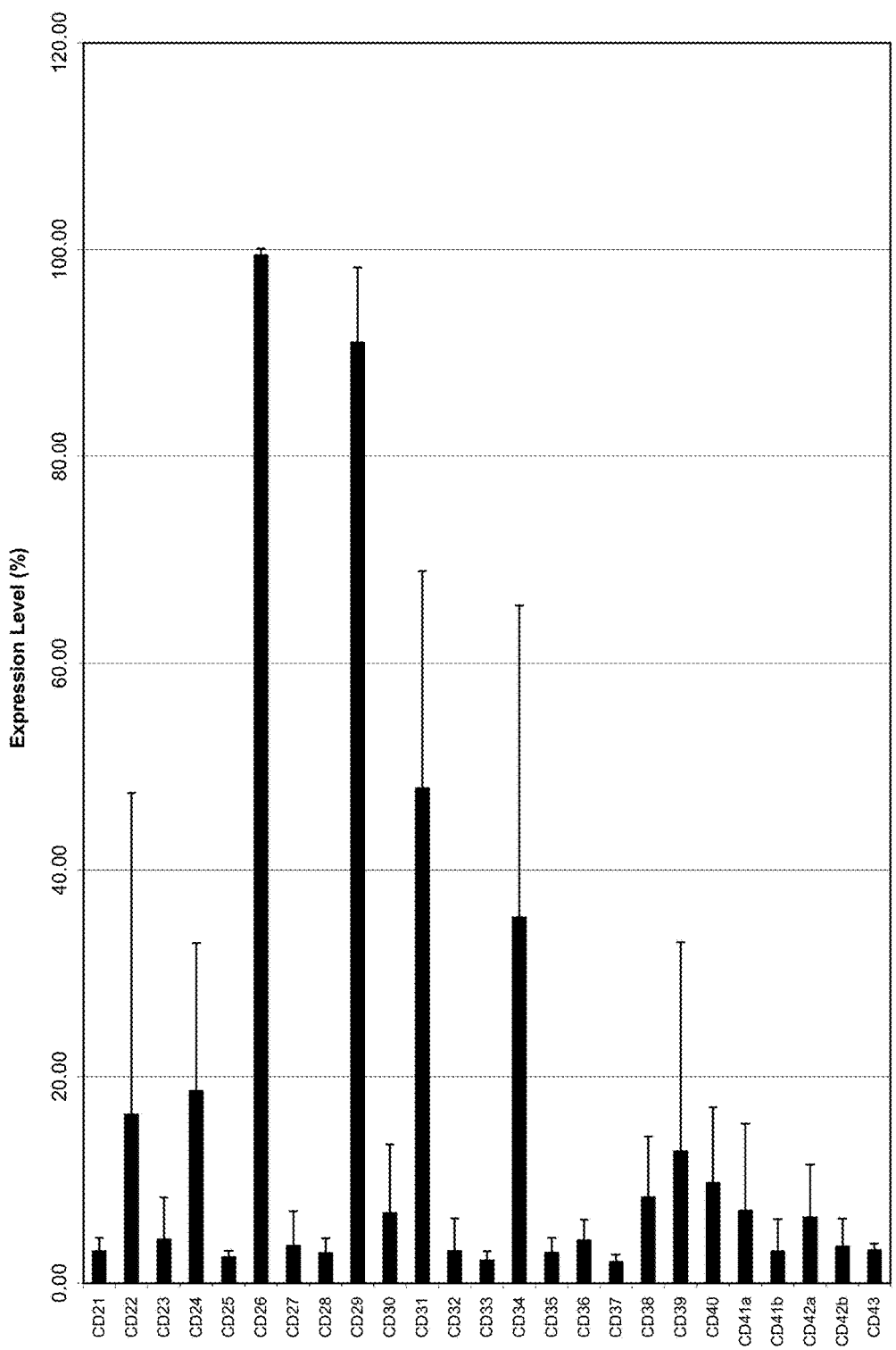
Figure 13C:
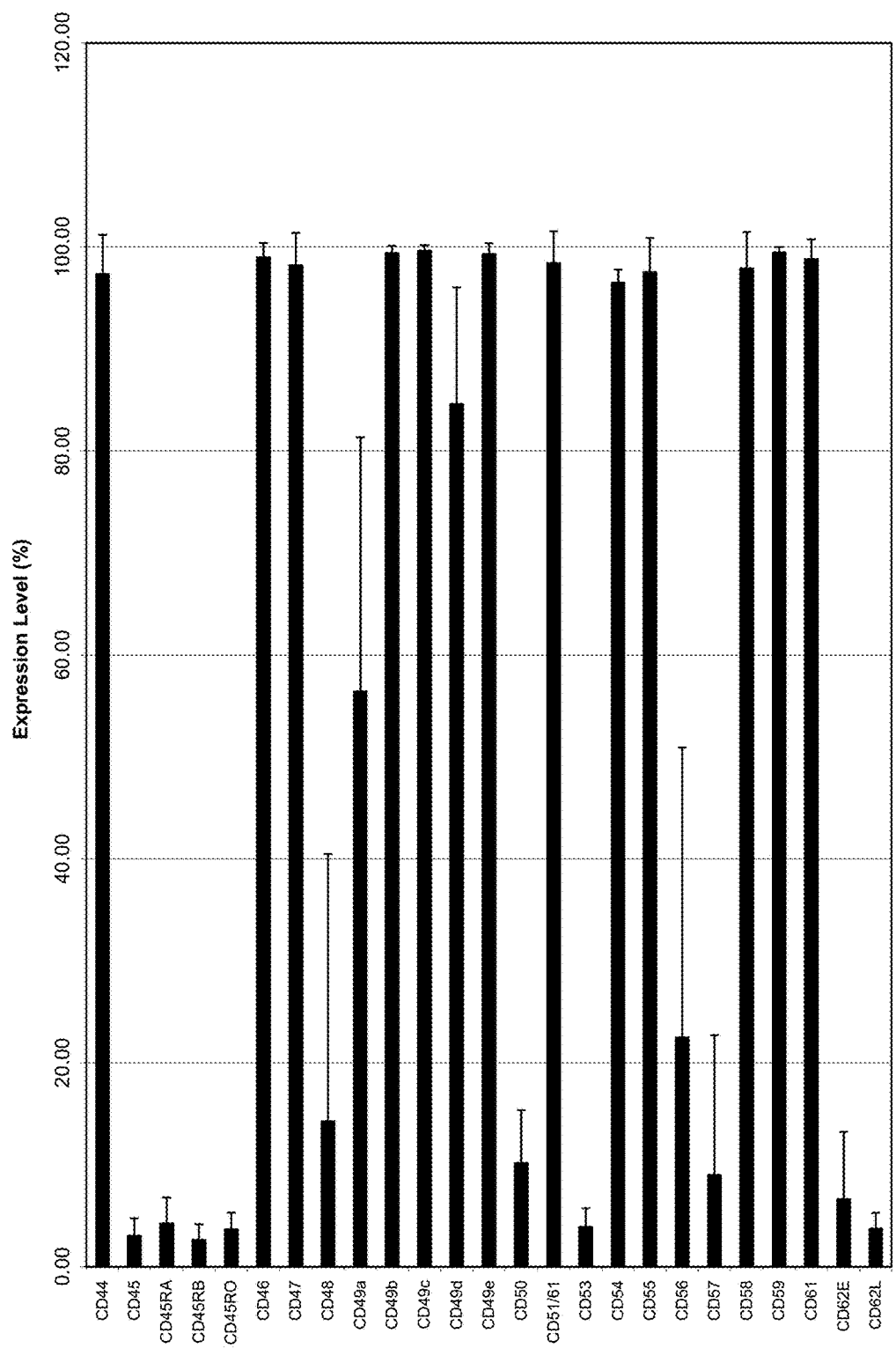
Figure 13D:
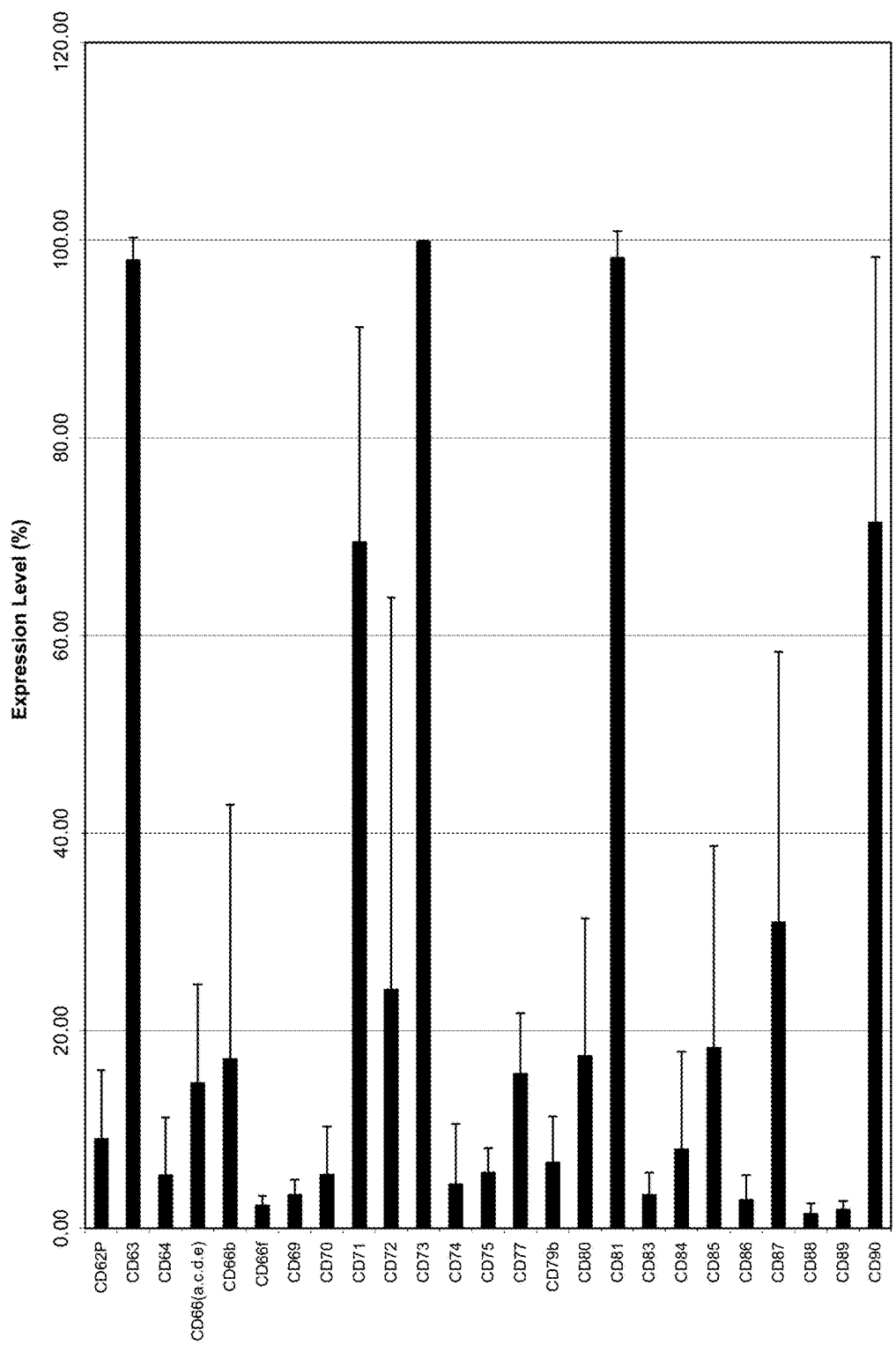
Figure 13E:
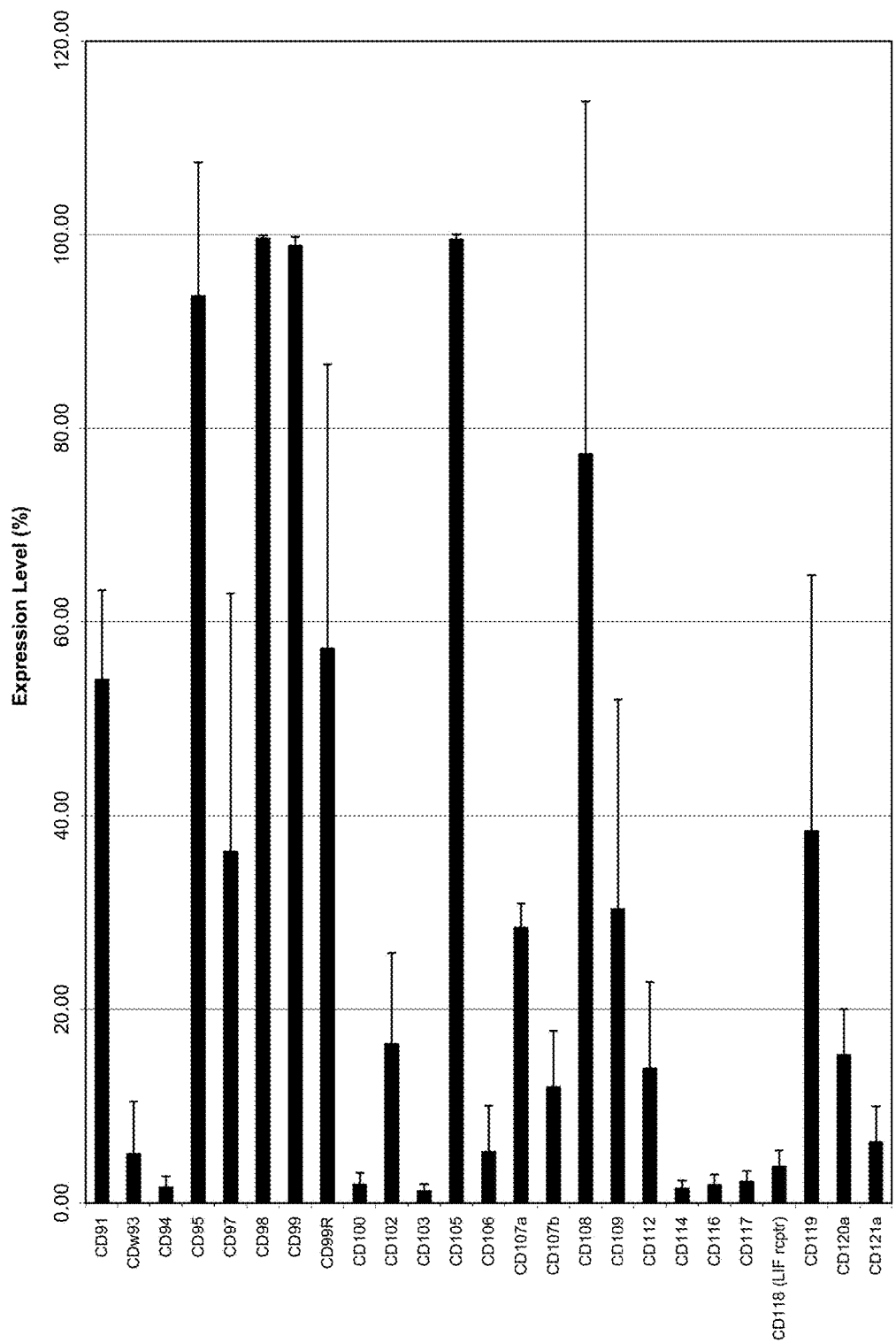
Figure 13F:
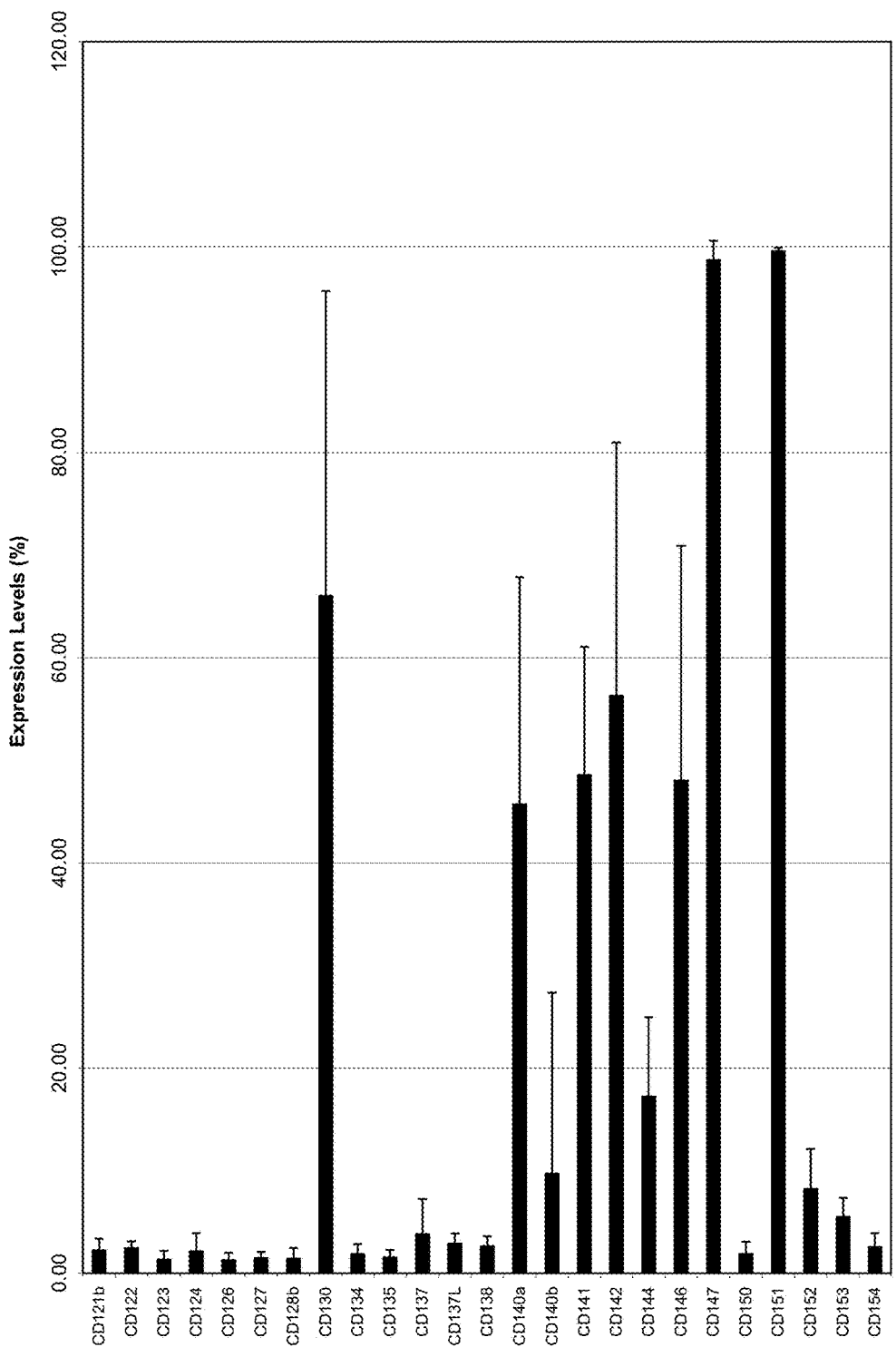
Figure 13G:
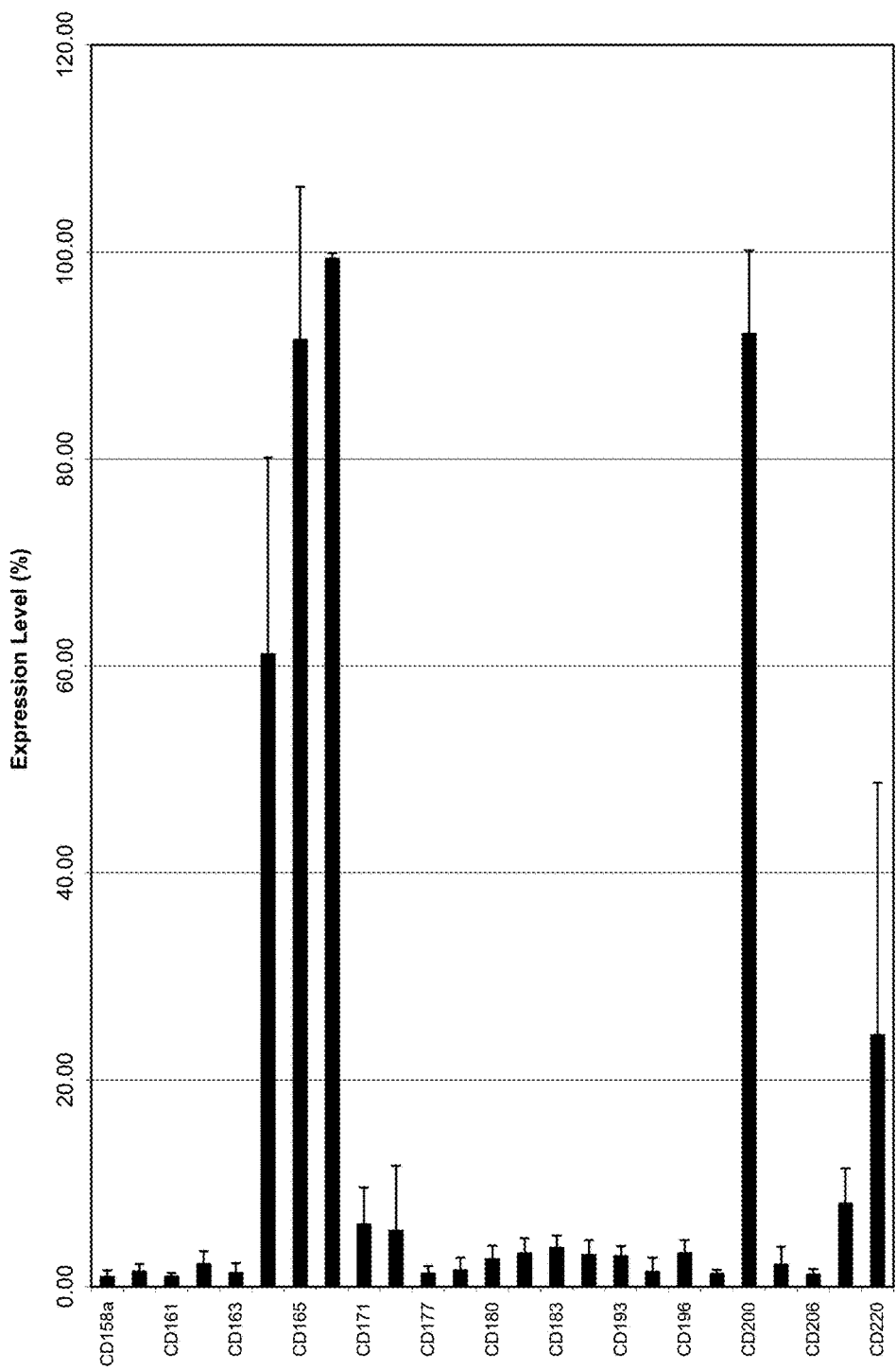
Figure 13H:
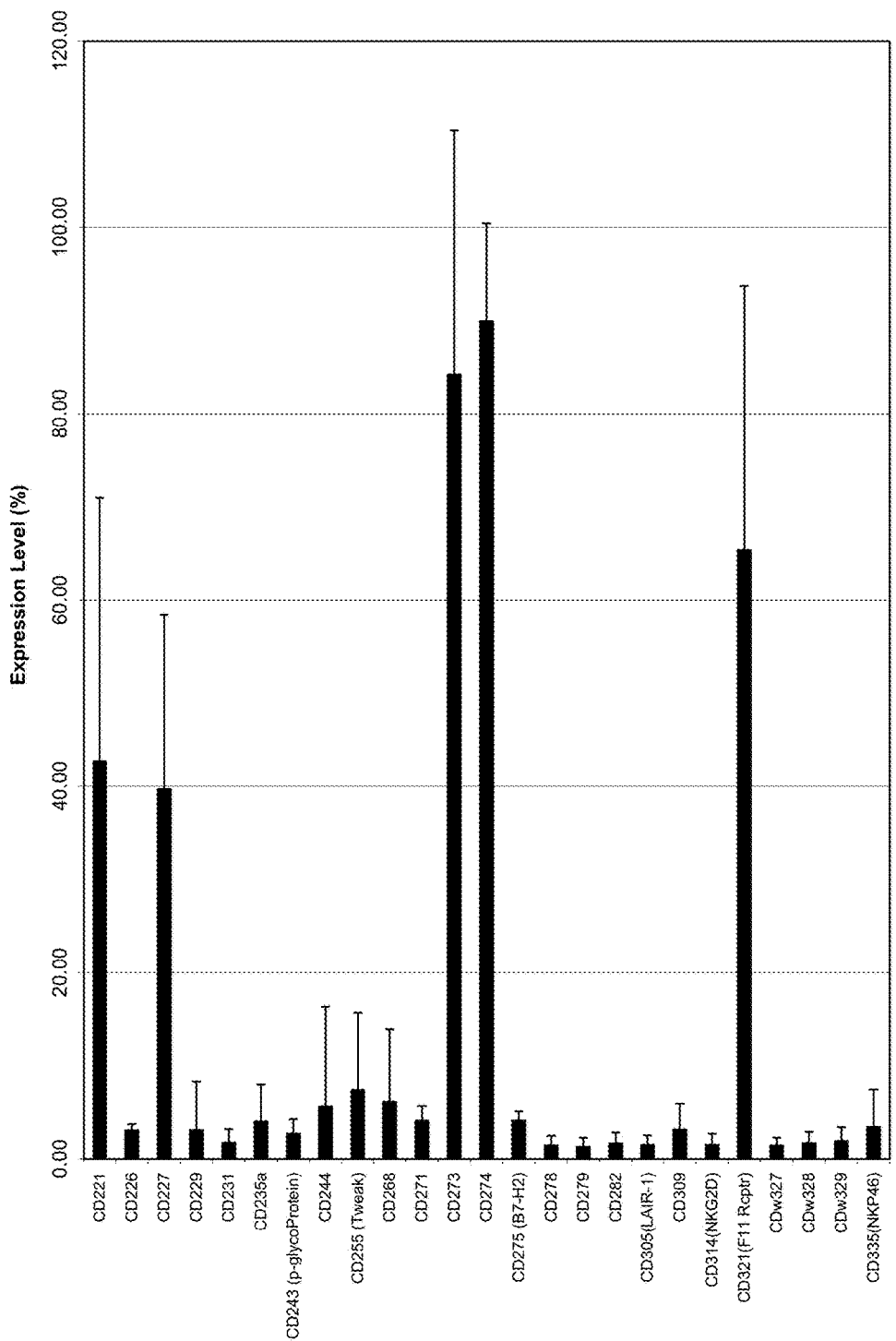
Figure 13I:
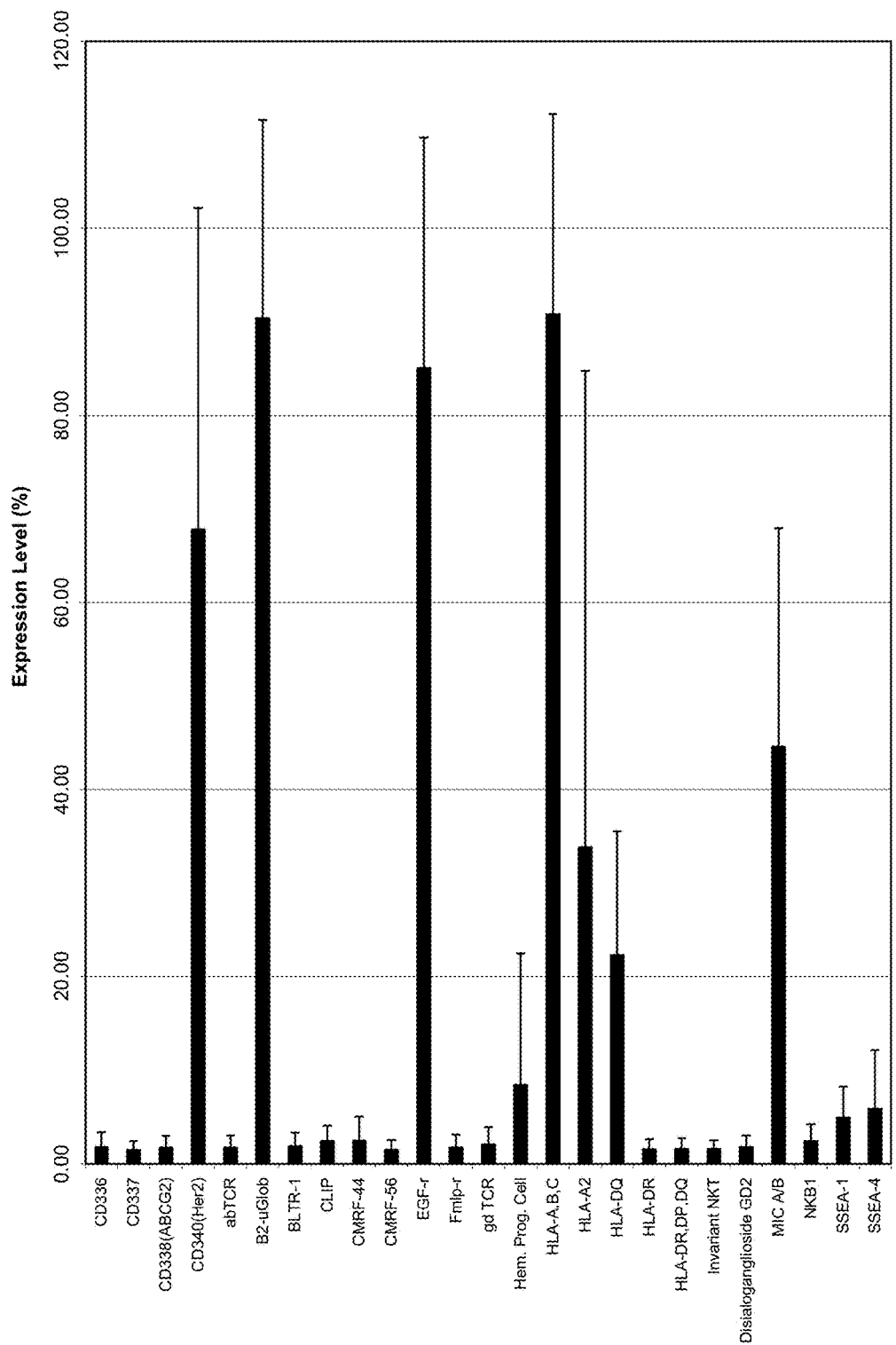
Figure 13J:
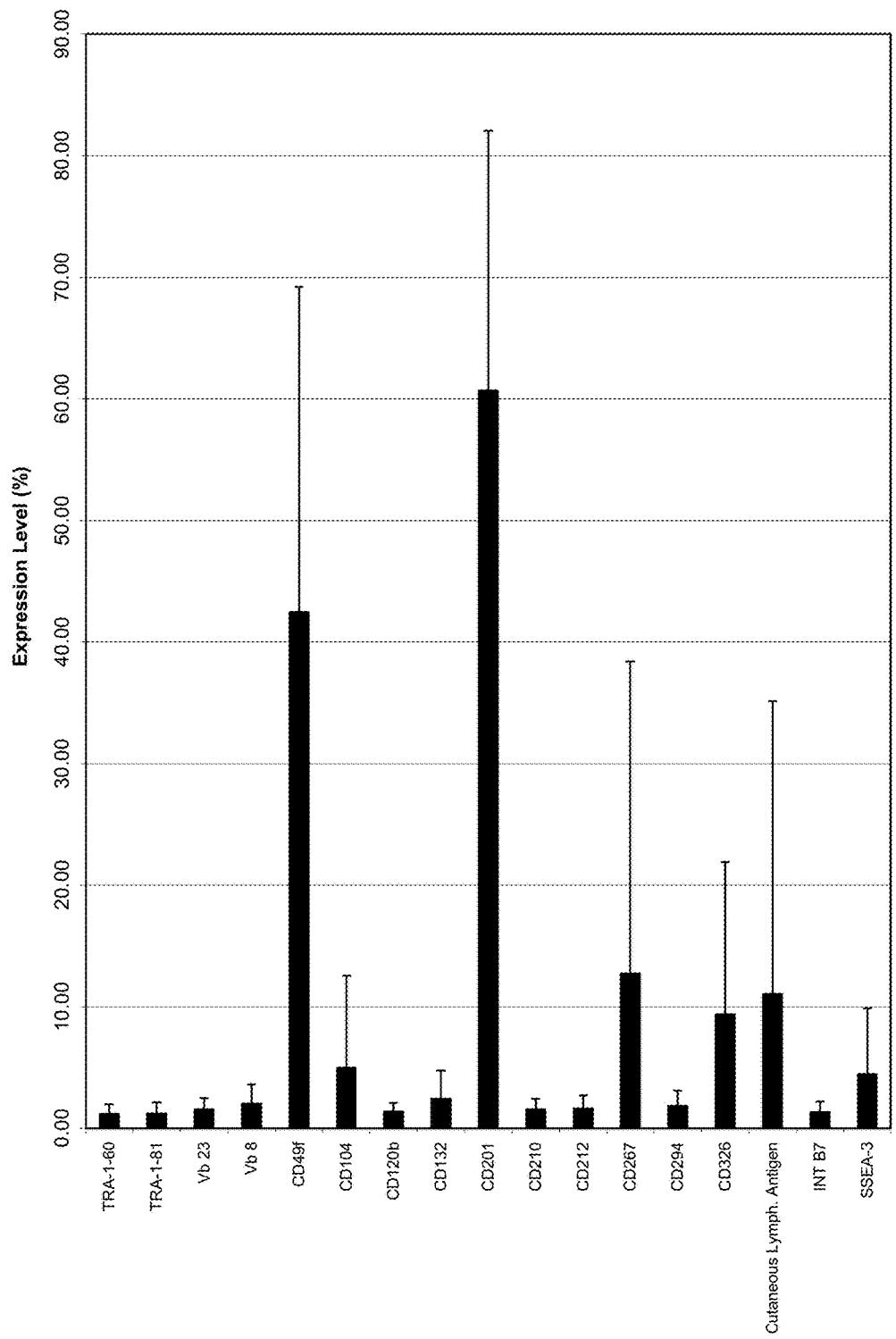

Subsequent testing revealed that inclusion of heparin prior to cryopreservation also aided in the prevention of cell clumps forming during the freeze/thaw process and had no effect on CDC viability (83% viability by Trypan Blue). Clinical samples utilized in the CADUCEUS clinical trial were analyzed as a gold standard and criteria for acceptable levels of cell clumps and particulates were defined based upon those samples (FIG. 11). Those samples were found to contain no particles larger than 150 µm and <1% of particles were larger than 50 µm (Table 6: samples 1 and 2). As discussed above, multiple filtration episodes are used in several embodiments in order to increase the overall efficiency of filtration. Data revealed that CDCs derived from pigs were more susceptible to cell clumps than CDCs derived from humans (Table 6: compare sample 5 to 8, compare sample 9 to 10), CDCs grown without the use of a fibronectin coating were more susceptible to cell clumps than CDCs grown on a fibronectin coating (Table 6: compare sample 5 to 11 (sample 11 passes), compare sample 12 to 13), and the freeze/thaw process itself did not generate cell clumps (Table 6: compare sample 14 to 15, both samples pass; compare sample 16 to 17, both samples pass). The fourth and fifth process changes implemented consisted of re-instituting the use of a fibronectin coating during the CDC expansion phase of manufacturing (as was done for products manufactured in CADUCEUS) and filtering products through a 40 µm mesh prior to cryopreservation to ensure removal of the majority of particles>50 µm. CDCs for clinical use were derived from a human MCB (YKT260, designated for clinical use), not the pig MCB, so as to test the safety of a product designated for clinical use. These CDC did meet the required QC criteria (FIG. 11 and Table 6: sample 17).

TABLE 6

Summary of Cell Clumps and Participates Present in Different CDC Preparations

| Test | Sample | Conditions | % >50 µm | # >150 µm | P/F |
|---|---|---|---|---|---|
| 1. | CAP-1001 from CADUCEUS | Human Fibronectin Fresh (not frozen) | 0.39% | 0% | Pass |
| 2. | CAP-1001 from CADUCEUS | Human Fibronectin Fresh (not frozen) | 0.25% | 0% | Pass |
| 3. | Unfiltered CAP-1002 from 1002-010CAP | Pig HYPERFlasks | 7.75% | 0.0014% | Fail |
| 4. | Filtered CAP-1002 from 1002-010CAP | Pig HYPERFlasks 150 µm post-thaw | 21.2% | 0.0030% | Fail |
| 5. | Unfiltered CAP-1002 from 1002-011CAP | Pig TripleFlasks | 5.16% | 0.10% | Fail |
| 6. | Filtered CAP-1002 from 1002-011CAP | Pig TripleFlasks 150 µm post-thaw | 8.06% | 0.027% | Fail |
| 7. | Test CAP-1002 | Pig TripleFlasks 40 µm post-thaw | 1.85% | 0% | Fail |
| 8. | Test CAP-1002 | Human TripleFlasks | 1.24% | 0.00095% | Fail |
| 9. | Test CAP-1002 | Pig | 7.49% | 0.0050% | Fail |
| 10. | Test CAP-1002 | Human | 0.72% | 0.0036% | Fail |
| 11. | Test CAP-1002 | Pig Fibronectin | 0.99% | 0% | Pass |
| 12. | Test CAP-1002 | Human | 0.84% | 0.00056% | Fail |
| 13. | Test CAP-1002 | Human Fibronectin | 0.12% | 0.00046% | Fail |
| 14. | Test CAP-1002 | Human Pre-freeze | 0.68% | 0% | Pass |
| 15. | Test CAP-1002 | Human 40 µm post-thaw | 0.17% | 0% | Pass |
| 16. | Pre-freeze CAP-1002 from 1002-012CAP | Human Fibronectin 40 µm pre-freeze | 0.19% | 0% | Pass |
| 17. | Post-thaw CAP-1002 from 1002-012CAP | Human Fibronectin 40 µm pre-freeze | 0.11% | 0% | Pass |

Table 7 summarizes the variations in the manufacturing processes implemented the various embodiments disclosed herein.

TABLE 7

Summary of Manufacturing Processes

| Source | Vessel | Coating | Formulation | Filter |
|---|---|---|---|---|
| Pig 0111 | CELLBIND HYPERFlasks | None | No heparin included in cryobags | None for first lot produced Filter pre-administration with pore size of 150 µm for second lot produced |

TABLE 7-continued

Summary of Manufacturing Processes

| Source | Vessel | Coating | Formulation | Filter |
|---|---|---|---|---|
| Pig 0111 | Nunc TripleFlasks | None | 100 U/mL heparin included in cryobags | Filter pre-administration with pore size of 150 μm |
| Human YKT260 | Nunc TripleFlasks | Fibronectin | 100 U/mL heparin included in cryobags | Filter pre-formulation with pore size of 40 μm |

Data collected in a rat model of MI, in which CDCs were derived from two inbred, MHC-mismatched strains and cross-transplanted such that allogeneic and syngeneic CDCs could be compared, showed that allogeneic CDCs induced only a transient, mild, local immune reaction in the heart without histological evidence of rejection or systemic evidence of immunogenicity (Malliaras et al., 2012). Furthermore, improvements in cardiac function were comparable for syngeneic and allogeneic CDCs and were sustained for 6 months, despite waning CDC engraftment levels. Allogeneic CDCs, as well as autologous, are thought to stimulate endogenous regenerative mechanisms (cardiomyocyte cell-cycle re-entry, recruitment of c-Kit+ cells, angiogenesis) via secreted factors (VEGF, IGF-1, HGF) and other as-of-yet unidentified mechanisms of action. The present study as well as the clinical data from CADUCEUS (Makkar, et al., 2012), provide a sounds basis for initiating clinical studies in which post-MI patients will receive infusions of allogeneic CDCs and safety as well as infarct size will be assessed.

To that end, the present study demonstrated a robust manufacturing strategy for allogeneic CDC production. A variety of tissue sources are used, depending on the embodiment, including but not limited to surgical discards, cadaveric donors, tissue donors, organ donors. In several embodiments, however, organ donation is employed, as such a source is readily made compliant with FDA's donor requirements by virtue of being fully tested and screened for relevant communicable diseases, is sterile, and is optimally prepared for use in CDC culture in that the organ is preserved in cold cardioplegia. Tissue donors can also be made readily useful as only grams of tissue are needed for the manufacturing process and the present study shows that tissue can be derived from virtually any region of the heart (e.g. the apex in the case of a valve harvest). In addition, the present study demonstrates that donations from cardiac death donors are viable as a tissue source. UNOS (United Network for Organ Sharing) reported in 2008 that among 832 DCD donors whose other organ were utilized (typically kidneys, liver, and pancreas), only 1 heart was recovered for possible transplant, leaving 831 unused. This sub-source alone could theoretically yield 4 M doses a year at the current manufacturing scale, supplying enough doses for the 1.3 M Americans who suffer from a new or recurrent MI each year and leaving many more available for other indications.

The present study also optimizes techniques to process larger quantities of donor tissue simultaneously and to reduce the man-power necessary for that processing. It shall be appreciated that any amount of tissue from a donor heart, from less than or equal to 40 grams, and up to the entire heart, can be used, depending on the embodiment, especially in view of the positive date presented herein with respect to the viability of short- and long-term tissue storage. Moreover, the data from the present study show that all areas of the heart (and in some embodiments, combinations of areas) can be used to generate CDCs. Finally, the feasibility of CDC cryopreservation was demonstrated as well.

Example 2—Characterization of Explant-Derived Cells and Cardiosphere-Derived Cells The following experiments were performed to more fully characterize the CDCs generated by the optimized production methods disclosed herein, as well as the characteristics of selected intermediate cells, namely, explant derived cells (EDCs), which are the first cell population that is collected from the cultured tissue explant. The characterization provides more detailed understanding of the effects of the methods used to generate cardiospheres and/or CDCs on the resultant genotype and/or phenotype of the generated cardiospheres and/or CDC's. Additionally, the characterization of explant derived cells (EDCs) allows a more full understanding of the effects of the production methods by providing data on the genotype and/or phenotype of intermediate cells in the production process. Moreover, the characterization of the cells at various stages in the production process enables, according to several embodiments, a tailoring of the cells that are obtained by variation of one or more of the method steps.

Characterization was performed on six cell lines derived from six initial cardiac tissue sources. CDCs were generated by the methods disclosed herein. CDCs were subjected to high throughput flow cytometry, by established methods, in order to evaluate expression of 242 different cell surface markers. EDCs from four of the six tissue sources were also subjected to high throughput flow cytometry and the marker expression was compared to the expression of the corresponding CDCs, in order to identify differences in expression between the intermediate (EDC) and final (CDC) cell populations. EDC Line #1 corresponds to CDC Line #1, EDC Line #2 corresponds to CDC Line #2, EDC Line #5 corresponds to CDC Line #5, and EDC Line #6 corresponds to CDC Line #6. The cell surface markers evaluated are listed in Table 9.

Characterization of Explant-Derived Cells

As discussed above explant-derived cells (EDCs) are the first cell population that is collected from the cultured tissue explant, according to the CDC production methods disclosed above. As first intermediate, the characterization of which may lead to further information about how the manufacturing steps affect the CDCs produced, the expression surface markers of four EDC populations were investigated.

Individual marker expression data across each of the four EDC lines and the average of all four lines is provided in Table 10 and graphically shown in FIGS. 12A-12J. For EDCs, Table 10 identifies those markers that are present on greater than 80% of the EDCs (on average) with black shading in the appropriate cell in the column entitled "Marker". Those markers that are present on 20-80% of EDCs are identified by underlining. Those markers that are present on less than 20% of the EDCs are unshaded. More detailed discussion of EDC marker profiles is provided below.

Characterization of Cardiosphere-Derived Cells

As discussed above for EDCs, CDCs were also characterized in the same fashion. Flow cytometry was used to characterize 242 surface markers from six human CDC lines (four of which correspond to the four EDC populations characterized above). Individual marker expression data across each of the six CDC lines and the average of all six lines is provided in Table 11 and graphically shown in FIGS. 13A-13J. Table 11 identifies those markers that are present on greater than 80% of the CDCs (on average) with black shading in the appropriate cell in the column entitled "Marker". Those markers that are present on 20-80% of CDCs are identified by underlining. Those markers that are present on less than 20% of the CDCs are unshaded.

As discussed in more detail below, the present experimental analysis identified "panels" of markers that are used, in several embodiments, to specifically identify cells as being CDCs. Additionally, in several embodiments, these marker panels facilitate gaining a deeper understanding of how various aspects of the protocols described herein impact the resultant cell populations (whether intermediate or final cell populations) and aid in understanding alterations in characteristics of those populations, changes in specificity of isolation of the cells, and/or other sources of potential variability among CDC production runs. Additionally, in several embodiments, the markers are used to characterize the purity of CDCs, and/or to distinguish CDCs from earlier cellular intermediates.

Approximately 30 markers were identified that are expressed by greater than about 80% of CDCs (black in Table 11). In several embodiments, one or more of these markers is present on greater than about 80%, greater than about 85%, greater than about 90%, greater than about 92%, greater than about 94%, greater than about 96%, greater than about 97%, greater than about 98%, greater than about 99%, greater than about 99.5%, greater than about 99%.8, or greater than about 99.9% of CDCs in a population. Certain of these markers appear to be related to putative mechanisms of action of the CDCs (e.g., these markers are associated with certain pathways that, in several embodiments, may play a role in the therapeutic efficacy of CDCs). These markers can be used, in several embodiments, to define what cell populations can be considered to be CDC populations (e.g., cells that are processed by the methods disclosed herein and expressing one or more of these markers are identifiable as CDCs).

Approximately 30 markers were identified that are expressed by a more variable percentage of the CDCs (e.g., from about 20% to about 80%; underlined in Table 11). Nearly 60 markers were identified that are expressed at variable levels, resulting in average expression with standard deviations greater than 10% (italicized in Table 11). The variable expression of these markers provides additional information about the potential batch to batch variability of CDC production. In some embodiments, this variation is due to tissue source-specific variations (e.g., genetic variation from donor to donor). The variability can also, depending on the embodiment, lead to correlations with variations in potency of the cells, induction of immune response, and other clinically relevant considerations. Over 175 markers were identified as being expressed by less than 20% of CDCs (unshaded in Table 11). The absence of these markers on a substantial portion of CDCs is useful, in several embodiments, to evaluate the purity of a given CDC population produced according to the methods disclosed herein.

Markers Defining CDCs

As discussed above, approximately 30 of the cell surface markers evaluated are expressed on greater than approximately 80% of CDCs. Further analysis of the markers indicates that five markers are potentially related to mechanisms of action of CDCs and three markers are ligands to receptors that are known to be upregulated after myocardial infarction. Seven markers are part of the integrin family, while four markers are related to immunogenicity signaling pathways. Three of the markers are correlated with potency of CDCs, and seven markers are related growth factor and/or hormone receptors, which may also relate back to potential paracrine-based mechanisms of action of CDCs.

Markers Related to Possible CDC Mechanisms of Action

Certain of the markers identified in the CDC screen are associated with possible mechanisms of action of CDCs. In the CDC lines tested, greater than 99% of the CDCs expressed CD105 (99.5±0.5%; also known as endoglin). CD105 is the regulatory component of the TGFβ receptor complex. It functions in this capacity by associating with TGFβ receptor subtypes I and II, which, when complexed together bind TGF-b1 and TGF-b3 with high affinity. Several TGFβ family members are significantly induced in the infarcted myocardium and may play a role in one or more of infarct healing, cardiac repair and/or left ventricular remodeling. Thus, in addition to its effects in angiogenesis, hematopoiesis, and cardiac development CD105 may be a major player in the therapeutic efficacy of CDCs. CD105 is also expressed at high levels on active endothelial cells and mesenchymal stem cells. Additionally, increases in the soluble form of CD105 can attenuate cardiac fibrosis. As such, administration of a population of cells expressing high levels of CD105, such as CDCs, may facilitate the repair and/or regeneration of cardiac tissue through CD105-associated signaling pathways.

In the CDC lines tested, CD81 was expressed on greater than 97% of the CDCs (98.2±2.7%). CD81 is also referred to as Target of the AntiProliferative Antibody 1 (TAPA-1) and Tetraspanin-28 (Tspan-28). CD81 encodes a protein that is a member of the transmembrane 4 superfamily. The encoded protein of CD81 is a glycoprotein, that complexes with integrins, and thus is associated with regulation of cell development, cell activation, cell growth and cell motility. CD81 has also been found to be expressed on certain types of mesenchymal stem cells, such as, for example, mesenchymal stem cells derived from cardiac tissue and those derived from cardiomyogenic adipose tissue.

In the cell lines tested, CD151 was expressed on greater than 99% of the CDCs (99.6±0.3%). CD151 also encodes a protein of the transmembrane 4 superfamily (also referred to as tetraspanin). These proteins mediate certain signal transduction events involved in cell development, cell adhesion, cell motility, cell growth, and cell activation. CD151 is also involved in angiogenesis; overexpression of CD151 has been associated with induction of cardiac neovascularization. CD151 is expressed on endothelial cells and is known to complex with CD9, ICAM-1 (also referred to as CD54), and VCAM-1 (also referred to as CD106, which, in several embodiments, is not expressed on CDCs) during inflammation in order to recruit leukocytes.

In the cell lines tested, CD9 was expressed on greater than 98% of the CDCs (98.9±1.4%). CD9 also encodes proteins of the transmembrane 4 superfamily. CD9 is also known as MRP-1 (motility-related protein-1) and/or p24 antigen. CD9 is associated with modulation of cell adhesion, and is also involved in cell migration/motility. CD9 can play a role in cell differentiation and/or cell proliferation and also may function, depending on the context, as a tumor suppressor. CD9 has also been associated with down regulation of Wnt gene expression. In addition to expression on CDCs, CD9 is expressed on exosomes, endothelial cells, and mast cells. In several embodiments, in addition to sharing expression of CD9 with exosomes, CDCs also share with exosomes expression of CD81. Similarly, endothelial cells also express CD151, CD54 and CD106. In several embodiments, CDCs also express one or more of CD151, CD54 and CD106. In some embodiments, however, CDCs do not express CD106. Mast cells are also known to express CD117, which, in several embodiments, is not expressed by CDCs.

In the cell lines tested, CD147 was expressed on greater than 98% of the CDCs (98.6±2.1%). CD147 is also referred to as extracellular matrix metalloproteinase inducer (EMM-PRIN) and/or basigin. CD147 stimulates production and activation of a variety of matrix metalloproteinases. In some cases, this activation results in cardiac remodeling (although its effect may vary in other tissues, such as, for example, promotion of tumor cell invasion by alteration of interstitial collagenase). CD147 is present on cardiac progenitor cells during early development, and also present on exosomes that are derived from cardiac progenitor cells. Of particular interest in the field of cardiac therapy, CD147 expression in cardiomyocytes is significantly increased after myocardial infarction or heart failure. Experimental evidence shows that overexpression of CD leads to adverse cardiac remodeling.

In several embodiments, the presence of one or more of these transmembrane 4 superfamily markers on the CDCs engender the CDCs with one or more aspects of their therapeutic effects (for example, adhesion of the CDCs to cardiac tissue post-administration, homing of the CDCs to damaged or diseased cardiac tissue; angiogenesis, and the like).

Thus, these data demonstrate that, in several embodiments, CDCs express one or more members of the transmembrane 4 superfamily and/or certain molecules playing a role in TGFβ-mediated signaling. In some embodiments, these markers, either individually or in combination (e.g., two or more, three or more, etc.), are expressed on greater than about 80%, greater than about 85%, greater than about 90%, greater than about 95%, greater than about 97%, greater than about 98%, and/or greater than about 99% of CDCs. Thus, in several embodiments, based on the detection of one or more of these markers, a cell population produced by the methods disclosed herein can be positively identified as a CDC population.

Ligands for Markers of Myocardial Infarction

Figure 14:
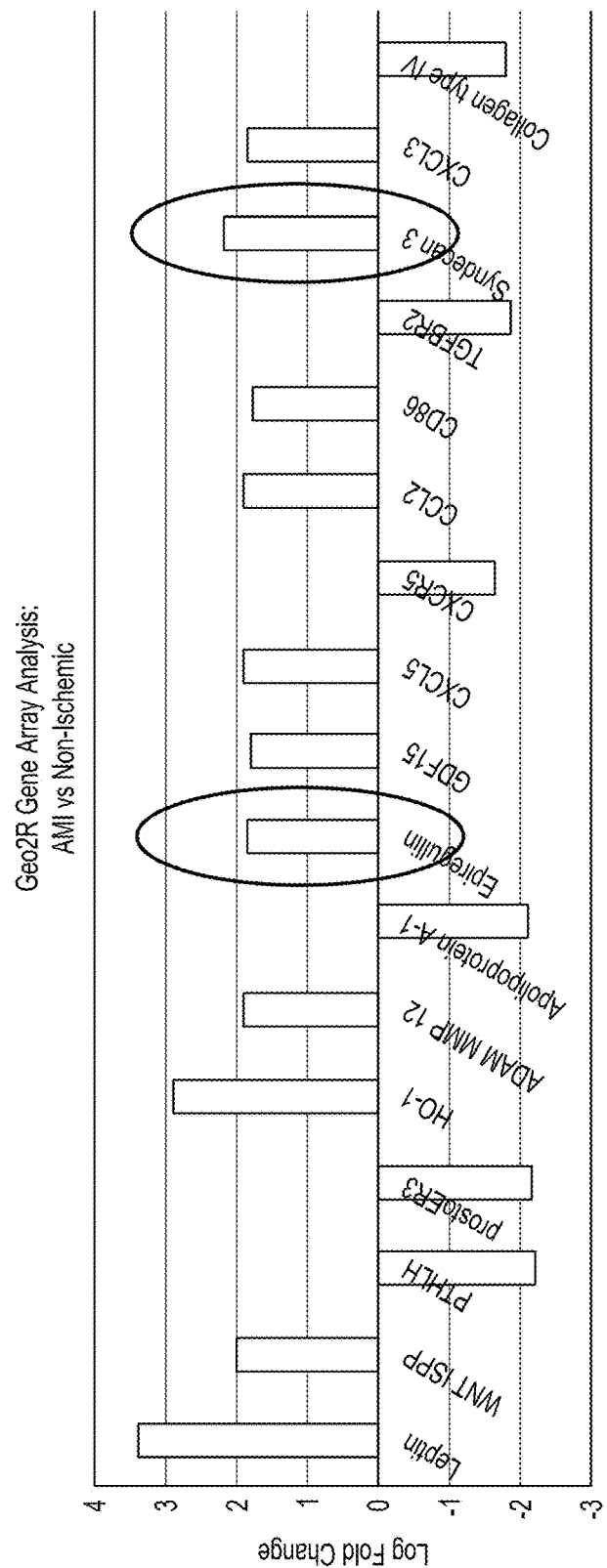
FIG. 14 depicts identification of certain markers expressed on CDCs that are ligands for markers of myocardial infarction.

FIG. 14 depicts data, identifying genes whose expression is changed in response to a myocardial infarction. Several of those genes are known to be ligands (or receptors) for some of the cell markers studied on the CDC lines generated. For example, epiregulin, increased nearly 2-fold in response to myocardial infarction, is a ligand of the epidermal growth factor receptor (EGF-r), which is expressed on approximately 85% of the CDCs evaluated (85.1±24.6%; range of 48.4-99.6%). The EGF-r is a tyrosine kinase and signaling through the receptor results in activation of a variety of different signal pathways, such as, for example, mitogen-activated protein kinase, phosphoinositide 3-kinase, protein kinase C, STAT (signal transducer and activator of transcription) and phospholipase C, among others. In general, EGF-r and the pathways it activates are involved in regulation of angiogenesis, cell proliferation and/or reduction in apoptosis. Thus, the presence of epiregulin in the post-MI heart may activate the EGF-r on CDCs and initiate a cascade of signaling through the EGF-r that results in increased angiogenesis and/or reduced apoptosis. Either (or both) of these effects, alone or in conjunction with other signaling pathways, could impart increased function capacity to cardiac tissue (e.g., via improved blood flow) and/or increased tissue viability (less direct cell death and less adverse effects from local apoptotic signals that kill other cells).

Syndecan 3 functions as an accessory protein to assist in the binding of growth factors to their receptors is also upregulated over 2-fold in response to myocardial infarction. Syndecan 3 also functions as an accessory in certain cell adhesion reactions, and facilitates the actions of certain integrins, including, but not limited to β1 integrin (also known as CD29) and α5 integrin (also known as CD49e). Integrins have a variety of roles, depending on the specific biological processes, but they are generally associated with cell migration during development, wound healing, cell differentiation, and apoptosis. β1 integrin is expressed on approximately 90% of CDCs studied (91.0±7.3%; range of 84.1-99.7%) and α5 integrin is present on over 99% (99.3±1.1%; range of 97.4-99.8%) of the CDCs evaluated. Thus, the presence of increased levels of syndecan 3 in the post-MI heart may increase its interaction with β1 integrin and/or α5 integrin, which can result in the facilitation of migration and/or engraftment of CDCs into the myocardium and/or the reduction of apoptosis of CDCs following administration.

Several additional integrin molecules are expressed by CDCs at relatively high levels. For example, the adhesion marker CD49d is expressed on over 80% of CDCs (84.6±11.4%; range of 71.0-99.8%). CD49d encodes a subunit of the integrin alpha (type 4), which is a portion of the receptor involved in lymphocyte homing.

CD51/61 is expressed on over 95% of CDCs (average of 98.4±3.1%, range of 92.8-99.9%). It encodes the αv integrin subunit. CD61 is also present on over 95% of CDCs (average of 98.8±%1.9; range of 95.0-99.9%). It encodes the β3 integrin subunit.

CD49c is expressed on over 95% of CDCs evaluated (average of 99.6±0.5%; range of 98.7-99.9%). CD49c encodes the α3 integrin and is expressed on a variety of other adhesion cells, such as endothelial cells, epithelial cells and fibroblasts.

CD49b is expressed on over 95% of CDCs evaluated (average of 99.4±0.7%; range of 98.0-99.8%). CD49b encodes the α2 integrin subunit and together with other integrins, plays a role in cell adhesion and cell-surface mediated signaling. In view of the presence of several adhesion molecules on a very high percentage of all CDCs tested, the CDCs, in several embodiments, facilitate the functional and anatomical repair and/or regeneration of cardiac tissue by virtue of their ability to adhere to (e.g., engraft) or stimulate (e.g., cell surface and/or paracrine signaling) the cardiac cells and/or the CDCs.

Association with Immunologic Markers

Approximately 90% of CDCs express CD274, which is also known as programmed death ligand 1 (PD-L1; 89.9±10.5%; range of 74.2-98.6%). CD274 plays a role in immune system suppression during certain events where there is an increased risk of immune rejection, such as, for example, pregnancy, tissue allografts, and autoimmune disease. While the immune system typically reacts to foreign antigens by triggering a proliferation of antigen-specific CD8+ T cell, the interaction of CD274/PD-L1 ligand with its receptor, PD-1 receptor, transmits an inhibitory signal which reduces the proliferation of these CD8+ T cells. Thus, the relatively high levels of CD274 expressed by CDCs may impart an enhanced ability to reduce/avoid an immune response upon administration. CD274/PD-L1 has been shown to be necessary to the immune suppressive and/or modulatory effects of cardiac progenitor cells. In several embodiments, this characteristic is especially advantageous, for example, when the CDCs are used in allogeneic administrations.

CD119 encodes one ligand-binding chain (the alpha chain) of the heterodimeric gamma interferon receptor (INFγ-R), which is found on macrophages and is expressed on approximately 40% of CDCs, on average (average 38.4±26.4%; range of 8.1-62.1%). The INFγ-R also interacts with interferon gamma, which is intricately involved in innate and adaptive immune responses. The expression of CD119 on CDCs suggests that CDCs may have the capacity to alter the immune response that would be expected when CDCs are administered. In several embodiments, the alteration results in an enhanced engraftment, retention, therapeutic effect of the CDCs, and/or alteration of any immune response mounted to CDC administration.

CD142 (also known as Tissue Factor) is expressed on over 50% of CDCs on average (average of 56.3±24.7%; range of 16.7-91%). CD142 is most commonly known for its role in blood coagulation (CD142 complexing with Factor VIIa catalyzes the conversion of inactive Factor X into active Factor Xa). However, CD142 is also associated with both angiogenesis and apoptosis. CD142 is expressed by cells that, under normal circumstances, are not exposed to blood flow (such as smooth muscle cells or fibroblasts). If a physical injury, for example a rupture of an atherosclerotic plaque or an ischemic event that damages cells, exposes CD142 expressing cells to blood flow, complex formation between CD142 and Factor VII can occur, which in turn leads to activation of Factor VII (then known as Factor VIIa). The CD142/Factor VIIa complex can then impact angiogenesis and/or apoptosis.

CD80, also known as B7-1 is expressed on less than about 20% of CDCs evaluated (average of 17.5±13.9%; range of 1.4-38.0%). CD80 is typically found on activated B cells and monocytes and when expressed, provides a stimulatory signal that in needed for activation and survival of T cells. CD80 acts as the ligand for one of two receptors on the surface of T cells, either CD28 (promotes autoregulation and intercellular association) or CTLA-4 (reduction of T-cell regulation and cellular dissociation). The relatively low level of CD80 expression suggests that, in several embodiments, CDCs will induce limited activity by T cells, which again may impart to CDCs an advantage when allogeneic administrations are performed.

Markers Correlated with Therapeutic Potency

Figures 15A, 15B, 15C:
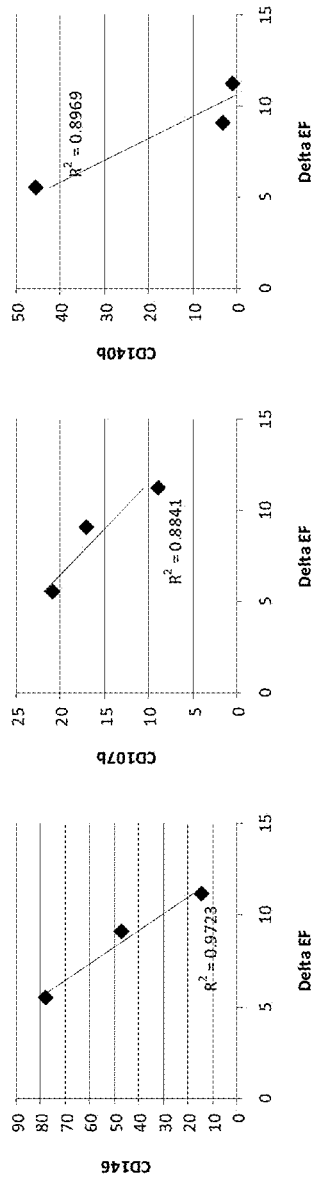
FIGS. 15A-15C depict the negative correlation of CD146 (A), CD107b (B), and CD140b expression with the change in ejection fraction (representative of one aspect of CDC therapeutic potency).
Figure 16A:
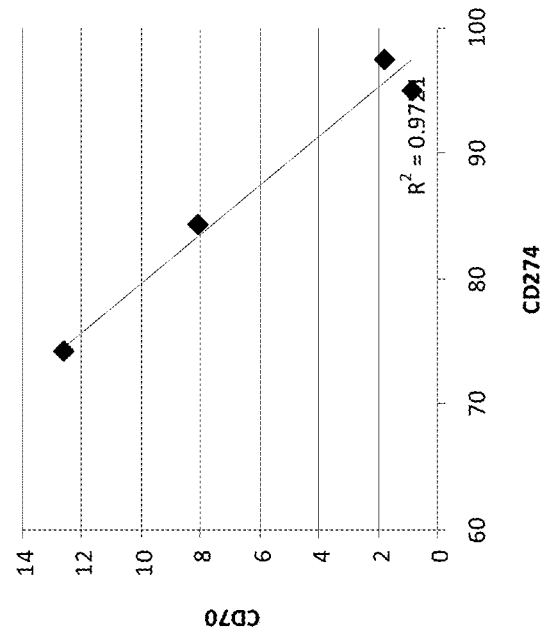
FIGS. 16A-16B depicts correlation in expression between various immunologic markers on CDCs.
Figure 16B:
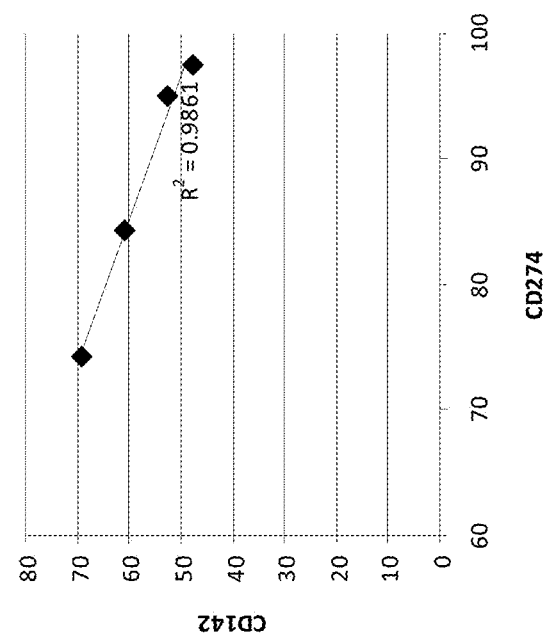
Figure 17A:
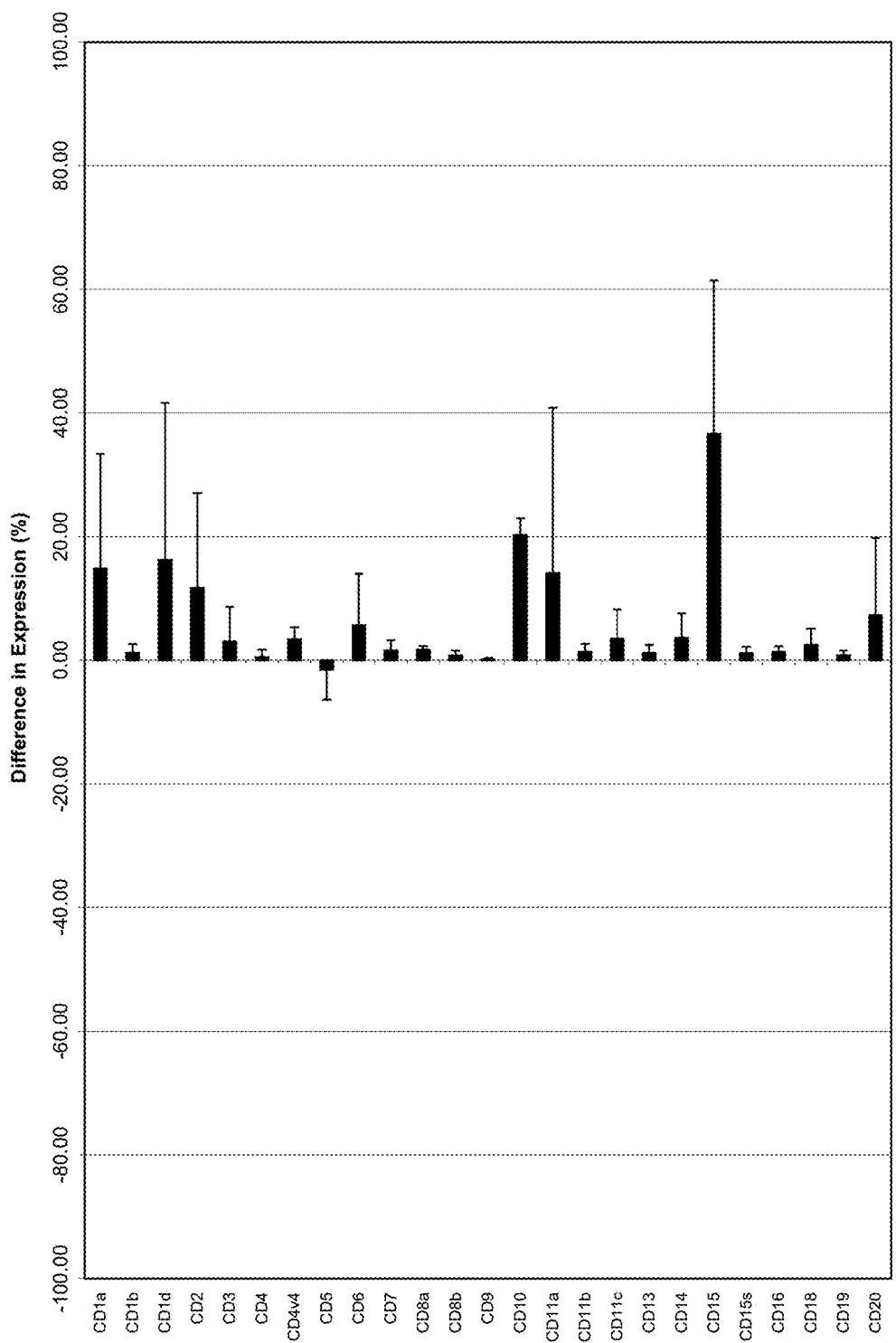
FIGS. 17A-17J depict the average difference in expression levels of 242 cell surface markers on EDCs from four separate production runs as compared to the marker expression on the corresponding CDCs.
Figure 17B:
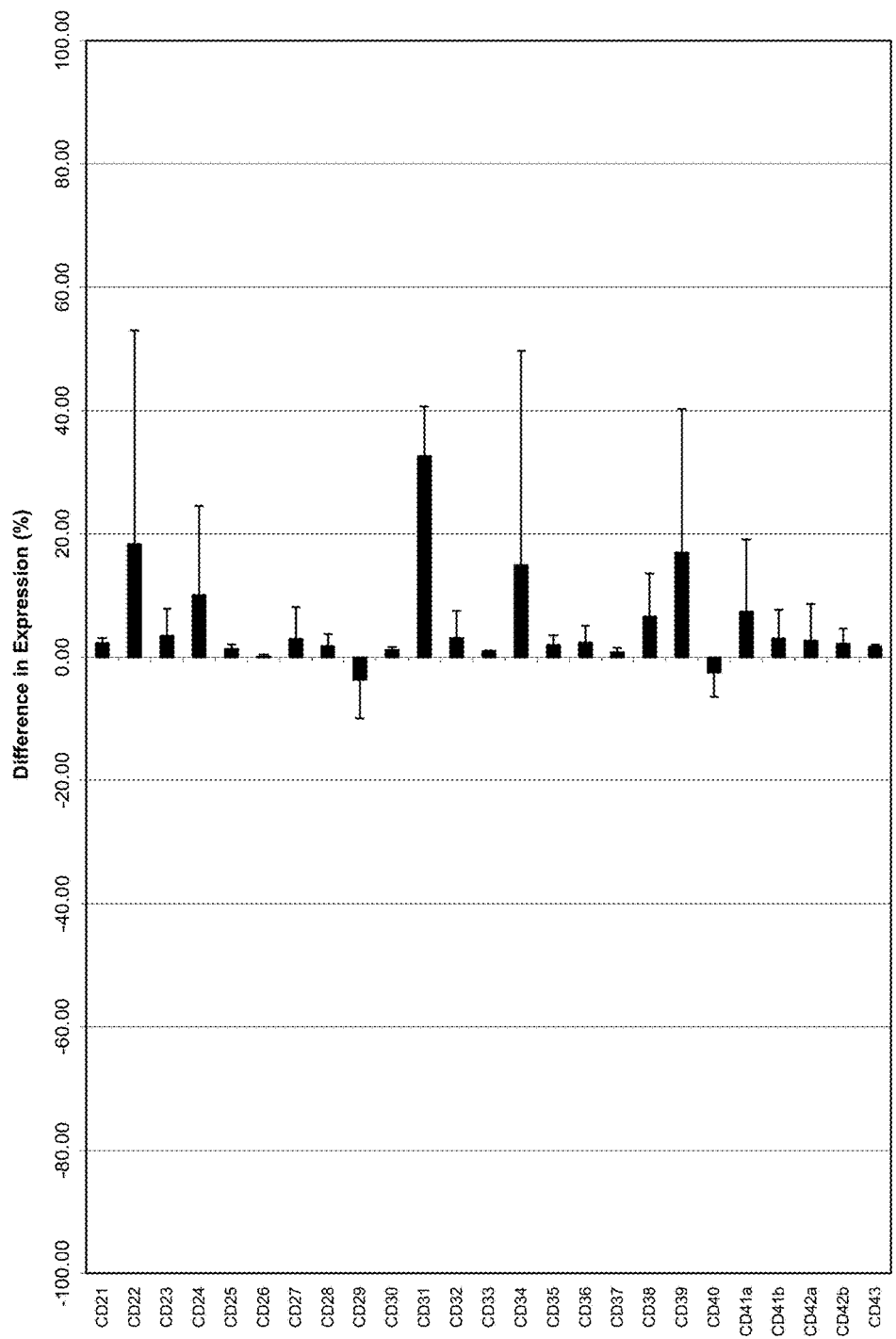
Figure 17C:
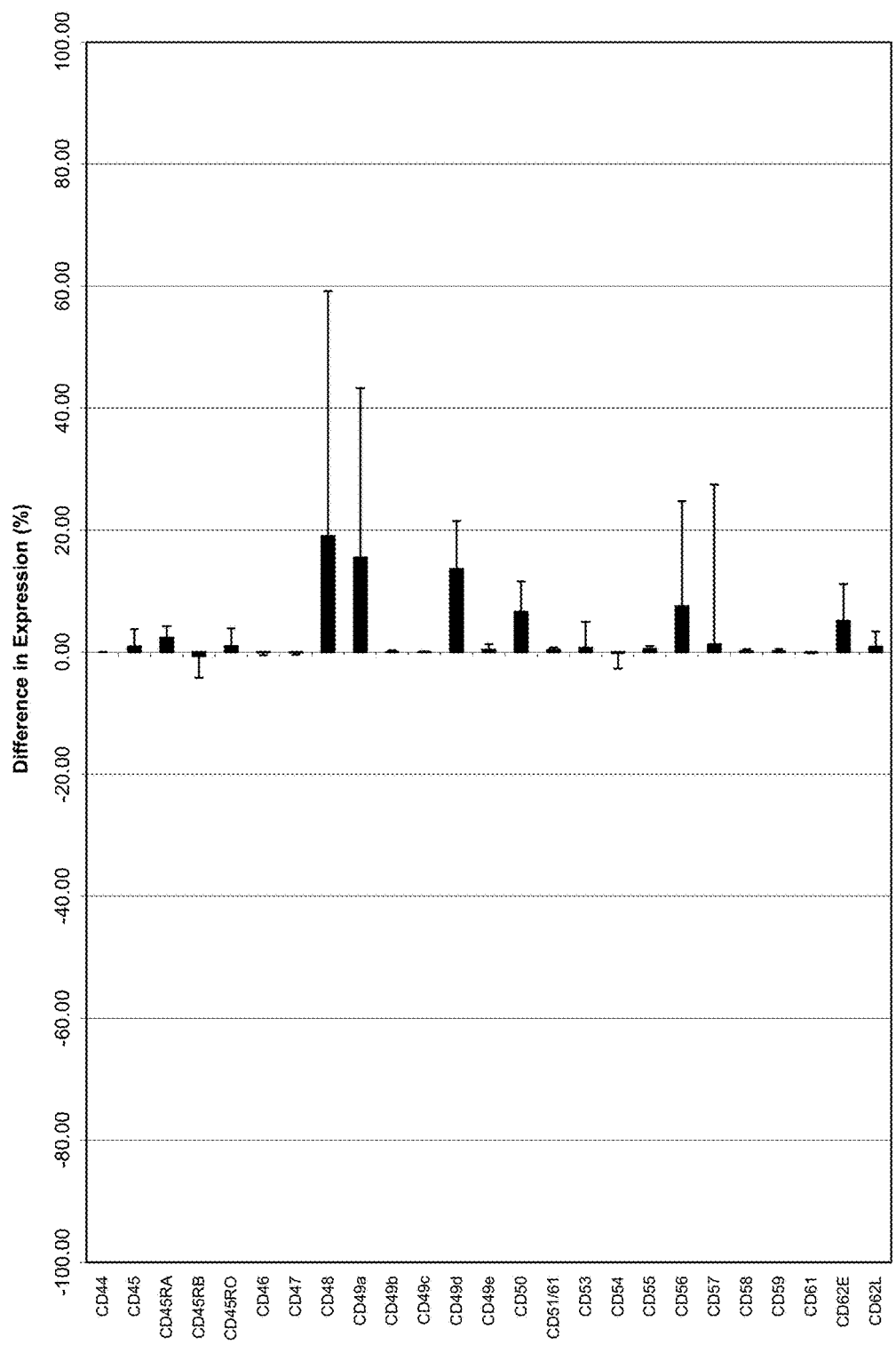
Figure 17D:
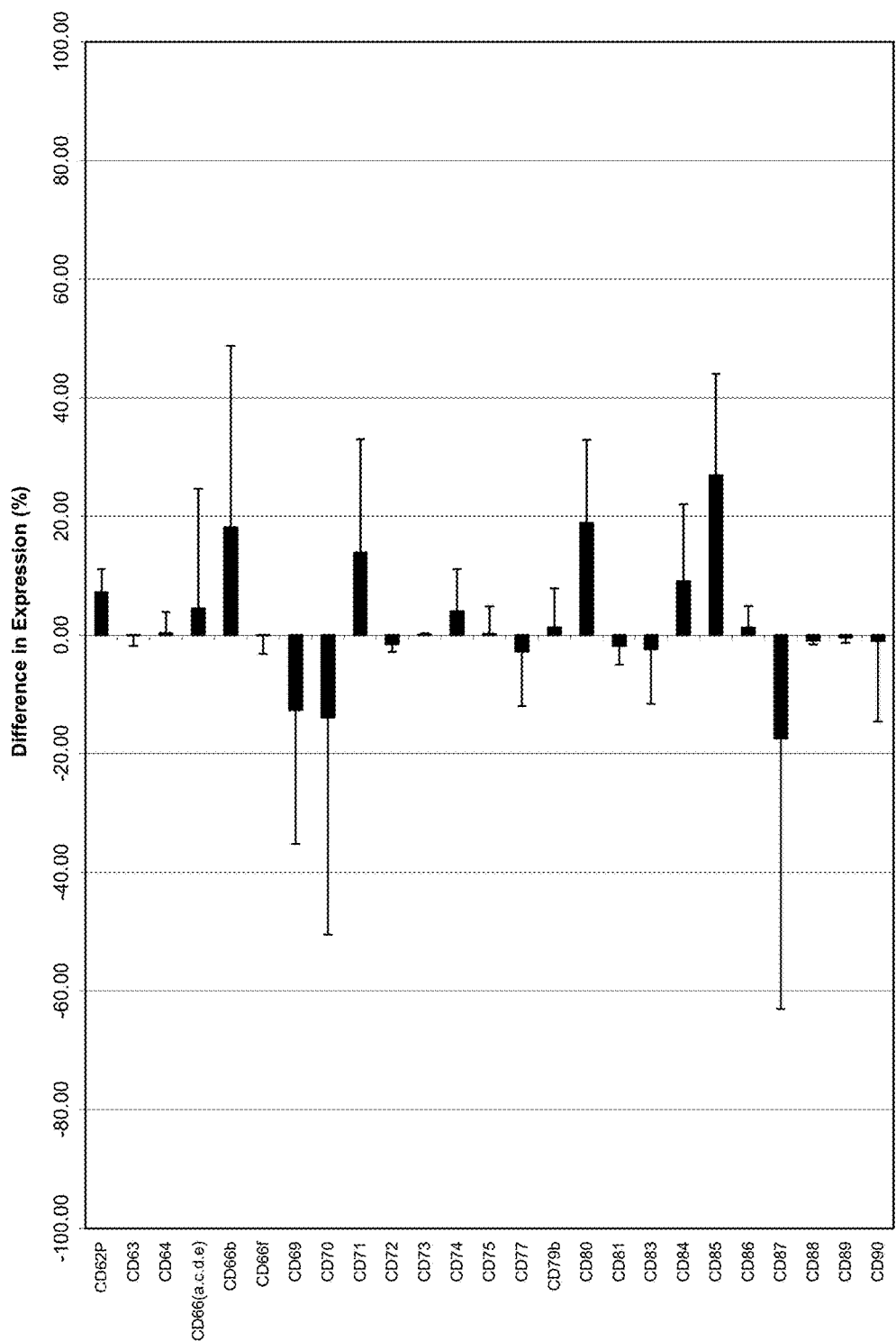
Figure 17E:
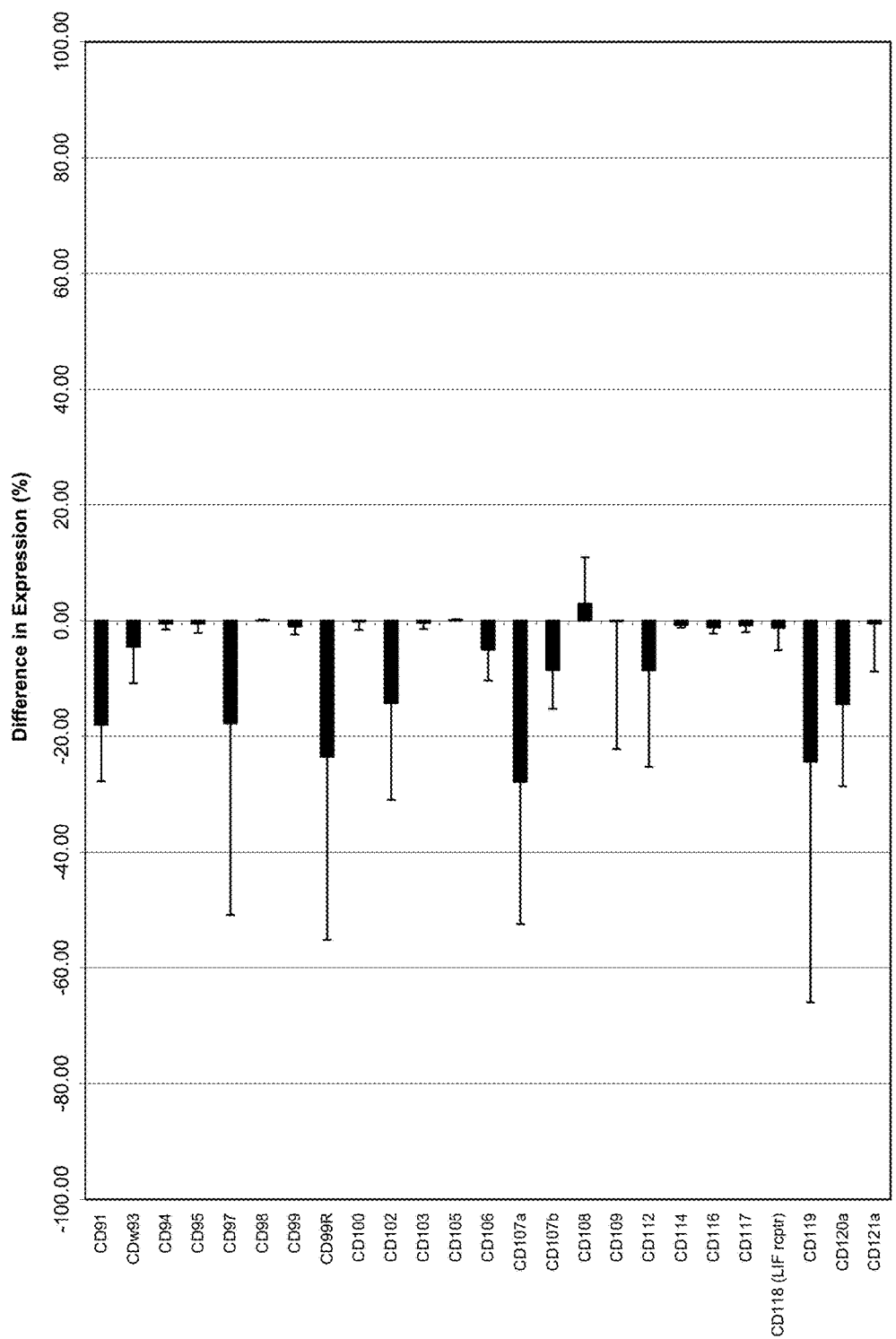
Figure 17F:
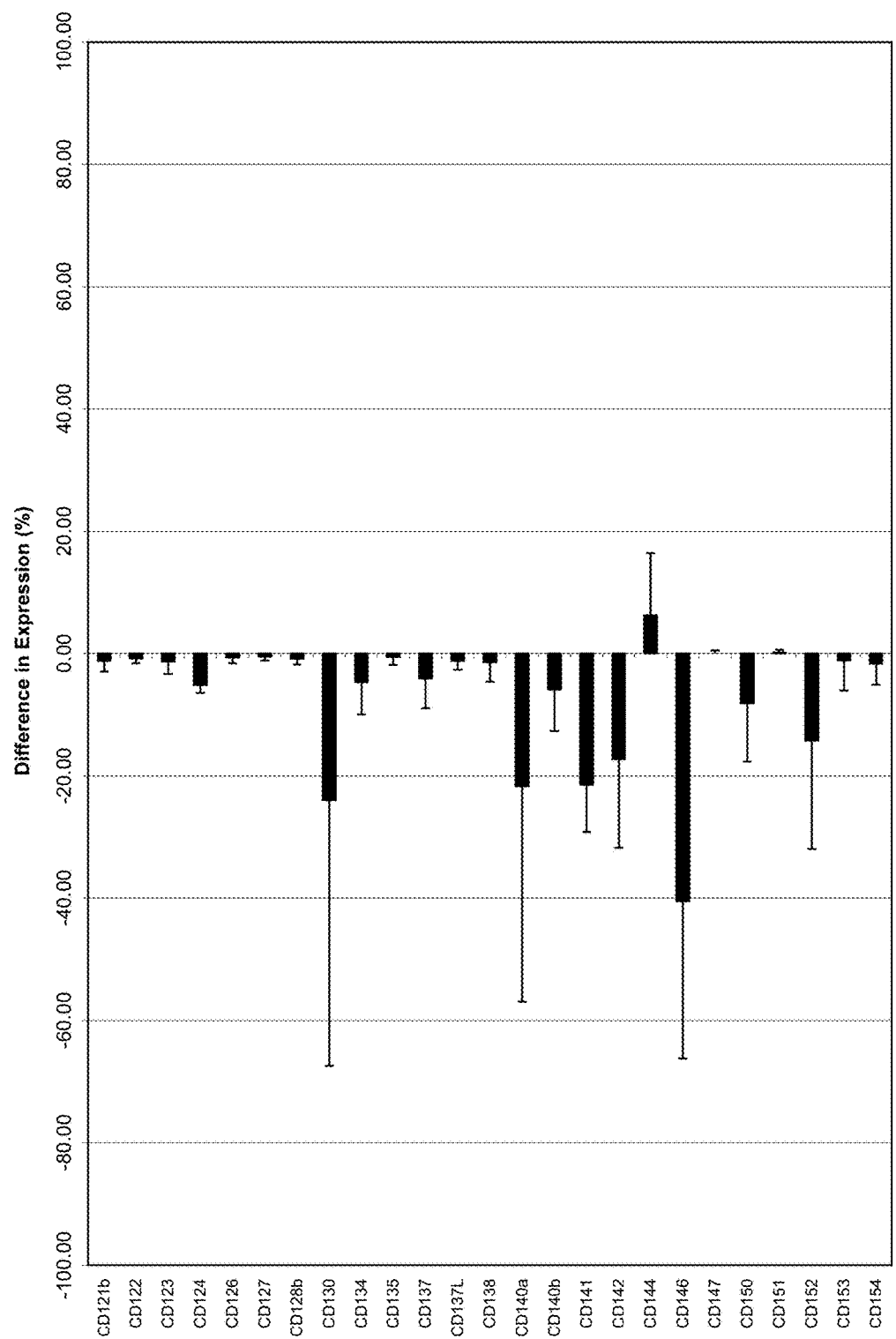
Figure 17G:
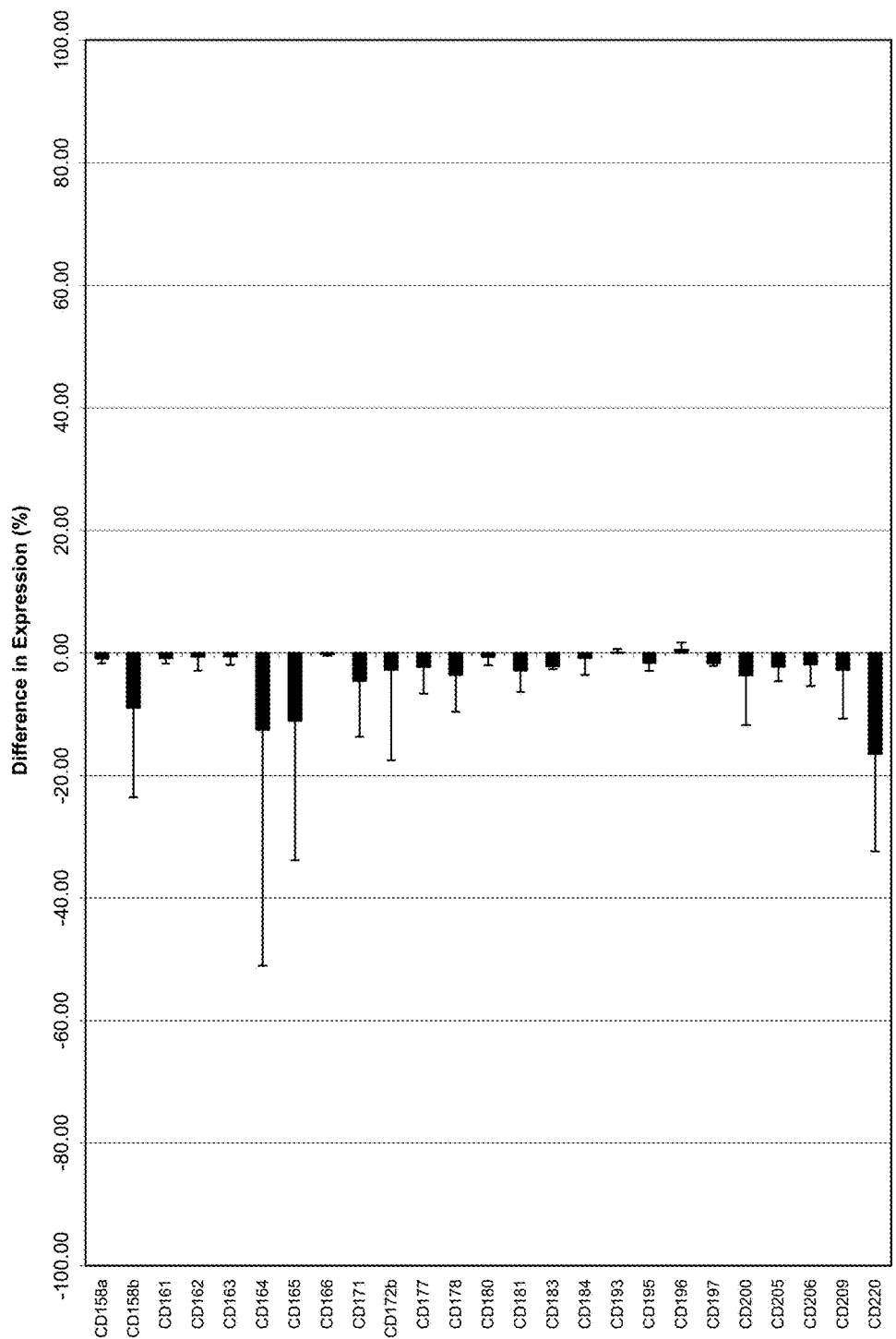
Figure 17H:
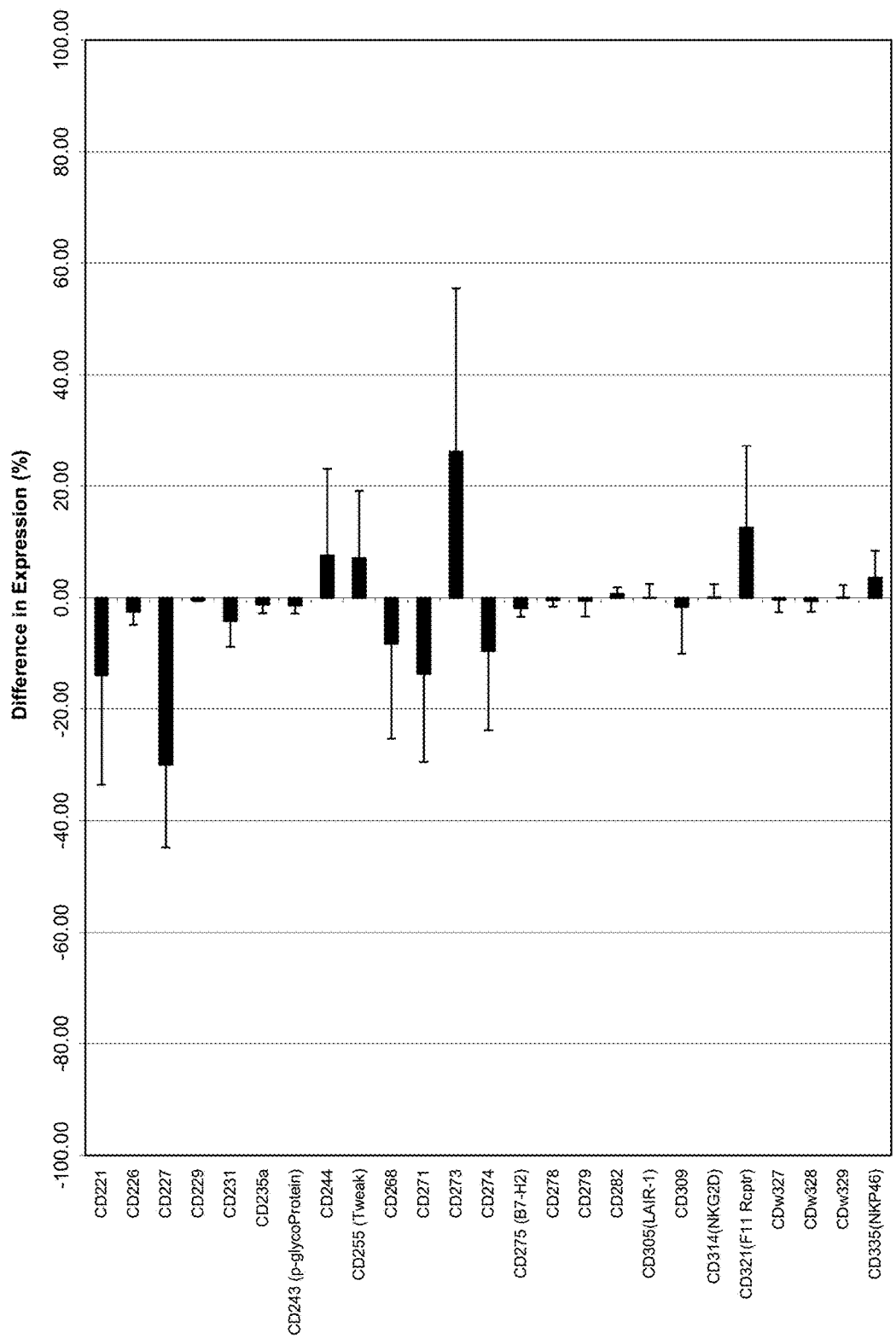
Figure 17I:
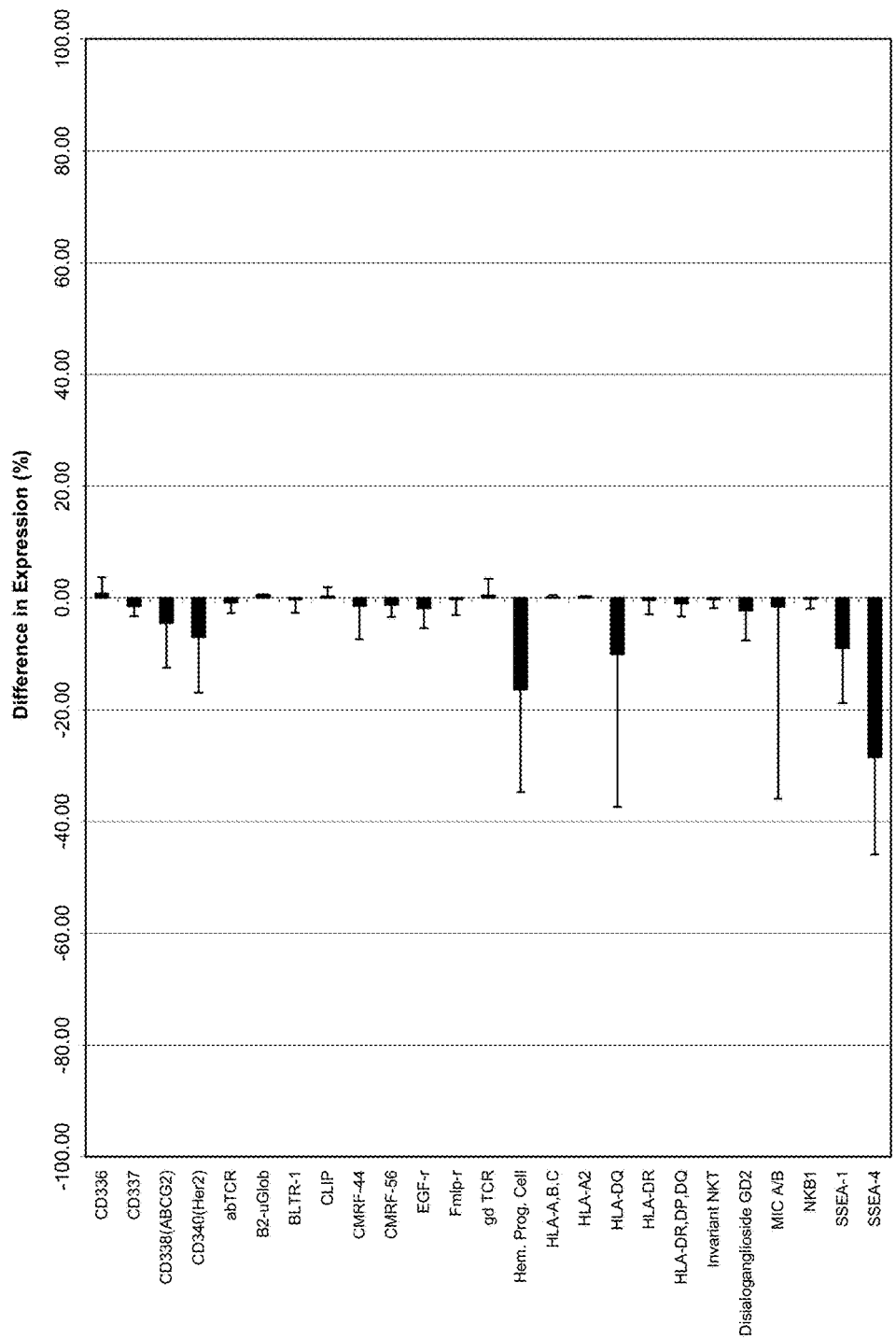
Figure 17J:
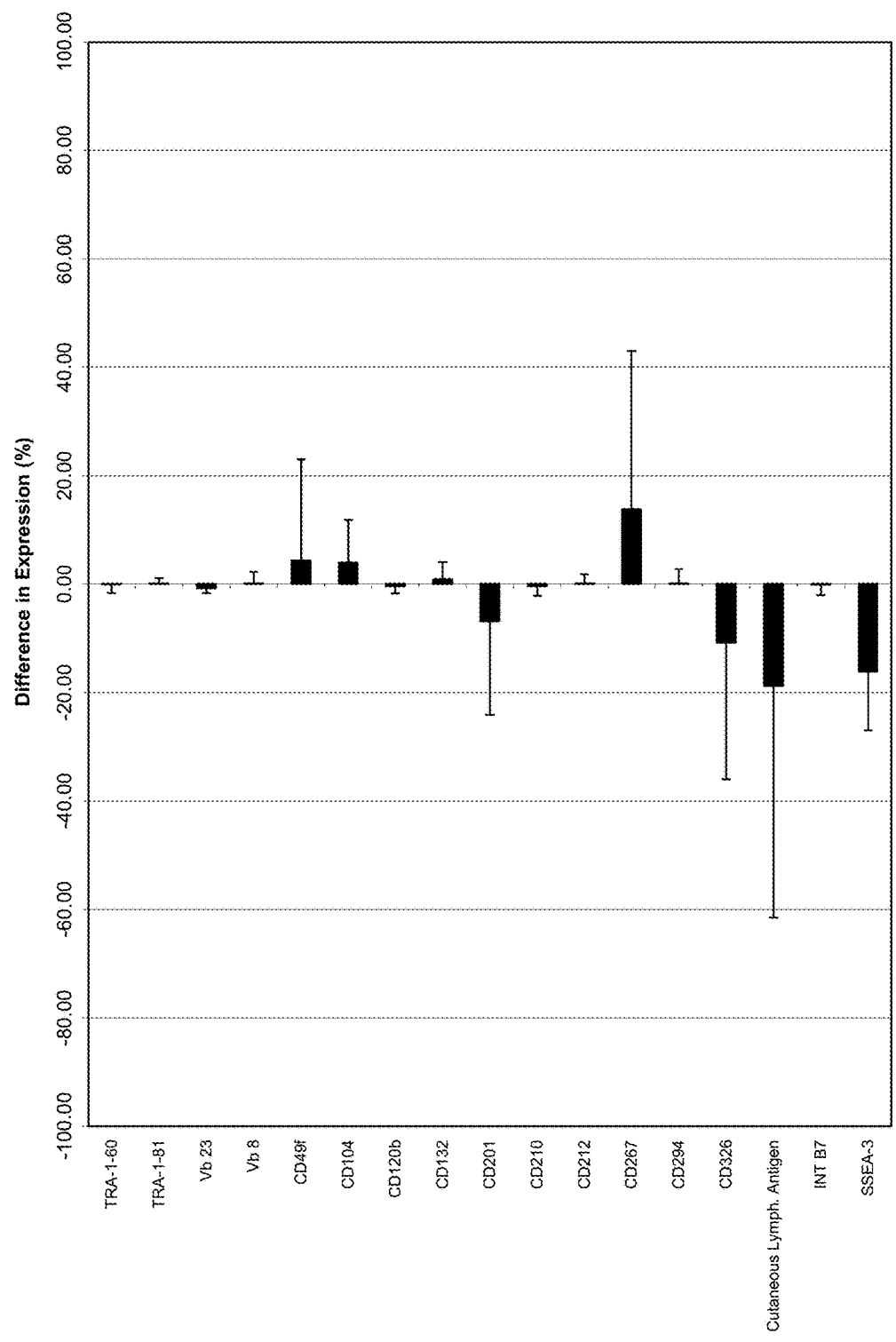

Another group of markers was correlated with the therapeutic potency of CDCs. Therapeutic potency is represented by the change in ejection fraction (the X axis on FIGS. 15A-15C), that is the ejection fraction of the subject after myocardial infarction, as compared to the ejection fraction of the subject after treatment with CDCs. Expression levels of CD146, CD107B, and CD140b (FIGS. 15A, B, and C, respectively) are each decreased as therapeutic efficacy of CDC's increases. CD146 is also known as melanoma cell adhesion molecule (MCAM). At the lowest level of therapeutic potency, CD146 was expressed on nearly 80% of the CDC's, while at the highest therapeutic potency CD146, was expressed on approximately 14% of the CDCs (average of 48.0±22.9%; range of 14.1-77.9%). CD146 is used as a marker for endothelial cells, in some contexts, and appears to be associated with the formation of the junction of endothelial cells with the actin cytoskeleton. CD146 is also used as a marker for pericytes in several organs.

Similarly, CD107b was expressed on approximately 5% of CDCs at the highest level of therapeutic potency and over 20%, at the lowest level of therapeutic potency (12.0±5.9%, range of 5.5-20.9%). CD107b, or, lysosome-associated membrane protein 2 (LAMP-2) encodes a member in glycoprotein and appears to be involved in providing carbohydrates as a ligand to selectins.

Finally, CD140b (also known as platelet derived growth factor beta; PDGFRβ) was expressed on almost 50% of the CDCs at the lowest level of therapeutic potency and expression was nearly absent when CDCs resulted in the highest level of therapeutic potency (average of 9.8±17.6%, range of 0.9-45.6%). CD140b encodes a cell surface tyrosine kinase receptor that interacts with various members of the platelet derived growth factor family. Such growth factors typically function as mitogens for mesenchymal cells.

Additional Markers

Several other growth factor receptors were found to be expressed on CDCs at moderate to low levels. For example, CD140a, also known as the platelet derived growth factor receptor alpha, is expressed on approximately 40% of CDCs (average 45.7±22.1%; range of 28.0-75%). Similar in its expression level on CDCs is CD221 (also known as insulin-like growth factor type −1 receptor) which is expressed at slightly lower levels than CD140a (average of 42.7±28.2%, range of 4.2-75.7%). CD220, the insulin receptor, is expressed on about 15% of CDCs (average of 24.3±24.4%, range of 3.1-69.2%). CD120a, the tumor necrosis factor receptor type 1 is expressed on less than about 15% of CDCs (average of 15.3±4.7%, range of 9.6-15.2%). These data suggest that CDCs may be moderately responsive to certain growth factors, such as insulin-like growth factor type −1 or PDGF while perhaps being less responsive to other growth factors like tumor necrosis factor or insulin. The varied expression may, depending on the embodiment, not necessarily be directed correlated with the function or responsiveness to a particular growth factor, but rather with a larger signaling transduction cascade.

Comparison of Marker Expression in EDCs as Compared to CDCs

In comparing the final end product of the methods discussed above, namely the CDCs, to the intermediate product, the EDCs, several distinctions between the two cell populations are apparent. The difference in the 242 cell surface markers as expressed on CDCs versus EDCs is provided in Table 12 and visually depicted in FIGS. 17A-17J. Comp #1 corresponds to EDC/CDC Line #1, Comp #2 corresponds to EDC/CDC Line #2, Comp #5 corresponds to EDC/CDC Line #5, and Comp #6 corresponds to EDC/CDC Line #6. Recognition of distinct marker profiles is used, in several embodiments, to determine whether a cell population produced according to the methods disclosed herein represents true CDC population or a CDC population "contaminated" with EDCs. Distinguishing these populations can, in several embodiments, serve as a cell processing quality control measure (e.g., a marker profile can assist in identifying where in the production protocol a certain population of cells exists). Of the roughly 15 markers that distinguish CDCs from EDCs, three markers appear to clearly distinguish CDCs from EDCs, namely, SSEA-4, CD227, and CD141.

Stage-specific embryonic antigen-4 (SSEA-4) is expressed on between about 1% and about 18% of CDCs but on about 30% to about 52% of EDCs (on average a 28% reduction in expression from EDC to CDC). SSEA-4 is a glycosphingolipid and is associated with the identification of a variety of cells with pluripotent and/or stem cell-like characteristics. Decrease of SSEA-4 expression in CDCs compared to EDCs may, in some embodiments, be related to the EDCs being a more pluripotent and/or more stem cell-like population.

CD227 (also known as MUC1) is a transmembrane epithelial mucin glycoprotein which tends to be overexpressed in adenocarcinomas and hematopoietic cell malignancies (e.g., T and B cell lymphomas and myeloams). CD227 is expressed on approximately 9%-68% of CDCs, but is expressed on between about 72% to about 82% of EDCs. Thus, the procedures for production of CDCs as disclosed herein result in a decrease of CD227 expression from the EDC stage to the CDC stage.

CD141 (also known as thrombomodulin) is expressed on the surface of endothelial cells and functions as a cofactor for thrombin. While typically associated with the reduction of blood coagulation, the reduction of the expression of CD141 (from between 72% to about 86% on EDCs to about 30%-59% on CDCs) may, as discussed above, play a role in the CDCs' ability to promote angiogenesis.

In addition to SSEA-4, as discussed above, which, in several embodiments, is expressed on CDCs at a lower level (as compared to EDCs) due to the CDC production methods disclosed herein, CD146 also appears to be expressed, generally, at a lower level on CDCs (expressed on ~65%-90% of EDCs and ~14%-78% of CDCs) as compared to EDCs. As discussed above, CD146 is also known as melanoma cell adhesion molecule (MCAM), is negatively correlated with therapeutic potency, and is a marker for endothelial cells and appears to be associated with the formation of the junction of endothelial cells with the actin cytoskeleton. CD146 is also used as a marker for pericytes and reduced expression in CDCs as compared to EDCs may, in some embodiments, be related to the derivation of CDCs from pericytes in the heart.

Although the embodiments of the inventions have been disclosed in the context of a certain preferred embodiments and examples, it will be understood by those skilled in the art that the present inventions extend beyond the specifically disclosed embodiments to other alternative embodiments and/or uses of the inventions and obvious modifications and equivalents thereof. In addition, while a number of variations of the inventions have been shown and described in detail, other modifications, which are within the scope of the inventions, will be readily apparent to those of skill in the art based upon this disclosure. It is also contemplated that various combinations or subcombinations of the specific features and aspects of the embodiments may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. For all of the embodiments described herein the steps of the methods need not be performed sequentially. Thus, it is intended that the scope of the present inventions herein disclosed should not be limited by the particular disclosed embodiments described above.

TABLE 9

Cell Surface Markers Evaluated

| | | | | | | |
|---|---|---|---|---|---|---|
| CD1a | CD35 | CD66 | CD112 | CD165 | CD321(F11 | CD201 |
| CD1b | CD36 | (a. c. d. e) | CD114 | CD166 | Rcptr) | CD210 |
| CD1d | CD37 | CD66b | CD116 | CD171 | CDw327 | CD212 |
| CD2 | CD38 | CD66f | CD117 | CD172b | CDw328 | CD267 |
| CD3 | CD39 | CD69 | CD118 | CD177 | CDw329 | CD294 |
| CD4 | CD40 | CD70 | (LIF rcptr) | CD178 | CD335(NKP46) | CD326 |
| CD4v4 | CD41a | CD71 | CD119 | CD180 | CD336 | Cutaneous |
| CD5 | CD41b | CD72 | CD120a | CD181 | CD337 | Lymph. Antigen |
| CD6 | CD42a | CD73 | CD121a | CD183 | CD338(ABCG2) | INT B7 |
| CD7 | CD42b | CD74 | CD121b | CD184 | CD340(Her2) | SSEA-3 |
| CD8a | CD43 | CD75 | CD122 | CD193 | abTCR | |
| CD8b | CD44 | CD77 | CD123 | CD195 | B2-uGlob | |
| CD9 | CD45 | CD79b | CD124 | CD196 | BLTR-1 | |
| CD10 | CD45RA | CD80 | CD126 | CD197 | CLIP | |
| CD11a | CD45RB | CD81 | CD127 | CD200 | CMRF-44 | |
| CD11b | CD45RO | CD83 | CD128b | CD205 | CMRF-56 | |
| CD11c | CD46 | CD84 | CD130 | CD206 | EGF-r | |
| CD13 | CD47 | CD85 | CD134 | CD209 | Fmlp-r | |
| CD14 | CD48 | CD86 | CD135 | CD220 | gd TCR | |
| CD15 | CD49a | CD87 | CD137 | CD221 | Hem. Prog. Cell | |
| CD15s | CD49b | CD88 | CD137L | CD226 | HLA-A, B, C | |
| CD16 | CD49c | CD89 | CD138 | CD227 | HLA-A2 | |
| CD18 | CD49d | CD90 | CD140a | CD229 | HLA-DQ | |
| CD19 | CD49e | CD91 | CD140b | CD231 | HLA-DR | |
| CD20 | CD50 | CDw93 | CD141 | CD235a | HLA-DR, DP, DQ | |
| CD21 | CD51/61 | CD94 | CD142 | CD243 | Invariant NKT | |
| CD22 | CD53 | CD95 | CD144 | (p-glycoProtein) | Disialoganglioside | |
| CD23 | CD54 | CD97 | CD146 | CD244 | GD2 | |
| CD24 | CD55 | CD98 | CD147 | CD255 | MIC A/B | |
| CD25 | CD56 | CD99 | CD150 | (Tweak) | NKB1 | |
| CD26 | CD57 | CD99R | CD151 | CD268 | SSEA-1 | |
| CD27 | CD58 | CD100 | CD152 | CD271 | SSEA-4 | |
| CD28 | CD59 | CD102 | CD153 | CD273 | TRA-1-60 | |
| CD29 | CD61 | CD103 | CD154 | CD274 | TRA-1-81 | |
| CD30 | CD62E | CD105 | CD158a | CD275 | Vb 23 | |
| CD31 | CD62L | CD106 | CD158b | (B7-H2) | Vb 8 | |
| CD32 | CD62P | CD107a | CD161 | CD278 | CD49f | |
| CD33 | CD63 | CD107b | CD162 | CD279 | CD104 | |
| CD34 | CD64 | CD108 | CD163 | CD282 | CD120b | |
| | | CD109 | CD164 | CD305(LAIR-1) | CD132 | |
| | | | | CD309 | | |
| | | | | CD314(NKG2D) | | |

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 nanometers" includes "10 nanometers."

What is claimed is:

1. A method for preparing filtered cardiosphere-derived cells (CDCs) suitable for allogeneic cardiac stem cell therapy, comprising:
    receiving donor cardiac tissue from a subject;
    processing said piece of donor cardiac tissue into a plurality of tissue explants ranging from about 200 μm³ to about 600 μm³, wherein said explants range from about 0.3 to about 0.6 grams;
    enzymatically digesting said explants for a time ranging from about 30 seconds to about 5 minutes;
    culturing said explants at a density of about 1 explant per 400 to 700 cm² culturing surface area until cells migrate from said explant;
    collecting the cells that migrate from the explant;
    culturing the collected cells in order to generate CDCs;
    harvesting the CDCs; and
    filtering said harvested CDCs to remove particles greater than 50 μm in diameter to isolate CDCs less than 50 μm in diameter to facilitate allogeneic cardiac stem cell therapy.

2. The method of claim 1, wherein the isolated CDCs that are sized less than 50 μm in diameter are suitable for intracoronary delivery and passage into cardiac arterioles having an inner diameter of about 50 μm.

3. The method of claim 1, wherein said filtering comprises filtering said harvested CDCs through a first filter to remove particles greater in size than about 140 μm and through a second filter to remove particles greater than about 50 μm.

4. The method of claim 3, wherein said first and said second filter comprise a single two-stage filter device.

5. The method of claim 1, wherein said donor cardiac tissue is optionally cryopreserved for a period of time ranging from about 1 to about 90 days prior to said processing.

6. The method of claim 1, wherein said processing further comprises transfer of said explant from a dissection vessel to a culture vessel by flooding the explant with culture media rather than hand-placing the explant in the culture vessel, wherein said transfer by flooding reduces risk of contamination and reduces perturbation of said explant.

7. The method of claim 1, wherein said plurality of explants comprises a plurality of explants obtained from one region of the donor cardiac tissue.

8. The method of claim 1, wherein said plurality of explants comprises a plurality of explants obtained from more than one region of the donor cardiac tissue.

9. The method of claim 1, wherein said culturing further comprises addition of one or more of heparin and L-glutamine to a culture media in order to reduce clumping of cells migrating from said explant.

10. The method of claim 1, further comprising freezing the CDCs suitable for allogeneic cardiac stem cell therapy.

11. The method of claim 1, wherein the donor cardiac tissue ranges in size from about 1 gram to about 300 grams.

12. The method of claim 1, wherein said processing yields a plurality of tissue explants that are cuboidal in shape.

13. The method of claim 1, wherein the donor cardiac tissue is processed within 3 days from removal from said subject.

14. The method according to claim 1, wherein said CDCs suitable for allogeneic cardiac stem cell therapy comprise less than 1% particles greater than 140 μm.

15. The method according to claim 1, wherein said CDCs suitable for allogeneic cardiac stem cell therapy comprise essentially 0% particles greater than 150 μm.

16. The method according to claim 1, wherein said CDCs suitable for allogeneic cardiac stem cell therapy comprise less than 1% particles greater than 50 μm.

17. The method according to claim 1, further comprising delivering said isolated CDCs to a subject via intracoronary delivery.

18. A method for preparing cardiosphere derived cells (CDCs), comprising:
    processing cardiac tissue into a plurality of tissue explants;
    culturing said explants until cells migrate from said explant;
    collecting the cells that migrate from the explant;
    culturing the collected cells in order to generate CDCs;
    harvesting the CDCs;
    filtering said harvested CDCs remove particles greater than about 50 μm.

19. The method according to claim 18, wherein said cardiac tissue is processed into a plurality of tissue explants ranging from about 0.3 to about 0.6 grams.

20. The method according to claim 18, wherein said explants are cultured at a density of about 1 explant per 400 to 700 cm² culturing surface area.

* * * * *